US012709742B2

(12) United States Patent
Heo et al.

(10) Patent No.: US 12,709,742 B2
(45) Date of Patent: Aug. 18, 2026

(54) RNA EXPRESSION MODULATING OR EDITING METHOD VIA REGULATION OF CAS13 PROTEIN

(71) Applicant: Korea Advanced Institute of Science and Technology, Daejeon (KR)

(72) Inventors: Won Do Heo, Daejeon (KR); Jeonghye Yu, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 784 days.

(21) Appl. No.: 17/907,472

(22) PCT Filed: Jul. 8, 2022

(86) PCT No.: PCT/KR2022/009993
§ 371 (c)(1),
(2) Date: Sep. 27, 2022

(87) PCT Pub. No.: WO2023/282710
PCT Pub. Date: Jan. 12, 2023

(65) Prior Publication Data

US 2024/0309343 A1 Sep. 19, 2024

(30) Foreign Application Priority Data

Jul. 8, 2021 (KR) ........................ 10-2021-0089435
Apr. 20, 2022 (KR) ........................ 10-2022-0048556

(51) Int. Cl.

| | |
|---|---|
| ***C12N 9/22*** | (2006.01) |
| ***C12N 9/86*** | (2006.01) |
| ***C12N 13/00*** | (2006.01) |
| ***C12N 15/11*** | (2006.01) |
| ***C12N 15/85*** | (2006.01) |

(52) U.S. Cl.
CPC ................. *C12N 9/22* (2013.01); *C12N 9/86* (2013.01); *C12N 13/00* (2013.01); *C12N 15/111* (2013.01); *C12N 15/85* (2013.01); *C12N 2310/20* (2017.05); *C12Y 305/04004* (2013.01)

(58) Field of Classification Search
CPC .... C12N 9/22; C12N 15/111; C12N 2310/20; C12N 15/102; A61K 48/005; C07K 2319/70
See application file for complete search history.

(56) References Cited

U.S. PATENT DOCUMENTS

| | | | |
|---|---|---|---|
| 2021/0071178 | A1 | 3/2021 | Borrajo |
| 2022/0364071 | A1 | 11/2022 | Zhang et al. |

FOREIGN PATENT DOCUMENTS

| | | | |
|---|---|---|---|
| CN | 111206053 | A | 5/2020 |
| KR | 1020210053898 | A | 5/2021 |
| WO | 2015089427 | A1 | 6/2015 |
| WO | 2017219027 | A1 | 12/2017 |
| WO | 2018191388 | A1 | 10/2018 |

OTHER PUBLICATIONS

Zetsche, B. et.al, “A Split Cas9 Architecture for Inducible Genome editing andTranscription Modulation” Nat Biotechnol., Feb. 2015, vol. 33, No. 2, pp. 1-6.
Du M. et.al, “CRISPR artificial splicing factors” , Nature Communications, Jun. 12, 2020, vol. 11, 2973, pp. 1-11.
International Patent Application No. PCT/KR2022/009993, International Search Report and Written Opinion with Partial English Machine Translation mailed Oct. 17, 2022, 5 pages.
Gao, J. et al., “A New Tool for CRISOR-Cas13a-Based Cancer Gene Therapy,” Molecular Therapy: Oncolytics vol. Dec. 19, 2020, pp. 79-92.
Wang, Q. et al., “The CRISPR-Cas13a Gene Editing System Induces Collateral Cleavage of RNA in Glicoma Cells,” Adv. Sci. 2019, 6, 1901299, 7 pgs.
Li, H. et al., “CRISPR-Cas13a Cleavage of Cengue Virus N53 Gene Efficiently Inhibits Viral Replication,” Molecular Therapy: Nucleic Acids vol. Mar. 19, 2020, pp. 1460-1469.
Zhao, X. et al., “A CRISPR-Cas13a System for efficient and specific therapeutic targeting of mutant KRAS for pancreatic cancer treatment,” Cancer Letters, vol. 431, Sep. 1, 2018, pp. 171-181.
Zhou, H. et al., “Glia-to-Neuron Conversion by CRISPR-CasRx Alleviates Symptoms of Neurological Disease in Mice,” Cell, vol. 181, Issue 3, Apr. 30, 2020, pp. 590-603.
Kushawah, G. et al., “CRISPR-Cas13d Induces Efficient mRNA Knockdown in Animal Embryos,” Developmental Cell, vol. 54, Issue 6, Sep. 28, 2020, pp. 805-817.
Nobe, T. et al., “Rapamycin-induced oligomer formation system of FRB-FKBP fusion proteins,” J Biosci Bioeng. Jul. 2016; 122(1): pp. 40-46.

*Primary Examiner* — J. E. Angell
(74) *Attorney, Agent, or Firm* — Fredrikson & Byron, P.A.

(57) ABSTRACT

The present invention relates to a RNA expression modulating or editing method through chemical or optogenetic regulation of Cas13 protein activity. Specifically, in order to regulate the activity of Cas13 in the CRISPR-Cas13 system, a fragment of the Cas13 protein was generated to enable recombination, and a chemogenetically or optogenetically bindable protein was linked to each fragment. And, it was confirmed that the Cas13 protein can be activated by treatment of a low molecular weight compound or irradiation of light. Accordingly, the method of the present invention can be effectively used for disease treatment by regulating RNA expression or editing RNA mutations related to disease.

12 Claims, 30 Drawing Sheets

Specification includes a Sequence Listing.

FIG. 3

| N fragments | GS16 | FRB | GS16 |
|---|---|---|---|

| GS16 | FKBP | GS16 | C fragments |

```
                              SEQUENCE LISTING

Sequence total quantity: 75
SEQ ID NO: 1              moltype = AA  length = 272
FEATURE                   Location/Qualifiers
REGION                    1..272
                          note = N272 Fragment amino acid sequence
source                    1..272
                          mol_type = protein
                          organism = synthetic construct
SEQUENCE: 1
MNIPALVENQ KKYFGTYSVM AMLNAQTVLD HIQKVADIEG EQNENNENLW FHPVMSHLYN  60
AKNGYDKQPE KTMFIIERLQ SYFPFLKIMA ENQREYSNGK YKQNRVEVNS NDIFEVLKRA  120
FGVLKMYRDL TNHYKTYEEK LNDGCEFLTS TEQPLSGMIN NYYTVALRNM NERYGYKTED  180
LAFIQDKRFK FVKDAYGKKK SQVNTGFFLS LQDYNGDTQK KLHLSGVGIA LLICLFLDKQ  240
YINIFLSRLP IFSSYNAQSE ERRIIIRSFG IN                                272

SEQ ID NO: 2              moltype = AA  length = 2583
FEATURE                   Location/Qualifiers
REGION                    1..2583
                          note = C273 Fragment amino acid sequence
source                    1..2583
                          mol_type = protein
                          organism = synthetic construct
SEQUENCE: 2
SERILELYSL EUPROLYSAS PARGILEHIS SERGLULYSS ERASNLYSSE RVALALAMET  60
ASPMETLEUA SNGLUVALLY SARGCYSPRO ASPGLULEUP HETHRTHRLE USERALAGLU  120
LYSGLNSERA RGPHEARGIL EILESERASP ASPHISASNG LUVALLEUME TLYSARGSER  180
SERASPARGP HEVALPROLE ULEULEUGLN TYRILEASPT YRGLYLYSLE UPHEASPHIS  240
ILEARGPHEH ISVALASNME TGLYLYSLEU ARGTYRLEUL EULYSALAAS PLYSTHRCYS  300
ILEASPGLYG LNTHRARGVA LARGVALILE GLUGLNPROL EUASNGLYPH EGLYARGLEU  360
GLUGLUALAG LUTHRMETAR GLYSGLNGLU ASNGLYTHRP HEGLYASNSE RGLYILEARG  420
ILEARGASPP HEGLUASNME TLYSARGASP ASPALAASNP ROALAASNTY RPROTYRILE  480
VALASPTHRT YRTHRHISTY RILELEUGLU ASNASNLYSV ALGLUMETPH EILEASNASP  540
LYSGLUASPS ERALAPROLE ULEUPROVAL ILEGLUASPA SPARGTYRVA LVALLYSTHR  600
ILEPROSERC YSARGMETSE RTHRLEUGLU ILEPROALAM ETALAPHEHI SMETPHELEU  660
PHEGLYSERL YSLYSTHRGL ULYSLEUILE VALASPVALH ISASNARGTY RLYSARGLEU  720
PHEGLNALAM ETGLNLYSGL UGLUVALTHR ALAGLUASNI LEALASERPH EGLYILEALA  780
GLUSERASPL EUPROGLNLY SILELEUASP LEUILESERG LYASNALAHI SGLYLYSASP  840
VALASPALAP HEILEARGLE UTHRVALASP ASPMETLEUT HRASPTHRGL UARGARGILE  900
LYSARGPHEL YSASPASPAR GLYSSERILE ARGSERALAA SPASNLYSME TGLYLYSARG  960
GLYPHELYSG LNILESERTH RGLYLYSLEU ALAASPPHEL EUALALYSAS PILEVALLEU  1020
PHEGLNPROS ERVALASNAS PGLYGLUASN LYSILETHRG LYLEUASNTY RARGILEMET  1080
GLNSERALAI LEALAVALTY RASPSERGLY ASPASPTYRG LUALALYSGL NGLNPHELYS  1140
LEUMETPHEG LULYSALAAR GLEUILEGLY LYSGLYTHRT HRGLUPROHI SPROPHELEU  1200
TYRLYSVALP HEALAARGSE RILEPROALA ASNALAVALG LUPHETYRGL UARGTYRLEU  1260
ILEGLUARGL YSPHETYRLE UTHRGLYLEU SERASNGLUI LELYSLYSGL YASNARGVAL  1320
ASPVALPROP HEILEARGAR GASPGLNASN LYSTRPLYST HRPROALAME TLYSTHRLEU  1380
GLYARGILET YRSERGLUAS PLEUPROVAL GLULEUPROA RGGLNMETPH EASPASNGLU  1440
ILELYSSERH ISLEULYSSE RLEUPROGLN METGLUGLYI LEASPPHEAS NASNALAASN  1500
```

```
VALTHRTYRL EUILEALAGL UTYRMETLYS ARGVALLEUA SPASPASPPH EGLNTHRPHE  1560
TYRGLNTRPA SNARGASNTY RARGTYRMET ASPMETLEUL YSGLYGLUTY RASPARGLYS  1620
GLYSERLEUG LNHISCYSPH ETHRSERVAL GLUGLUARGG LUGLYLEUTR PLYSGLUARG  1680
ALASERARGT HRGLUARGTY RARGLYSGLN ALASERASNL YSILEARGSE RASNARGGLN  1740
METARGASNA LASERSERGL UGLUILEGLU THRILELEUA SPLYSARGLE USERASNSER  1800
ARGASNGLUT YRGLNLYSSE RGLULYSVAL ILEARGARGT YRARGVALGL NASPALALEU  1860
LEUPHELEUL EUALALYSLY STHRLEUTHR GLULEUALAA SPPHEASPGL YGLUARGPHE  1920
LYSLEULYSG LUILEMETPR OASPALAGLU LYSGLYILEL EUSERGLUIL EMETPROMET  1980
SERPHETHRP HEGLULYSGL YGLYLYSLYS TYRTHRILET HRSERGLUGL YMETLYSLEU  2040
LYSASNTYRG LYASPPHEPH EVALLEUALA SERASPLYSA RGILEGLYAS NLEULEUGLU  2100
LEUVALGLYS ERASPILEVA LSERLYSGLU ASPILEMETG LUGLUPHEAS NLYSTYRASP  2160
GLNCYSARGP ROGLUILESE RSERILEVAL PHEASNLEUG LULYSTRPAL APHEASPTHR  2220
TYRPROGLUL EUSERALAAR GVALASPARG GLUGLULYSV ALASPPHELY SSERILELEU  2280
LYSILELEUL EUASNASNLY SASNILEASN LYSGLUGLNS ERASPILELE UARGLYSILE  2340
ARGASNALAP HEASPHISAS NASNTYRPRO ASPLYSGLYV ALVALGLUIL ELYSALALEU  2400
PROGLUILEA LAMETSERIL ELYSLYSALA PHEGLYGLUT YRALAILEME TLYSGLYSER  2460
LEUGLNLEUP ROPROLEUGL UARGLEUTHR LEUGLYSERS ERTYRPROTY RASPVALPRO  2520
ASPTYRALAT YRPROTYRAS PVALPROASP TYRALATYRP ROTYRASPVA LPROASPTYR  2580
ALA                                                                2583
```

```
SEQ ID NO: 3           moltype = AA  length = 286
FEATURE                Location/Qualifiers
REGION                 1..286
                       note = N286 Fragment amino acid sequence
source                 1..286
                       mol_type = protein
                       organism = synthetic construct
SEQUENCE: 3
MNIPALVENQ KKYFGTYSVM AMLNAQTVLD HIQKVADIEG EQNENNENLW FHPVMSHLYN  60
AKNGYDKQPE KTMFIIERLQ SYFPFLKIMA ENQREYSNGK YKQNRVEVNS NDIFEVLKRA  120
FGVLKMYRDL TNHYKTYEEK LNDGCEFLTS TEQPLSGMIN NYYTVALRNM NERYGYKTED  180
LAFIQDKRFK FVKDAYGKKK SQVNTGFFLS LQDYNGDTQK KLHLSGVGIA LLICLFLDKQ  240
YINIFLSRLP IFSSYNAQSE ERRIIIRSFG INSIKLPKDR IHSEKS                 286
```

```
SEQ ID NO: 4           moltype = AA  length = 2541
FEATURE                Location/Qualifiers
REGION                 1..2541
                       note = C287 Fragment amino acid sequence
source                 1..2541
                       mol_type = protein
                       organism = synthetic construct
SEQUENCE: 4
ASNLYSSERV ALALAMETAS PMETLEUASN GLUVALLYSA RGCYSPROAS PGLULEUPHE  60
THRTHRLEUS ERALAGLULY SGLNSERARG PHEARGILEI LESERASPAS PHISASNGLU  120
VALLEUMETL YSARGSERSE RASPARGPHE VALPROLEUL EULEUGLNTY RILEASPTYR  180
GLYLYSLEUP HEASPHISIL EARGPHEHIS VALASNMETG LYLYSLEUAR GTYRLEULEU  240
LYSALAASPL YSTHRCYSIL EASPGLYGLN THRARGVALA RGVALILEGL UGLNPROLEU  300
ASNGLYPHEG LYARGLEUGL UGLUALAGLU THRMETARGL YSGLNGLUAS NGLYTHRPHE  360
GLYASNSERG LYILEARGIL EARGASPPHE GLUASNMETL YSARGASPAS PALAASNPRO  420
ALAASNTYRP ROTYRILEVA LASPTHRTYR THRHISTYRI LELEUGLUAS NASNLYSVAL  480
GLUMETPHEI LEASNASPLY SGLUASPSER ALAPROLEUL EUPROVALIL EGLUASPASP  540
ARGTYRVALV ALLYSTHRIL EPROSERCYS ARGMETSERT HRLEUGLUIL EPROALAMET  600
ALAPHEHISM ETPHELEUPH EGLYSERLYS LYSTHRGLUL YSLEUILEVA LASPVALHIS  660
ASNARGTYRL YSARGLEUPH EGLNALAMET GLNLYSGLUG LUVALTHRAL AGLUASNILE  720
ALASERPHEG LYILEALAGL USERASPLEU PROGLNLYSI LELEUASPLE UILESERGLY  780
ASNALAHISG LYLYSASPVA LASPALAPHE ILEARGLEUT HRVALASPAS PMETLEUTHR  840
ASPTHRGLUA RGARGILELY SARGPHELYS ASPASPARGL YSSERILEAR GSERALAASP  900
ASNLYSMETG LYLYSARGGL YPHELYSGLN ILESERTHRG LYLYSLEUAL AASPPHELEU  960
ALALYSASPI LEVALLEUPH EGLNPROSER VALASNASPG LYGLUASNLY SILETHRGLY  1020
LEUASNTYRA RGILEMETGL NSERALAILE ALAVALTYRA SPSERGLYAS PASPTYRGLU  1080
ALALYSGLNG LNPHELYSLE UMETPHEGLU LYSALAARGL EUILEGLYLY SGLYTHRTHR  1140
GLUPROHISP ROPHELEUTY RLYSVALPHE ALAARGSERI LEPROALAAS NALAVALGLU  1200
PHETYRGLUA RGTYRLEUIL EGLUARGLYS PHETYRLEUT HRGLYLEUSE RASNGLUILE  1260
LYSLYSGLYA SNARGVALAS PVALPROPHE ILEARGARGA SPGLNASNLY STRPLYSTHR  1320
PROALAMETL YSTHRLEUGL YARGILETYR SERGLUASPL EUPROVALGL ULEUPROARG  1380
GLNMETPHEA SPASNGLUIL ELYSSERHIS LEULYSSERL EUPROGLNME TGLUGLYILE  1440
ASPPHEASNA SNALAASNVA LTHRTYRLEU ILEALAGLUT YRMETLYSAR GVALLEUASP  1500
ASPASPPHEG LNTHRPHETY RGLNTRPASN ARGASNTYRA RGTYRMETAS PMETLEULYS  1560
GLYGLUTYRA SPARGLYSGL YSERLEUGLN HISCYSPHET HRSERVALGL UGLUARGGLU  1620
GLYLEUTRPL YSGLUARGAL ASERARGTHR GLUARGTYRA RGLYSGLNAL ASERASNLYS  1680
ILEARGSERA SNARGGLNME TARGASNALA SERSERGLUG LUILEGLUTH RILELEUASP  1740
LYSARGLEUS ERASNSERAR GASNGLUTYR GLNLYSSERG LULYSVALIL EARGARGTYR  1800
ARGVALGLNA SPALALEULE UPHELEULEU ALALYSLYST HRLEUTHRGL ULEUALAASP  1860
PHEASPGLYG LUARGPHELY SLEULYSGLU ILEMETPROA SPALAGLULY SGLYILELEU  1920
SERGLUILEM ETPROMETSE RPHETHRPHE GLULYSGLYG LYLYSLYSTY RTHRILETHR  1980
SERGLUGLYM ETLYSLEULY SASNTYRGLY ASPPHEPHEV ALLEUALASE RASPLYSARG  2040
ILEGLYASNL EULEUGLULE UVALGLYSER ASPILEVALS ERLYSGLUAS PILEMETGLU  2100
GLUPHEASNL YSTYRASPGL NCYSARGPRO GLUILESERS ERILEVALPH EASNLEUGLU  2160
LYSTRPALAP HEASPTHRTY RPROGLULEU SERALAARGV ALASPARGGL UGLULYSVAL  2220
```

-continued

```
ASPPHELYSS ERILELEULY SILELEULEU ASNASNLYSA SNILEASNLY SGLUGLNSER  2280
ASPILELEUA RGLYSILEAR GASNALAPHE ASPHISASNA SNTYRPROAS PLYSGLYVAL  2340
VALGLUILEL YSALALEUPR OGLUILEALA METSERILEL YSLYSALAPH EGLYGLUTYR  2400
ALAILEMETL YSGLYSERLE UGLNLEUPRO PROLEUGLUA RGLEUTHRLE UGLYSERSER  2460
TYRPROTYRA SPVALPROAS PTYRALATYR PROTYRASPV ALPROASPTY RALATYRPRO  2520
TYRASPVALP ROASPTYRAL A                                            2541

SEQ ID NO: 5           moltype = AA  length = 351
FEATURE                Location/Qualifiers
REGION                 1..351
                       note = N351 Fragment amino acid sequence
source                 1..351
                       mol_type = protein
                       organism = synthetic construct
SEQUENCE: 5
MNIPALVENQ KKYFGTYSVM AMLNAQTVLD HIQKVADIEG EQNENNENLW FHPVMSHLYN  60
AKNGYDKQPE KTMFIIERLQ SYFPFLKIMA ENQREYSNGK YKQNRVEVNS NDIFEVLKRA  120
FGVLKMYRDL TNHYKTYEEK LNDGCEFLTS TEQPLSGMIN NYYTVALRNM NERYGYKTED  180
LAFIQDKRFK FVKDAYGKKK SQVNTGFFLS LQDYNGDTQK KLHLSGVGIA LLICLFLDKQ  240
YINIFLSRLP IFSSYNAQSE ERRIIIRSFG INSIKLPKDR IHSEKSNKSV AMDMLNEVKR  300
CPDELFTTLS AEKQSRFRII SDDHNEVLMK RSSDRFVPLL LQYIDYGKLF D           351

SEQ ID NO: 6           moltype = AA  length = 2346
FEATURE                Location/Qualifiers
REGION                 1..2346
                       note = C352 Fragment amino acid sequence
source                 1..2346
                       mol_type = protein
                       organism = synthetic construct
SEQUENCE: 6
HISILEARGP HEHISVALAS NMETGLYLYS LEUARGTYRL EULEULYSAL AASPLYSTHR  60
CYSILEASPG LYGLNTHRAR GVALARGVAL ILEGLUGLNP ROLEUASNGL YPHEGLYARG  120
LEUGLUGLUA LAGLUTHRME TARGLYSGLN GLUASNGLYT HRPHEGLYAS NSERGLYILE  180
ARGILEARGA SPPHEGLUAS NMETLYSARG ASPASPALAA SNPROALAAS NTYRPROTYR  240
ILEVALASPT HRTYRTHRHI STYRILELEU GLUASNASNL YSVALGLUME TPHEILEASN  300
ASPLYSGLUA SPSERALAPR OLEULEUPRO VALILEGLUA SPASPARGTY RVALVALLYS  360
THRILEPROS ERCYSARGME TSERTHRLEU GLUILEPROA LAMETALAPH EHISMETPHE  420
LEUPHEGLYS ERLYSLYSTH RGLULYSLEU ILEVALASPV ALHISASNAR GTYRLYSARG  480
LEUPHEGLNA LAMETGLNLY SGLUGLUVAL THRALAGLUA SNILEALASE RPHEGLYILE  540
ALAGLUSERA SPLEUPROGL NLYSILELEU ASPLEUILES ERGLYASNAL AHISGLYLYS  600
ASPVALASPA LAPHEILEAR GLEUTHRVAL ASPASPMETL EUTHRASPTH RGLUARGARG  660
ILELYSARGP HELYSASPAS PARGLYSSER ILEARGSERA LAASPASNLY SMETGLYLYS  720
ARGGLYPHEL YSGLNILESE RTHRGLYLYS LEUALAASPP HELEUALALY SASPILEVAL  780
LEUPHEGLNP ROSERVALAS NASPGLYGLU ASNLYSILET HRGLYLEUAS NTYRARGILE  840
METGLNSERA LAILEALAVA LTYRASPSER GLYASPASPT YRGLUALALY SGLNGLNPHE  900
LYSLEUMETP HEGLULYSAL AARGLEUILE GLYLYSGLYT HRTHRGLUPR OHISPROPHE  960
LEUTYRLYSV ALPHEALAAR GSERILEPRO ALAASNALAV ALGLUPHETY RGLUARGTYR  1020
LEUILEGLUA RGLYSPHETY RLEUTHRGLY LEUSERASNG LUILELYSLY SGLYASNARG  1080
VALASPVALP ROPHEILEAR GARGASPGLN ASNLYSTRPL YSTHRPROAL AMETLYSTHR  1140
LEUGLYARGI LETYRSERGL UASPLEUPRO VALGLULEUP ROARGGLNME TPHEASPASN  1200
GLUILELYSS ERHISLEULY SSERLEUPRO GLNMETGLUG LYILEASPPH EASNASNALA  1260
ASNVALTHRT YRLEUILEAL AGLUTYRMET LYSARGVALL EUASPASPAS PPHEGLNTHR  1320
PHETYRGLNT RPASNARGAS NTYRARGTYR METASPMETL EULYSGLYGL UTYRASPARG  1380
LYSGLYSERL EUGLNHISCY SPHETHRSER VALGLUGLUA RGGLUGLYLE UTRPLYSGLU  1440
ARGALASERA RGTHRGLUAR GTYRARGLYS GLNALASERA SNLYSILEAR GSERASNARG  1500
GLNMETARGA SNALASERSE RGLUGLUILE GLUTHRILEL EUASPLYSAR GLEUSERASN  1560
SERARGASNG LUTYRGLNLY SSERGLULYS VALILEARGA RGTYRARGVA LGLNASPALA  1620
LEULEUPHEL EULEUALALY SLYSTHRLEU THRGLULEUA LAASPPHEAS PGLYGLUARG  1680
PHELYSLEUL YSGLUILEME TPROASPALA GLULYSGLYI LELEUSERGL UILEMETPRO  1740
METSERPHET HRPHEGLULY SGLYGLYLYS LYSTYRTHRI LETHRSERGL UGLYMETLYS  1800
LEULYSASNT YRGLYASPPH EPHEVALLEU ALASERASPL YSARGILEGL YASNLEULEU  1860
GLULEUVALG LYSERASPIL EVALSERLYS GLUASPILEM ETGLUGLUPH EASNLYSTYR  1920
ASPGLNCYSA RGPROGLUIL ESERSERILE VALPHEASNL EUGLULYSTR PALAPHEASP  1980
THRTYRPROG LULEUSERAL AARGVALASP ARGGLUGLUL YSVALASPPH ELYSSERILE  2040
LEULYSILEL EULEUASNAS NLYSASNILE ASNLYSGLUG LNSERASPIL ELEUARGLYS  2100
ILEARGASNA LAPHEASPHI SASNASNTYR PROASPLYSG LYVALVALGL UILELYSALA  2160
LEUPROGLUI LEALAMETSE RILELYSLYS ALAPHEGLYG LUTYRALAIL EMETLYSGLY  2220
SERLEUGLNL EUPROPROLE UGLUARGLEU THRLEUGLYS ERSERTYRPR OTYRASPVAL  2280
PROASPTYRA LATYRPROTY RASPVALPRO ASPTYRALAT YRPROTYRAS PVALPROASP  2340
TYRALA                                                             2346

SEQ ID NO: 7           moltype = AA  length = 480
FEATURE                Location/Qualifiers
REGION                 1..480
                       note = N480 Fragment amino acid sequence
source                 1..480
                       mol_type = protein
                       organism = synthetic construct
SEQUENCE: 7
```

-continued

```
MNIPALVENQ KKYFGTYSVM AMLNAQTVLD HIQKVADIEG EQNENNENLW FHPVMSHLYN  60
AKNGYDKQPE KTMFIIERLQ SYFPFLKIMA ENQREYSNGK YKQNRVEVNS NDIFEVLKRA  120
FGVLKMYRDL TNHYKTYEEK LNDGCEFLTS TEQPLSGMIN NYYTVALRNM NERYGYKTED  180
LAFIQDKRFK FVKDAYGKKK SQVNTGFFLS LQDYNGDTQK KLHLSGVGIA LLICLFLDKQ  240
YINIFLSRLP IFSSYNAQSE ERRIIIRSFG INSIKLPKDR IHSEKSNKSV AMDMLNEVKR  300
CPDELFTTLS AEKQSRFRII SDDHNEVLMK RSSDRFVPLL LQYIDYGKLF DHIRFHVNMG  360
KLRYLLKADK TCIDGQTRVR VIEQPLNGFG RLEEAETMRK QENGTFGNSG IRIRDFENMK  420
RDDANPANYP YIVDTYTHYI LENNKVEMFI NDKEDSAPLL PVIEDDRYVV KTIPSCRMST  480

SEQ ID NO: 8           moltype = AA  length = 1959
FEATURE                Location/Qualifiers
REGION                 1..1959
                       note = C481 Fragment amino acid sequence
source                 1..1959
                       mol_type = protein
                       organism = synthetic construct
SEQUENCE: 8
LEUGLUILEP ROALAMETAL APHEHISMET PHELEUPHEG LYSERLYSLY STHRGLULYS  60
LEUILEVALA SPVALHISAS NARGTYRLYS ARGLEUPHEG LNALAMETGL NLYSGLUGLU  120
VALTHRALAG LUASNILEAL ASERPHEGLY ILEALAGLUS ERASPLEUPR OGLNLYSILE  180
LEUASPLEUI LESERGLYAS NALAHISGLY LYSASPVALA SPALAPHEIL EARGLEUTHR  240
VALASPASPM ETLEUTHRAS PTHRGLUARG ARGILELYSA RGPHELYSAS PASPARGLYS  300
SERILEARGS ERALAASPAS NLYSMETGLY LYSARGGLYP HELYSGLNIL ESERTHRGLY  360
LYSLEUALAA SPPHELEUAL ALYSASPILE VALLEUPHEG LNPROSERVA LASNASPGLY  420
GLUASNLYSI LETHRGLYLE UASNTYRARG ILEMETGLNS ERALAILEAL AVALTYRASP  480
SERGLYASPA SPTYRGLUAL ALYSGLNGLN PHELYSLEUM ETPHEGLULY SALAARGLEU  540
ILEGLYLYSG LYTHRTHRGL UPROHISPRO PHELEUTYRL YSVALPHEAL AARGSERILE  600
PROALAASNA LAVALGLUPH ETYRGLUARG TYRLEUILEG LUARGLYSPH ETYRLEUTHR  660
GLYLEUSERA SNGLUILELY SLYSGLYASN ARGVALASPV ALPROPHEIL EARGARGASP  720
GLNASNLYST RPLYSTHRPR OALAMETLYS THRLEUGLYA RGILETYRSE RGLUASPLEU  780
PROVALGLUL EUPROARGGL NMETPHEASP ASNGLUILEL YSSERHISLE ULYSSERLEU  840
PROGLNMETG LUGLYILEAS PPHEASNASN ALAASNVALT HRTYRLEUIL EALAGLUTYR  900
METLYSARGV ALLEUASPAS PASPPHEGLN THRPHETYRG LNTRPASNAR GASNTYRARG  960
TYRMETASPM ETLEULYSGL YGLUTYRASP ARGLYSGLYS ERLEUGLNHI SCYSPHETHR  1020
SERVALGLUG LUARGGLUGL YLEUTRPLYS GLUARGALAS ERARGTHRGL UARGTYRARG  1080
LYSGLNALAS ERASNLYSIL EARGSERASN ARGGLNMETA RGASNALASE RSERGLUGLU  1140
ILEGLUTHRI LELEUASPLY SARGLEUSER ASNSERARGA SNGLUTYRGL NLYSSERGLU  1200
LYSVALILEA RGARGTYRAR GVALGLNASP ALALEULEUP HELEULEUAL ALYSLYSTHR  1260
LEUTHRGLUL EUALAASPPH EASPGLYGLU ARGPHELYSL EULYSGLUIL EMETPROASP  1320
ALAGLULYSG LYILELEUSE RGLUILEMET PROMETSERP HETHRPHEGL ULYSGLYGLY  1380
LYSLYSTYRT HRILETHRSE RGLUGLYMET LYSLEULYSA SNTYRGLYAS PPHEPHEVAL  1440
LEUALASERA SPLYSARGIL EGLYASNLEU LEUGLULEUV ALGLYSERAS PILEVALSER  1500
LYSGLUASPI LEMETGLUGL UPHEASNLYS TYRASPGLNC YSARGPROGL UILESERSER  1560
ILEVALPHEA SNLEUGLULY STRPALAPHE ASPTHRTYRP ROGLULEUSE RALAARGVAL  1620
ASPARGGLUG LULYSVALAS PPHELYSSER ILELEULYSI LELEULEUAS NASNLYSASN  1680
ILEASNLYSG LUGLNSERAS PILELEUARG LYSILEARGA SNALAPHEAS PHISASNASN  1740
TYRPROASPL YSGLYVALVA LGLUILELYS ALALEUPROG LUILEALAME TSERILELYS  1800
LYSALAPHEG LYGLUTYRAL AILEMETLYS GLYSERLEUG LNLEUPROPR OLEUGLUARG  1860
LEUTHRLEUG LYSERSERTY RPROTYRASP VALPROASPT YRALATYRPR OTYRASPVAL  1920
PROASPTYRA LATYRPROTY RASPVALPRO ASPTYRALA                         1959

SEQ ID NO: 9           moltype = AA  length = 550
FEATURE                Location/Qualifiers
REGION                 1..550
                       note = N550 Fragment amino acid sequence
source                 1..550
                       mol_type = protein
                       organism = synthetic construct
SEQUENCE: 9
MNIPALVENQ KKYFGTYSVM AMLNAQTVLD HIQKVADIEG EQNENNENLW FHPVMSHLYN  60
AKNGYDKQPE KTMFIIERLQ SYFPFLKIMA ENQREYSNGK YKQNRVEVNS NDIFEVLKRA  120
FGVLKMYRDL TNHYKTYEEK LNDGCEFLTS TEQPLSGMIN NYYTVALRNM NERYGYKTED  180
LAFIQDKRFK FVKDAYGKKK SQVNTGFFLS LQDYNGDTQK KLHLSGVGIA LLICLFLDKQ  240
YINIFLSRLP IFSSYNAQSE ERRIIIRSFG INSIKLPKDR IHSEKSNKSV AMDMLNEVKR  300
CPDELFTTLS AEKQSRFRII SDDHNEVLMK RSSDRFVPLL LQYIDYGKLF DHIRFHVNMG  360
KLRYLLKADK TCIDGQTRVR VIEQPLNGFG RLEEAETMRK QENGTFGNSG IRIRDFENMK  420
RDDANPANYP YIVDTYTHYI LENNKVEMFI NDKEDSAPLL PVIEDDRYVV KTIPSCRMST  480
LEIPAMAFHM FLFGSKKTEK LIVDVHNRYK RLFQAMQKEE VTAENIASFG IAESDLPQKI  540
LDLISGNAHG                                                         550

SEQ ID NO: 10          moltype = AA  length = 1749
FEATURE                Location/Qualifiers
REGION                 1..1749
                       note = C551 Fragment amino acid sequence
source                 1..1749
                       mol_type = protein
                       organism = synthetic construct
SEQUENCE: 10
LYSASPVALA SPALAPHEIL EARGLEUTHR VALASPASPM ETLEUTHRAS PTHRGLUARG  60
```

-continued

ARGILELYSA RGPHELYSAS PASPARGLYS SERILEARGS ERALAASPAS NLYSMETGLY 120
LYSARGGLYP HELYSGLNIL ESERTHRGLY LYSLEUALAA SPPHELEUAL ALYSASPILE 180
VALLEUPHEG LNPROSERVA LASNASPGLY GLUASNLYSI LETHRGLYLE UASNTYRARG 240
ILEMETGLNS ERALAILEAL AVALTYRASP SERGLYASPA SPTYRGLUAL ALYSGLNGLN 300
PHELYSLEUM ETPHEGLULY SALAARGLEU ILEGLYLYSG LYTHRTHRGL UPROHISPRO 360
PHELEUTYRL YSVALPHEAL AARGSERILE PROALAASNA LAVALGLUPH ETYRGLUARG 420
TYRLEUILEG LUARGLYSPH ETYRLEUTHR GLYLEUSERA SNGLUILELY SLYSGLYASN 480
ARGVALASPV ALPROPHEIL EARGARGASP GLNASNLYST RPLYSTHRPR OALAMETLYS 540
THRLEUGLYA RGILETYRSE RGLUASPLEU PROVALGLUL EUPROARGGL NMETPHEASP 600
ASNGLUILEL YSSERHISLE ULYSSERLEU PROGLNMETG LUGLYILEAS PPHEASNASN 660
ALAASNVALT HRTYRLEUIL EALAGLUTYR METLYSARGV ALLEUASPAS PASPPHEGLN 720
THRPHETYRG LNTRPASNAR GASNTYRARG TYRMETASPM ETLEULYSGL YGLUTYRASP 780
ARGLYSGLYS ERLEUGLNHI SCYSPHETHR SERVALGLUG LUARGGLUGL YLEUTRPLYS 840
GLUARGALAS ERARGTHRGL UARGTYRARG LYSGLNALAS ERASNLYSIL EARGSERASN 900
ARGGLNMETA RGASNALASE RSERGLUGLU ILEGLUTHRI LELEUASPLY SARGLEUSER 960
ASNSERARGA SNGLUTYRGL NLYSSERGLU LYSVALILEA RGARGTYRAR GVALGLNASP 1020
ALALEULEUP HELEULEUAL ALYSLYSTHR LEUTHRGLUL EUALAASPPH EASPGLYGLU 1080
ARGPHELYSL EULYSGLUIL EMETPROASP ALAGLULYSG LYILELEUSE RGLUILEMET 1140
PROMETSERP HETHRPHEGL ULYSGLYGLY LYSLYSTYRT HRILETHRSE RGLUGLYMET 1200
LYSLEULYSA SNTYRGLYAS PPHEPHEVAL LEUALASERA SPLYSARGIL EGLYASNLEU 1260
LEUGLULEUV ALGLYSERAS PILEVALSER LYSGLUASPI LEMETGLUGL UPHEASNLYS 1320
TYRASPGLNC YSARGPROGL UILESERSER ILEVALPHEA SNLEUGLULY STRPALAPHE 1380
ASPTHRTYRP ROGLULEUSE RALAARGVAL ASPARGGLUG LULYSVALAS PPHELYSSER 1440
ILELEULYSI LELEULEUAS NASNLYSASN ILEASNLYSG LUGLNSERAS PILELEUARG 1500
LYSILEARGA SNALAPHEAS PHISASNASN TYRPROASPL YSGLYVALVA LGLUILELYS 1560
ALALEUPROG LUILEALAME TSERILELYS LYSALAPHEG LYGLUTYRAL AILEMETLYS 1620
GLYSERLEUG LNLEUPROPR OLEUGLUARG LEUTHRLEUG LYSERSERTY RPROTYRASP 1680
VALPROASPT YRALATYRPR OTYRASPVAL PROASPTYRA LATYRPROTY RASPVALPRO 1740
ASPTYRALA 1749

SEQ ID NO: 11 moltype = AA length = 624
FEATURE Location/Qualifiers
REGION 1..624
note = N624 Fragment amino acid sequence
source 1..624
mol_type = protein
organism = synthetic construct
SEQUENCE: 11
MNIPALVENQ KKYFGTYSVM AMLNAQTVLD HIQKVADIEG EQNENNENLW FHPVMSHLYN 60
AKNGYDKQPE KTMFIIERLQ SYFPFLKIMA ENQREYSNGK YKQNRVEVNS NDIFEVLKRA 120
FGVLKMYRDL TNHYKTYEEK LNDGCEFLTS TEQPLSGMIN NYYTVALRNM NERYGYKTED 180
LAFIQDKRFK FVKDAYGKKK SQVNTGFFLS LQDYNGDTQK KLHLSGVGIA LLICLFLDKQ 240
YINIFLSRLP IFSSYNAQSE ERRIIIRSFG INSIKLPKDR IHSEKSNKSV AMDMLNEVKR 300
CPDELFTTLS AEKQSRFRII SDDHNEVLMK RSSDRFVPLL LQYIDYGKLF DHIRFHVNMG 360
KLRYLLKADK TCIDGQTRVR VIEQPLNGFG RLEEAETMRK QENGTFGNSG IRIRDFENMK 420
RDDANPANYP YIVDTYTHYI LENNKVEMFI NDKEDSAPLL PVIEDDRYVV KTIPSCRMST 480
LEIPAMAFHM FLFGSKKTEK LIVDVHNRYK RLFQAMQKEE VTAENIASFG IAESDLPQKI 540
LDLISGNAHG KDVDAFIRLT VDDMLTDTER RIKRFKDDRK SIRSADNKMG KRGFKQISTG 600
KLADFLAKDI VLFQPSVNDG ENKI 624

SEQ ID NO: 12 moltype = AA length = 1527
FEATURE Location/Qualifiers
REGION 1..1527
note = C625 Fragment amino acid sequence
source 1..1527
mol_type = protein
organism = synthetic construct
SEQUENCE: 12
THRGLYLEUA SNTYRARGIL EMETGLNSER ALAILEALAV ALTYRASPSE RGLYASPASP 60
TYRGLUALAL YSGLNGLNPH ELYSLEUMET PHEGLULYSA LAARGLEUIL EGLYLYSGLY 120
THRTHRGLUP ROHISPROPH ELEUTYRLYS VALPHEALAA RGSERILEPR OALAASNALA 180
VALGLUPHET YRGLUARGTY RLEUILEGLU ARGLYSPHET YRLEUTHRGL YLEUSERASN 240
GLUILELYSL YSGLYASNAR GVALASPVAL PROPHEILEA RGARGASPGL NASNLYSTRP 300
LYSTHRPROA LAMETLYSTH RLEUGLYARG ILETYRSERG LUASPLEUPR OVALGLULEU 360
PROARGGLNM ETPHEASPAS NGLUILELYS SERHISLEUL YSSERLEUPR OGLNMETGLU 420
GLYILEASPP HEASNASNAL AASNVALTHR TYRLEUILEA LAGLUTYRME TLYSARGVAL 480
LEUASPASPA SPPHEGLNTH RPHETYRGLN TRPASNARGA SNTYRARGTY RMETASPMET 540
LEULYSGLYG LUTYRASPAR GLYSGLYSER LEUGLNHISC YSPHETHRSE RVALGLUGLU 600
ARGGLUGLYL EUTRPLYSGL UARGALASER ARGTHRGLUA RGTYRARGLY SGLNALASER 660
ASNLYSILEA RGSERASNAR GGLNMETARG ASNALASERS ERGLUGLUIL EGLUTHRILE 720
LEUASPLYSA RGLEUSERAS NSERARGASN GLUTYRGLNL YSSERGLULY SVALILEARG 780
ARGTYRARGV ALGLNASPAL ALEULEUPHE LEULEUALAL YSLYSTHRLE UTHRGLULEU 840
ALAASPPHEA SPGLYGLUAR GPHELYSLEU LYSGLUILEM ETPROASPAL AGLULYSGLY 900
ILELEUSERG LUILEMETPR OMETSERPHE THRPHEGLUL YSGLYGLYLY SLYSTYRTHR 960
ILETHRSERG LUGLYMETLY SLEULYSASN TYRGLYASPP HEPHEVALLE UALASERASP 1020
LYSARGILEG LYASNLEULE UGLULEUVAL GLYSERASPI LEVALSERLY SGLUASPILE 1080
METGLUGLUP HEASNLYSTY RASPGLNCYS ARGPROGLUI LESERSERIL EVALPHEASN 1140
LEUGLULYST RPALAPHEAS PTHRTYRPRO GLULEUSERA LAARGVALAS PARGGLUGLU 1200
LYSVALASPP HELYSSERIL ELEULYSILE LEULEUASNA SNLYSASNIL EASNLYSGLU 1260

```
GLNSERASPI LELEUARGLY SILEARGASN ALAPHEASPH ISASNASNTY RPROASPLYS  1320
GLYVALVALG LUILELYSAL ALEUPROGLU ILEALAMETS ERILELYSLY SALAPHEGLY  1380
GLUTYRALAI LEMETLYSGL YSERLEUGLN LEUPROPROL EUGLUARGLE UTHRLEUGLY  1440
SERSERTYRP ROTYRASPVA LPROASPTYR ALATYRPROT YRASPVALPR OASPTYRALA  1500
TYRPROTYRA SPVALPROAS PTYRALA                                      1527

SEQ ID NO: 13          moltype = AA  length = 725
FEATURE                Location/Qualifiers
REGION                 1..725
                       note = N725 Fragment amino acid sequence
source                 1..725
                       mol_type = protein
                       organism = synthetic construct
SEQUENCE: 13
MNIPALVENQ KKYFGTYSVM AMLNAQTVLD HIQKVADIEG EQNENNENLW FHPVMSHLYN  60
AKNGYDKQPE KTMFIIERLQ SYFPFLKIMA ENQREYSNGK YKQNRVEVNS NDIFEVLKRA  120
FGVLKMYRDL TNHYKTYEEK LNDGCEFLTS TEQPLSGMIN NYYTVALRNM NERYGYKTED  180
LAFIQDKRFK FVKDAYGKKK SQVNTGFFLS LQDYNGDTQK KLHLSGVGIA LLICLFLDKQ  240
YINIFLSRLP IFSSYNAQSE ERRIIIRSFG INSIKLPKDR IHSEKSNKSV AMDMLNEVKR  300
CPDELFTTLS AEKQSRFRII SDDHNEVLMK RSSDRFVPLL LQYIDYGKLF DHIRFHVNMG  360
KLRYLLKADK TCIDGQTRVR VIEQPLNGFG RLEEAETMRK QENGTFGNSG IRIRDFENMK  420
RDDANPANYP YIVDTYTHYI LENNKVEMFI NDKEDSAPLL PVIEDDRYVV KTIPSCRMST  480
LEIPAMAFHM FLFGSKKTEK LIVDVHNRYK RLFQAMQKEE VTAENIASFG IAESDLPQKI  540
LDLISGNAHG KDVDAFIRLT VDDMLTDTER RIKRFKDDRK SIRSADNKMG KRGFKQISTG  600
KLADFLAKDI VLFQPSVNDG ENKITGLNYR IMQSAIAVYD SGDDYEAKQQ FKLMFEKARL  660
IGKGTTEPHP FLYKVFARSI PANAVEFYER YLIERKFYLT GLSNEIKKGN RVDVPFIRRD  720
QNKWK                                                              725

SEQ ID NO: 14          moltype = AA  length = 1224
FEATURE                Location/Qualifiers
REGION                 1..1224
                       note = C726 Fragment amino acid sequence
source                 1..1224
                       mol_type = protein
                       organism = synthetic construct
SEQUENCE: 14
THRPROALAM ETLYSTHRLE UGLYARGILE TYRSERGLUA SPLEUPROVA LGLULEUPRO  60
ARGGLNMETP HEASPASNGL UILELYSSER HISLEULYSS ERLEUPROGL NMETGLUGLY  120
ILEASPPHEA SNASNALAAS NVALTHRTYR LEUILEALAG LUTYRMETLY SARGVALLEU  180
ASPASPASPP HEGLNTHRPH ETYRGLNTRP ASNARGASNT YRARGTYRME TASPMETLEU  240
LYSGLYGLUT YRASPARGLY SGLYSERLEU GLNHISCYSP HETHRSERVA LGLUGLUARG  300
GLUGLYLEUT RPLYSGLUAR GALASERARG THRGLUARGT YRARGLYSGL NALASERASN  360
LYSILEARGS ERASNARGGL NMETARGASN ALASERSERG LUGLUILEGL UTHRILELEU  420
ASPLYSARGL EUSERASNSE RARGASNGLU TYRGLNLYSS ERGLULYSVA LILEARGARG  480
TYRARGVALG LNASPALALE ULEUPHELEU LEUALALYSL YSTHRLEUTH RGLULEUALA  540
ASPPHEASPG LYGLUARGPH ELYSLEULYS GLUILEMETP ROASPALAGL ULYSGLYILE  600
LEUSERGLUI LEMETPROME TSERPHETHR PHEGLULYSG LYGLYLYSLY STYRTHRILE  660
THRSERGLUG LYMETLYSLE ULYSASNTYR GLYASPPHEP HEVALLEUAL ASERASPLYS  720
ARGILEGLYA SNLEULEUGL ULEUVALGLY SERASPILEV ALSERLYSGL UASPILEMET  780
GLUGLUPHEA SNLYSTYRAS PGLNCYSARG PROGLUILES ERSERILEVA LPHEASNLEU  840
GLULYSTRPA LAPHEASPTH RTYRPROGLU LEUSERALAA RGVALASPAR GGLUGLULYS  900
VALASPPHEL YSSERILELE ULYSILELEU LEUASNASNL YSASNILEAS NLYSGLUGLN  960
SERASPILEL EUARGLYSIL EARGASNALA PHEASPHISA SNASNTYRPR OASPLYSGLY  1020
VALVALGLUI LELYSALALE UPROGLUILE ALAMETSERI LELYSLYSAL APHEGLYGLU  1080
TYRALAILEM ETLYSGLYSE RLEUGLNLEU PROPROLEUG LUARGLEUTH RLEUGLYSER  1140
SERTYRPROT YRASPVALPR OASPTYRALA TYRPROTYRA SPVALPROAS PTYRALATYR  1200
PROTYRASPV ALPROASPTY RALA                                         1224

SEQ ID NO: 15          moltype = AA  length = 928
FEATURE                Location/Qualifiers
REGION                 1..928
                       note = N928 Fragment amino acid sequence
source                 1..928
                       mol_type = protein
                       organism = synthetic construct
SEQUENCE: 15
MNIPALVENQ KKYFGTYSVM AMLNAQTVLD HIQKVADIEG EQNENNENLW FHPVMSHLYN  60
AKNGYDKQPE KTMFIIERLQ SYFPFLKIMA ENQREYSNGK YKQNRVEVNS NDIFEVLKRA  120
FGVLKMYRDL TNHYKTYEEK LNDGCEFLTS TEQPLSGMIN NYYTVALRNM NERYGYKTED  180
LAFIQDKRFK FVKDAYGKKK SQVNTGFFLS LQDYNGDTQK KLHLSGVGIA LLICLFLDKQ  240
YINIFLSRLP IFSSYNAQSE ERRIIIRSFG INSIKLPKDR IHSEKSNKSV AMDMLNEVKR  300
CPDELFTTLS AEKQSRFRII SDDHNEVLMK RSSDRFVPLL LQYIDYGKLF DHIRFHVNMG  360
KLRYLLKADK TCIDGQTRVR VIEQPLNGFG RLEEAETMRK QENGTFGNSG IRIRDFENMK  420
RDDANPANYP YIVDTYTHYI LENNKVEMFI NDKEDSAPLL PVIEDDRYVV KTIPSCRMST  480
LEIPAMAFHM FLFGSKKTEK LIVDVHNRYK RLFQAMQKEE VTAENIASFG IAESDLPQKI  540
LDLISGNAHG KDVDAFIRLT VDDMLTDTER RIKRFKDDRK SIRSADNKMG KRGFKQISTG  600
KLADFLAKDI VLFQPSVNDG ENKITGLNYR IMQSAIAVYD SGDDYEAKQQ FKLMFEKARL  660
IGKGTTEPHP FLYKVFARSI PANAVEFYER YLIERKFYLT GLSNEIKKGN RVDVPFIRRD  720
QNKWKTPAMK TLGRIYSEDL PVELPRQMFD NEIKSHLKSL PQMEGIDFNN ANVTYLIAEY  780
```

```
MKRVLDDDFQ TFYQWNRNYR YMDMLKGEYD RKGSLQHCFT SVEEREGLWK ERASRTERYR  840
KQASNKIRSN RQMRNASSEE IETILDKRLS NSRNEYQKSE KVIRRYRVQD ALLFLLAKKT  900
LTELADFDGE RFKLKEIMPD AEKGILSE                                     928

SEQ ID NO: 16          moltype = AA  length = 615
FEATURE                Location/Qualifiers
REGION                 1..615
                       note = C929 Fragment amino acid sequence
source                 1..615
                       mol_type = protein
                       organism = synthetic construct
SEQUENCE: 16
ILEMETPROM ETSERPHETH RPHEGLULYS GLYGLYLYSL YSTYRTHRIL ETHRSERGLU  60
GLYMETLYSL EULYSASNTY RGLYASPPHE PHEVALLEUA LASERASPLY SARGILEGLY  120
ASNLEULEUG LULEUVALGL YSERASPILE VALSERLYSG LUASPILEME TGLUGLUPHE  180
ASNLYSTYRA SPGLNCYSAR GPROGLUILE SERSERILEV ALPHEASNLE UGLULYSTRP  240
ALAPHEASPT HRTYRPROGL ULEUSERALA ARGVALASPA RGGLUGLULY SVALASPPHE  300
LYSSERILEL EULYSILELE ULEUASNASN LYSASNILEA SNLYSGLUGL NSERASPILE  360
LEUARGLYSI LEARGASNAL APHEASPHIS ASNASNTYRP ROASPLYSGL YVALVALGLU  420
ILELYSALAL EUPROGLUIL EALAMETSER ILELYSLYSA LAPHEGLYGL UTYRALAILE  480
METLYSGLYS ERLEUGLNLE UPROPROLEU GLUARGLEUT HRLEUGLYSE RSERTYRPRO  540
TYRASPVALP ROASPTYRAL ATYRPROTYR ASPVALPROA SPTYRALATY RPROTYRASP  600
VALPROASPT YRALA                                                   615

SEQ ID NO: 17          moltype = AA  length = 93
FEATURE                Location/Qualifiers
REGION                 1..93
                       note = FRB amino acid sequence
source                 1..93
                       mol_type = protein
                       organism = synthetic construct
SEQUENCE: 17
ILWHEMWHEG LEEASRLYFG ERNVKGMFEV LEPLHAMMER GPQTLKETSF NQAYGRDLME  60
AQEWCRKYMK SGNVKDLTQA WDLYYHVFRR ISK                               93

SEQ ID NO: 18          moltype = AA  length = 107
FEATURE                Location/Qualifiers
REGION                 1..107
                       note = FKBP amino acid sequence
source                 1..107
                       mol_type = protein
                       organism = synthetic construct
SEQUENCE: 18
GVQVETISPG DGRTFPKRGQ TCVVHYTGML EDGKKFDSSR DRNKPFKFML GKQEVIRGWE  60
EGVAQMSVGQ RAKLTISPDY AYGATGHPGI IPPHATLVFD VELLKLE                107

SEQ ID NO: 19          moltype = AA  length = 150
FEATURE                Location/Qualifiers
REGION                 1..150
                       note = nMag amino acid sequence
source                 1..150
                       mol_type = protein
                       organism = synthetic construct
SEQUENCE: 19
HTLYAPGGYD IMGYLDQIGN RPNPQVELGP VDTSCALILC DLKQKDTPIV YASEAFLYMT  60
GYSNAEVLGR NCRFLQSPDG MVKPKSTRKY VDSNTINTMR KAIDRNAEVQ VEVVNFKKNG  120
QRFVNFLTMI PVRDETGEYR YSMGFQCETE                                   150

SEQ ID NO: 20          moltype = AA  length = 150
FEATURE                Location/Qualifiers
REGION                 1..150
                       note = pMag amino acid sequence
source                 1..150
                       mol_type = protein
                       organism = synthetic construct
SEQUENCE: 20
HTLYAPGGYD IMGYLRQIRN RPNPQVELGP VDTSCALILC DLKQKDTPIV YASEAFLYMT  60
GYSNAEVLGR NCRFLQSPDG MVKPKSTRKY VDSNTINTIR KAIDRNAEVQ VEVVNFKKNG  120
QRFVNFLTII PVRDETGEYR YSMGFQCETE                                   150

SEQ ID NO: 21          moltype = AA  length = 32
FEATURE                Location/Qualifiers
REGION                 1..32
                       note = linker
source                 1..32
                       mol_type = protein
                       organism = synthetic construct
SEQUENCE: 21
GSGSGSGSGS GSGSGSGSGS GSGSGSGSGS GS                                32
```

```
SEQ ID NO: 22           moltype = DNA  length = 816
FEATURE                 Location/Qualifiers
misc_feature            1..816
                        note = N272 Fragment polynucleotide sequence
source                  1..816
                        mol_type = other DNA
                        organism = synthetic construct
SEQUENCE: 22
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaac                            816

SEQ ID NO: 23           moltype = DNA  length = 2586
FEATURE                 Location/Qualifiers
misc_feature            1..2586
                        note = C273 Fragment polynucleotide sequence
source                  1..2586
                        mol_type = other DNA
                        organism = synthetic construct
SEQUENCE: 23
agcatcaagc tgcccaagga ccggatccac agcgagaagt ccaacaagag cgtggccatg  60
gatatgctca acgaagtgaa gcggtgcccc gacgagctgt tcacaacact gtctgccgag  120
aagcagtccc ggttcagaat catcagcgac gaccacaatg aagtgctgat gaagcggagc  180
agcgacagat tcgtgcctct gctgctgcag tatatcgatt acggcaagct gttcgaccac  240
atcaggttcc acgtgaacat gggcaagctg agatacctgc tgaaggccga caagacctgc  300
atcgacggcc agaccagagt cagagtgatc gagcagcccc tgaacggctt cggcagactg  360
gaagaggccg agacaatgcg gaagcaagag aacggcacct tcggcaacag cggcatccgg  420
atcagagact tcgagaacat gaagcgggac gacgccaatc ctgccaacta tccctacatc  480
gtggacacct acacacacta catcctggaa aacaacaagg tcgagatgtt tatcaacgac  540
aaagaggaca gcgccccact gctgcccgtg atcgaggatg atagatacgt ggtcaagaca  600
atccccagct gccggatgag caccctggaa attccagcca tggccttcca catgtttctg  660
ttcggcagca agaaaaccga gaagctgatc gtggacgtgc acaaccggta caagagactg  720
ttccaggcca tgcagaaaga agaagtgacc gccgagaata tcgccagctt cggaatcgcc  780
gagagcgacc tgcctcagaa gatcctggat ctgatcagcg gcaatgccca cggcaaggat  840
gtggacgcct tcatcagact gaccgtggac gacatgctga ccgacaccga gcggagaatc  900
aagagattca aggacgaccg gaagtccatt cggagcgccg acaacaagat gggaaagaga  960
ggcttcaagc agatctccac aggcaagctg gccgacttcc tggccaagga catcgtgctg  1020
tttcagccca gcgtgaacga tggcgagaac aagatcaccg gcctgaacta ccggatcatg  1080
cagagcgcca ttgccgtgta cgatagcggc gacgattacg aggccaagca gcagttcaag  1140
ctgatgttcg agaaggcccg gctgatcggc aagggcacaa cagagcctca tccatttctg  1200
tacaaggtgt tcgcccgcag catccccgcc aatgccgtcg agttctacga gcgctacctg  1260
atcgagcgga agttctacct gaccggcctg tccaacgaga tcaagaaagg caacagagtg  1320
gatgtgccct tcatccggcg ggaccagaac aagtggaaaa caccccgccat gaagaccctg  1380
ggcagaatct acagcgagga tctgcccgtg gaactgccca gacagatgtt cgacaatgag  1440
atcaagtccc acctgaagtc cctgccacag atggaaggca tcgacttcaa caatgccaac  1500
gtgacctatc tgatcgccga gtacatgaag agagtgctgg acgacgactt ccagaccttc  1560
taccagtgga accgcaacta ccggtacatg gacatgctta agggcgagta cgacagaaag  1620
ggctccctgc agcactgctt caccagcgtg gaagagagag aaggcctctg gaaagagcgg  1680
gcctccagaa cagagcggta cagaaagcag gccagcaaca agatccgcag caaccggcag  1740
atgagaaacg ccagcagcga agagatcgag acaatcctgg ataagcggct gagcaacagc  1800
cggaacgagt accagaaaag cgagaaagtg atccggcgct acagagtgca ggatgccctg  1860
ctgtttctgc tggccaaaaa gaccctgacc gaactggccg atttcgacgg cgagaggttc  1920
aaactgaaag aaatcatgcc cgacgccgag aagggaatcc tgagcgagat catgcccatg  1980
agcttcacct tcgagaaagg cggcaagaag tacaccatca ccagcgaggg catgaagctg  2040
aagaactacg gcgacttctt tgtgctggct agcgacaaga ggatcggcaa cctgctggaa  2100
ctcgtgggca gcgacatcgt gtccaaagag gatatcatgg aagagttcaa caaatacgac  2160
cagtgcaggc ccgagatcag ctccatcgtg ttcaacctgg aaaagtgggc cttcgacaca  2220
taccccgagc tgtctgccag agtggaccgg gaagagaagg tggacttcaa gagcatcctg  2280
aaaatcctgc tgaacaacaa gaacatcaac aaagagcaga gcgacatcct gcggaagatc  2340
cggaacgcct tcgatcacaa caattacccc gacaaaggcg tggtggaaat caaggccctg  2400
cctgagatcg ccatgagcat caagaaggcc tttggggagt acgccatcat gaagggatcc  2460
cttcaactgc ctccacttga aagactgaca ctgggtagtt cctacccata cgatgttcca  2520
gattacgctt atccctacga cgtgcctgat tatgcatacc catatgatgt ccccgactat  2580
gcctaa                                                            2586

SEQ ID NO: 24           moltype = DNA  length = 858
FEATURE                 Location/Qualifiers
```

```
misc_feature            1..858
                        note = N286 Fragment polynucleotide sequence
source                  1..858
                        mol_type = other DNA
                        organism = synthetic construct
SEQUENCE: 24
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtcc                                                 858

SEQ ID NO: 25           moltype = DNA  length = 2544
FEATURE                 Location/Qualifiers
misc_feature            1..2544
                        note = C287 Fragment polynucleotide sequence
source                  1..2544
                        mol_type = other DNA
                        organism = synthetic construct
SEQUENCE: 25
aacaagagcg tggccatgga tatgctcaac gaagtgaagc ggtgccccga cgagctgttc  60
acaacactgt ctgccgagaa gcagtcccgg ttcagaatca tcagcgacga ccacaatgaa  120
gtgctgatga agcggagcag cgacagattc gtgcctctgc tgctgcagta tatcgattac  180
ggcaagctgt tcgaccacat caggttccac gtgaacatgg gcaagctgag atacctgctg  240
aaggccgaca agacctgcat cgacggccag accagagtca gagtgatcga gcagcccctg  300
aacggcttcg gcagactgga agaggccgag acaatgcgga agcaagagaa cggcaccttc  360
ggcaacagcg gcatccggat cagagacttc gagaacatga agcgggacga cgccaatcct  420
gccaactatc cctacatcgt ggacacctac acacactaca tcctggaaaa caacaaggtc  480
gagatgttta tcaacgacaa agaggacagc gccccactgc tgcccgtgat cgaggatgat  540
agatacgtgg tcaagacaat ccccagctgc cggatgagca ccctggaaat tccagccatg  600
gccttccaca tgtttctgtt cggcagcaag aaaaccgaga agctgatcgt ggacgtgcac  660
aaccggtaca agagactgtt ccaggccatg cagaaagaag aagtgaccgc cgagaatatc  720
gccagcttcg gaatcgccga gagcgacctg cctcagaaga tcctggatct gatcagcggc  780
aatgcccacg gcaaggatgt ggacgccttc atcagactga ccgtggacga catgctgacc  840
gacaccgagc ggagaatcaa gagattcaag gacgaccgga agtccattcg gagcgccgac  900
aacaagatgg gaaagagagg cttcaagcag atctccacag gcaagctggc cgacttcctg  960
gccaaggaca tcgtgctgtt tcagcccagc gtgaacgatg gcgagaacaa gatcaccggc  1020
ctgaactacc ggatcatgca gagcgccatt gccgtgtacg atagcggcga cgattacgag  1080
gccaagcagc agttcaagct gatgttcgag aaggcccggc tgatcggcaa gggcacaaca  1140
gagcctcatc catttctgta caaggtgttc gcccgcagca tccccgccaa tgccgtcgag  1200
ttctacgagc gctacctgat cgagcggaag ttctacctga ccggcctgtc caacgagatc  1260
aagaaaggca acagagtgga tgtgcccttc atccggcggg accagaacaa gtggaaaaca  1320
cccgccatga agaccctggg cagaatctac agcgaggatc tgcccgtgga actgcccaga  1380
cagatgttcg acaatgagat caagtcccac ctgaagtccc tgccacagat ggaaggcatc  1440
gacttcaaca atgccaacgt gacctatctg atcgccgagt acatgaagag agtgctggac  1500
gacgacttcc agaccttcta ccagtggaac cgcaactacc ggtacatgga catgcttaag  1560
ggcgagtacg acagaaaggg ctccctgcag cactgcttca ccagcgtgga agagagagaa  1620
ggcctctgga aagagcgggc ctccagaaca gagcggtaca gaaagcaggc cagcaacaag  1680
atccgcagca accggcagat gagaaacgcc agcagcgaag agatcgagac aatcctggat  1740
aagcggctga gcaacagccg gaacgagtac cagaaaagcg agaaagtgat ccggcgctac  1800
agagtgcagg atgccctgct gtttctgctg gccaaaaaga ccctgaccga actggccgat  1860
ttcgacggcg agaggttcaa actgaaagaa atcatgcccg acgccgagaa gggaatcctg  1920
agcgagatca tgcccatgag cttcaccttc gagaaaggcg gcaagaagta caccatcacc  1980
agcgagggca tgaagctgaa gaactacggc gacttctttg tgctggctag cgacaagagg  2040
atcggcaacc tgctggaact cgtgggcagc gacatcgtgt ccaaagagga tatcatggaa  2100
gagttcaaca aatacgacca gtgcaggccc gagatcagct ccatcgtgtt caacctggaa  2160
aagtgggcct tcgacacata ccccgagctg tctgccagag tggaccggga agagaaggtg  2220
gacttcaaga gcatcctgaa aatcctgctg aacaacaaga acatcaacaa agagcagagc  2280
gacatcctgc ggaagatccg gaacgccttc gatcacaaca attaccccga caaaggcgtg  2340
gtggaaatca aggccctgcc tgagatcgcc atgagcatca agaaggcctt tggggagtac  2400
gccatcatga agggatccct tcaactgcct ccacttgaaa gactgacact gggtagttcc  2460
tacccatacg atgttccaga ttacgcttat ccctacgacg tgcctgatta tgcataccca  2520
tatgatgtcc ccgactatgc ctaa                                          2544

SEQ ID NO: 26           moltype = DNA  length = 1053
FEATURE                 Location/Qualifiers
misc_feature            1..1053
                        note = N351 Fragment polynucleotide sequence
source                  1..1053
```

```
                        mol_type = other DNA
                        organism = synthetic construct
SEQUENCE: 26
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gac                               1053

SEQ ID NO: 27           moltype = DNA  length = 2349
FEATURE                 Location/Qualifiers
misc_feature            1..2349
                        note = C352 Fragment polynucleotide sequence
source                  1..2349
                        mol_type = other DNA
                        organism = synthetic construct
SEQUENCE: 27
cacatcaggt tccacgtgaa catgggcaag ctgagatacc tgctgaaggc cgacaagacc  60
tgcatcgacg gccagaccag agtcagagtg atcgagcagc ccctgaacgg cttcggcaga  120
ctggaagagg ccgagacaat gcggaagcaa gagaacggca ccttcggcaa cagcggcatc  180
cggatcagag acttcgagaa catgaagcgg gacgacgcca atcctgccaa ctatccctac  240
atcgtggaca cctacacaca ctacatcctg gaaaacaaca aggtcgagat gtttatcaac  300
gacaaagagg acagcgcccc actgctgccc gtgatcgagg atgatagata cgtggtcaag  360
acaatcccca gctgccggat gagcaccctg gaaattccag ccatggcctt ccacatgttt  420
ctgttcggca gcaagaaaac cgagaagctg atcgtggacg tgcacaaccg gtacaagaga  480
ctgttccagg ccatgcagaa agaagaagtg accgccgaga atatcgccag cttcggaatc  540
gccgagagcg acctgcctca gaagatcctg gatctgatca gcggcaatgc ccacggcaag  600
gatgtggacg ccttcatcag actgaccgtg gacgacatgc tgaccgacac cgagcggaga  660
atcaagagat tcaaggacga ccggaagtcc attcggagcg ccgacaacaa gatgggaaag  720
agaggcttca agcagatctc cacaggcaag ctggccgact tcctggccaa ggacatcgtg  780
ctgtttcagc ccagcgtgaa cgatggcgag aacaagatca ccggcctgaa ctaccggatc  840
atgcagagcg ccattgccgt gtacgatagc ggcgacgatt acgaggccaa gcagcagttc  900
aagctgatgt tcgagaaggc ccggctgatc ggcaagggca caacagagcc tcatccattt  960
ctgtacaagg tgttcgcccg cagcatcccc gccaatgccg tcgagttcta cgagcgctac  1020
ctgatcgagc ggaagttcta cctgaccggc ctgtccaacg agatcaagaa aggcaacaga  1080
gtggatgtgc ccttcatccg gcgggaccag aacaagtgga aaacacccgc catgaagacc  1140
ctgggcagaa tctacagcga ggatctgccc gtggaactgc ccagacagat gttcgacaat  1200
gagatcaagt cccacctgaa gtccctgcca cagatggaag gcatcgactt caacaatgcc  1260
aacgtgacct atctgatcgc cgagtacatg aagagagtgc tggacgacga cttccagacc  1320
ttctaccagt ggaaccgcaa ctaccggtac atggacatgc ttaagggcga gtacgacaga  1380
aagggctccc tgcagcactg cttcaccagc gtggaagaga gagaaggcct ctggaaagag  1440
cgggcctcca gaacagagcg gtacagaaag caggccagca acaagatccg cagcaaccgg  1500
cagatgagaa acgccagcag cgaagagatc gagacaatcc tggataagcg gctgagcaac  1560
agccggaacg agtaccagaa aagcgagaaa gtgatccggc gctacagagt gcaggatgcc  1620
ctgctgtttc tgctggccaa aaagaccctg accgaactgg ccgatttcga cggcgagagg  1680
ttcaaactga aagaaatcat gcccgacgcc gagaagggaa tcctgagcga gatcatgccc  1740
atgagcttca ccttcgagaa aggcggcaag aagtacacca tcaccagcga gggcatgaag  1800
ctgaagaact acggcgactt ctttgtgctg gctagcgaca agaggatcgg caacctgctg  1860
gaactcgtgg gcagcgacat cgtgtccaaa gaggatatca tggaagagtt caacaaatac  1920
gaccagtgca ggcccgagat cagctccatc gtgttcaacc tggaaaagtg ggccttcgac  1980
acatacccccg agctgtctgc cagagtggac cgggaagaga aggtggactt caagagcatc  2040
ctgaaaatcc tgctgaacaa caagaacatc aacaaagagc agagcgacat cctgcggaag  2100
atccggaacg ccttcgatca caacaattac cccgacaaag gcgtggtgga aatcaaggcc  2160
ctgcctgaga tcgccatgag catcaagaag gcctttgggg agtacgccat catgaaggga  2220
tcccttcaac tgcctccact tgaaagactg acactgggta gttcctaccc atacgatgtt  2280
ccagattacg cttatcccta cgacgtgcct gattatgcat acccatatga tgtccccgac  2340
tatgcctaa                                                          2349

SEQ ID NO: 28           moltype = DNA  length = 1440
FEATURE                 Location/Qualifiers
misc_feature            1..1440
                        note = N480 Fragment polynucleotide sequence
source                  1..1440
                        mol_type = other DNA
                        organism = synthetic construct
SEQUENCE: 28
```

-continued atgaacatcc ccgctctggt ggaaaaccag aagaagtact ttggcaccta cagcgtgatg 60
gccatgctga acgctcagac cgtgctggac cacatccaga aggtggccga tattgagggc 120
gagcagaacg agaacaacga gaatctgtgg tttcaccccg tgatgagcca cctgtacaac 180
gccaagaacg gctacgacaa gcagcccgag aaaaccatgt tcatcatcga gcggctgcag 240
agctacttcc cattcctgaa gatcatggcc gagaaccaga gagagtacag caacggcaag 300
tacaagcaga accgcgtgga agtgaacagc aacgacatct tcgaggtgct gaagcgcgcc 360
ttcggcgtgc tgaagatgta cagggacctg accaaccact acaagaccta cgaggaaaag 420
ctgaacgacg gctgcgagtt cctgaccagc acagagcaac ctctgagcgg catgatcaac 480
aactactaca cagtggccct gcggaacatg aacgagagat acggctacaa gacagaggac 540
ctggccttca tccaggacaa gcggttcaag ttcgtgaagg acgcctacgg caagaaaaag 600
tcccaagtga ataccggatt cttcctgagc ctgcaggact acaacggcga cacacagaag 660
aagctgcacc tgagcggagt gggaatcgcc ctgctgatct gcctgttcct ggacaagcag 720
tacatcaaca tctttctgag caggctgccc atcttctcca gctacaatgc ccagagcgag 780
gaacggcgga tcatcatcag atccttcggc atcaacagca tcaagctgcc caaggaccgg 840
atccacagcg agaagtccaa caagagcgtg gccatggata tgctcaacga agtgaagcgg 900
tgccccgacg agctgttcac aacactgtct gccgagaagc agtcccggtt cagaatcatc 960
agcgacgacc acaatgaagt gctgatgaag cggagcagcg acagattcgt gcctctgctg 1020
ctgcagtata tcgattacgg caagctgttc gaccacatca ggttccacgt gaacatgggc 1080
aagctgagat acctgctgaa ggccgacaag acctgcatcg acggccagac cagagtcaga 1140
gtgatcgagc agcccctgaa cggcttcggc agactggaag aggccgagac aatgcggaag 1200
caagagaacg gcaccttcgg caacagcggc atccggatca gagacttcga gaacatgaag 1260
cgggacgacg ccaatcctgc caactatccc tacatcgtgg acacctacac acactacatc 1320
ctggaaaaca acaaggtcga gatgtttatc aacgacaaag aggacagcgc cccactgctg 1380
cccgtgatcg aggatgatag atacgtggtc aagacaatcc ccagctgccg gatgagcacc 1440

SEQ ID NO: 29 moltype = DNA length = 1962
FEATURE Location/Qualifiers
misc_feature 1..1962
note = C481 Fragment polynucleotide sequence
source 1..1962
mol_type = other DNA
organism = synthetic construct
SEQUENCE: 29
ctggaaattc cagccatggc cttccacatg tttctgttcg gcagcaagaa aaccgagaag 60
ctgatcgtgg acgtgcacaa ccggtacaag agactgttcc aggccatgca gaaagaagaa 120
gtgaccgccg agaatatcgc cagcttcgga atcgccgaga gcgacctgcc tcagaagatc 180
ctggatctga tcagcggcaa tgcccacggc aaggatgtgg acgccttcat cagactgacc 240
gtggacgaca tgctgaccga caccgagcgg agaatcaaga gattcaagga cgaccggaag 300
tccattcgga gcgccgacaa caagatggga aagagaggct tcaagcagat ctccacaggc 360
aagctggccg acttcctggc caaggacatc gtgctgtttc agcccagcgt gaacgatggc 420
gagaacaaga tcaccggcct gaactaccgg atcatgcaga gcgccattgc cgtgtacgat 480
agcggcgacg attacgaggc caagcagcag ttcaagctga tgttcgagaa ggcccggctg 540
atcggcaagg gcacaacaga gcctcatcca tttctgtaca aggtgttcgc ccgcagcatc 600
cccgccaatg ccgtcgagtt ctacgagcgc tacctgatcg agcggaagtt ctacctgacc 660
ggcctgtcca acgagatcaa gaaaggcaac agagtggatg tgcccttcat ccggcgggac 720
cagaacaagt ggaaaacacc cgccatgaag accctgggca gaatctacag cgaggatctg 780
cccgtggaac tgcccagaca gatgttcgac aatgagatca agtcccacct gaagtccctg 840
ccacagatgg aaggcatcga cttcaacaat gccaacgtga cctatctgat cgccgagtac 900
atgaagagag tgctggacga cgacttccag accttctacc agtggaaccg caactaccgg 960
tacatggaca tgcttaaggg cgagtacgac agaaagggct ccctgcagca ctgcttcacc 1020
agcgtggaag agagagaagg cctctggaaa gagcgggcct ccagaacaga gcggtacaga 1080
aagcaggcca gcaacaagat ccgcagcaac cggcagatga gaaacgccag cagcgaagag 1140
atcgagacaa tcctggataa gcggctgagc aacagccgga acgagtacca gaaaagcgag 1200
aaagtgatcc ggcgctacag agtgcaggat gccctgctgt ttctgctggc caaaaagacc 1260
ctgaccgaac tggccgattt cgacggcgag aggttcaaac tgaaagaaat catgcccgac 1320
gccgagaagg gaatcctgag cgagatcatg cccatgagct tcaccttcga gaaaggcggc 1380
aagaagtaca ccatcaccag cgagggcatg aagctgaaga actacggcga cttctttgtg 1440
ctggctagcg acaagaggat cggcaacctg ctggaactcg tgggcagcga catcgtgtcc 1500
aaagaggata tcatggaaga gttcaacaaa tacgaccagt gcaggcccga gatcagctcc 1560
atcgtgttca acctggaaaa gtgggccttc gacacatacc ccgagctgtc tgccagagtg 1620
gaccgggaag agaaggtgga cttcaagagc atcctgaaaa tcctgctgaa caacaagaac 1680
atcaacaaag agcagagcga catcctgcgg aagatccgga acgccttcga tcacaacaat 1740
taccccgaca aaggcgtggt ggaaatcaag gccctgcctg agatcgccat gagcatcaag 1800
aaggcctttg gggagtacgc catcatgaag ggatcccttc aactgcctcc acttgaaaga 1860
ctgacactgg gtagttccta cccatacgat gttccagatt acgcttatcc ctacgacgtg 1920
cctgattatg catacccata tgatgtcccc gactatgcct aa 1962

SEQ ID NO: 30 moltype = DNA length = 1650
FEATURE Location/Qualifiers
misc_feature 1..1650
note = N550 Fragment polynucleotide sequence
source 1..1650
mol_type = other DNA
organism = synthetic construct
SEQUENCE: 30
atgaacatcc ccgctctggt ggaaaaccag aagaagtact ttggcaccta cagcgtgatg 60
gccatgctga acgctcagac cgtgctggac cacatccaga aggtggccga tattgagggc 120
gagcagaacg agaacaacga gaatctgtgg tttcaccccg tgatgagcca cctgtacaac 180
gccaagaacg gctacgacaa gcagcccgag aaaaccatgt tcatcatcga gcggctgcag 240

```
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccacatca ggttccacgt gaacatgggc  1080
aagctgagat acctgctgaa ggccgacaag acctgcatcg acggccagac cagagtcaga  1140
gtgatcgagc agcccctgaa cggcttcggc agactggaag aggccgagac aatgcggaag  1200
caagagaacg gcaccttcgg caacagcggc atccggatca gagacttcga gaacatgaag  1260
cgggacgacg ccaatcctgc caactatccc tacatcgtgg acacctacac acactacatc  1320
ctggaaaaca acaaggtcga gatgtttatc aacgacaaag aggacagcgc cccactgctg  1380
cccgtgatcg aggatgatag atacgtggtc aagacaatcc ccagctgccg gatgagcacc  1440
ctggaaattc cagccatggc cttccacatg tttctgttcg gcagcaagaa aaccgagaag  1500
ctgatcgtgg acgtgcacaa ccggtacaag agactgttcc aggccatgca gaaagaagaa  1560
gtgaccgccg agaatatcgc cagcttcgga atcgccgaga gcgacctgcc tcagaagatc  1620
ctggatctga tcagcggcaa tgcccacggc                                   1650

SEQ ID NO: 31          moltype = DNA  length = 1752
FEATURE                Location/Qualifiers
misc_feature           1..1752
                       note = C551 Fragment polynucleotide sequence
source                 1..1752
                       mol_type = other DNA
                       organism = synthetic construct
SEQUENCE: 31
aaggatgtgg acgccttcat cagactgacc gtggacgaca tgctgaccga caccgagcgg  60
agaatcaaga gattcaagga cgaccggaag tccattcgga gcgccgacaa caagatggga  120
aagagaggct tcaagcagat ctccacaggc aagctggccg acttcctggc caaggacatc  180
gtgctgtttc agcccagcgt gaacgatggc gagaacaaga tcaccggcct gaactaccgg  240
atcatgcaga gcgccattgc cgtgtacgat agcggcgacg attacgaggc caagcagcag  300
ttcaagctga tgttcgagaa ggcccggctg atcggcaagg gcacaacaga gcctcatcca  360
tttctgtaca aggtgttcgc ccgcagcatc cccgccaatg ccgtcgagtt ctacgagcgc  420
tacctgatcg agcggaagtt ctacctgacc ggcctgtcca acgagatcaa gaaaggcaac  480
agagtggatg tgcccttcat ccggcgggac cagaacaagt ggaaaacacc cgccatgaag  540
accctgggca gaatctacag cgaggatctg cccgtggaac tgcccagaca gatgttcgac  600
aatgagatca agtcccacct gaagtccctg ccacagatgg aaggcatcga cttcaacaat  660
gccaacgtga cctatctgat cgccgagtac atgaagagag tgctggacga cgacttccag  720
accttctacc agtggaaccg caactaccgg tacatggaca tgcttaaggg cgagtacgac  780
agaaagggct ccctgcagca ctgcttcacc agcgtggaag agagagaagg cctctggaaa  840
gagcgggcct ccagaacaga gcggtacaga aagcaggcca gcaacaagat ccgcagcaac  900
cggcagatga gaaacgccag cagcgaagag atcgagacaa tcctggataa gcggctgagc  960
aacagccgga acgagtacca gaaaagcgag aaagtgatcc ggcgctacag agtgcaggat  1020
gccctgctgt ttctgctggc caaaaagacc ctgaccgaac tggccgattt cgacggcgag  1080
aggttcaaac tgaaagaaat catgcccgac gccgagaagg gaatcctgag cgagatcatg  1140
cccatgagct tcaccttcga gaaaggcggc aagaagtaca ccatcaccag cgagggcatg  1200
aagctgaaga actacggcga cttctttgtg ctggctagcg acaagaggat cggcaacctg  1260
ctggaactcg tgggcagcga catcgtgtcc aaagaggata tcatggaaga gttcaacaaa  1320
tacgaccagt gcaggcccga gatcagctcc atcgtgttca acctggaaaa gtgggccttc  1380
gacacatacc ccgagctgtc tgccagagtg gaccgggaag agaaggtgga cttcaagagc  1440
atcctgaaaa tcctgctgaa caacaagaac atcaacaaag agcagagcga catcctgcgg  1500
aagatccgga acgccttcga tcacaacaat taccccgaca aaggcgtggt ggaaatcaag  1560
gccctgcctg agatcgccat gagcatcaag aaggcctttg gggagtacgc catcatgaag  1620
ggatcccttc aactgcctcc acttgaaaga ctgacactgg gtagttccta cccatacgat  1680
gttccagatt acgcttatcc ctacgacgtg cctgattatg catacccata tgatgtcccc  1740
gactatgcct aa                                                      1752

SEQ ID NO: 32          moltype = DNA  length = 1872
FEATURE                Location/Qualifiers
misc_feature           1..1872
                       note = N624 Fragment polynucleotide sequence
source                 1..1872
                       mol_type = other DNA
                       organism = synthetic construct
SEQUENCE: 32
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
```

```
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccacatca ggttccacgt gaacatgggc  1080
aagctgagat acctgctgaa ggccgacaag acctgcatcg acggccagac cagagtcaga  1140
gtgatcgagc agcccctgaa cggcttcggc agactggaag aggccgagac aatgcggaag  1200
caagagaacg gcaccttcgg caacagcggc atccggatca gagacttcga gaacatgaag  1260
cgggacgacg ccaatcctgc caactatccc tacatcgtgg acacctacac acactacatc  1320
ctggaaaaca acaaggtcga gatgtttatc aacgacaaag aggacagcgc cccactgctg  1380
cccgtgatcg aggatgatag atacgtggtc aagacaatcc ccagctgccg gatgagcacc  1440
ctggaaattc cagccatggc cttccacatg tttctgttcg gcagcaagaa aaccgagaag  1500
ctgatcgtgg acgtgcacaa ccggtacaag agactgttcc aggccatgca gaaagaagaa  1560
gtgaccgccg agaatatcgc cagcttcgga atcgccgaga gcgacctgcc tcagaagatc  1620
ctggatctga tcagcggcaa tgcccacggc aaggatgtgg acgccttcat cagactgacc  1680
gtggacgaca tgctgaccga caccgagcgg agaatcaaga gattcaagga cgaccggaag  1740
tccattcgga gcgccgacaa caagatggga aagagaggct tcaagcagat ctccacaggc  1800
aagctggccg acttcctggc caaggacatc gtgctgtttc agcccagcgt gaacgatggc  1860
gagaacaaga tc                                                      1872
```

```
SEQ ID NO: 33          moltype = DNA  length = 1530
FEATURE                Location/Qualifiers
misc_feature           1..1530
                       note = C625 Fragment polynucleotide sequence
source                 1..1530
                       mol_type = other DNA
                       organism = synthetic construct
SEQUENCE: 33
accggcctga actaccggat catgcagagc gccattgccg tgtacgatag cggcgacgat  60
tacgaggcca agcagcagtt caagctgatg ttcgagaagg cccggctgat cggcaagggc  120
acaacagagc ctcatccatt tctgtacaag gtgttcgccc gcagcatccc cgccaatgcc  180
gtcgagttct acgagcgcta cctgatcgag cggaagttct acctgaccgg cctgtccaac  240
gagatcaaga aaggcaacag agtggatgtg cccttcatcc ggcgggacca gaacaagtgg  300
aaaacacccg ccatgaagac cctgggcaga atctacagcg aggatctgcc cgtggaactg  360
cccagacaga tgttcgacaa tgagatcaag tcccacctga agtccctgcc acagatggaa  420
ggcatcgact tcaacaatgc caacgtgacc tatctgatcg ccgagtacat gaagagagtg  480
ctggacgacg acttccagac cttctaccag tggaaccgca actaccggta catggacatg  540
cttaagggcg agtacgacag aaagggctcc ctgcagcact gcttcaccag cgtggaagag  600
agagaaggcc tctggaaaga gcgggcctcc agaacagagc ggtacagaaa gcaggccagc  660
aacaagatcc gcagcaaccg gcagatgaga aacgccagca gcgaagagat cgagacaatc  720
ctggataagc ggctgagcaa cagccggaac gagtaccaga aaagcgagaa agtgatccgg  780
cgctacagag tgcaggatgc cctgctgttt ctgctggcca aaaagaccct gaccgaactg  840
gccgatttcg acggcgagag gttcaaactg aaagaaatca tgcccgacgc cgagaaggga  900
atcctgagcg agatcatgcc catgagcttc accttcgaga aaggcggcaa gaagtacacc  960
atcaccagcg agggcatgaa gctgaagaac tacggcgact tctttgtgct ggctagcgac  1020
aagaggatcg gcaacctgct ggaactcgtg ggcagcgaca tcgtgtccaa agaggatatc  1080
atggaagagt tcaacaaata cgaccagtgc aggcccgaga tcagctccat cgtgttcaac  1140
ctggaaaagt gggccttcga cacatacccc gagctgtctg ccagagtgga ccgggaagag  1200
aaggtggact tcaagagcat cctgaaaatc ctgctgaaca acaagaacat caacaaagag  1260
cagagcgaca tcctgcggaa gatccggaac gccttcgatc acaacaatta ccccgacaaa  1320
ggcgtggtgg aaatcaaggc cctgcctgag atcgccatga gcatcaagaa ggcctttggg  1380
gagtacgcca tcatgaaggg atcccttcaa ctgcctccac ttgaaagact gacactgggt  1440
agttcctacc catacgatgt tccagattac gcttatccct acgacgtgcc tgattatgca  1500
tacccatatg atgtccccga ctatgcctaa                                   1530
```

```
SEQ ID NO: 34          moltype = DNA  length = 2175
FEATURE                Location/Qualifiers
misc_feature           1..2175
                       note = N725 Fragment polynucleotide sequence
source                 1..2175
                       mol_type = other DNA
                       organism = synthetic construct
SEQUENCE: 34
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
```

```
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccacatca ggttccacgt gaacatgggc  1080
aagctgagat acctgctgaa ggccgacaag acctgcatcg acggccagac cagagtcaga  1140
gtgatcgagc agcccctgaa cggcttcggc agactggaag aggccgagac aatgcggaag  1200
caagagaacg gcaccttcgg caacagcggc atccggatca gagacttcga gaacatgaag  1260
cgggacgacg ccaatcctgc caactatccc tacatcgtgg acacctacac acactacatc  1320
ctggaaaaca acaaggtcga gatgtttatc aacgacaaag aggacagcgc cccactgctg  1380
cccgtgatcg aggatgatag atacgtggtc aagacaatcc ccagctgccg gatgagcacc  1440
ctggaaattc cagccatggc cttccacatg tttctgttcg gcagcaagaa aaccgagaag  1500
ctgatcgtgg acgtgcacaa ccggtacaag agactgttcc aggccatgca gaaagaagaa  1560
gtgaccgccg agaatatcgc cagcttcgga atcgccgaga gcgacctgcc tcagaagatc  1620
ctggatctga tcagcggcaa tgcccacggc aaggatgtgg acgccttcat cagactgacc  1680
gtggacgaca tgctgaccga caccgagcgg agaatcaaga gattcaagga cgaccggaag  1740
tccattcgga gcgccgacaa caagatggga aagagaggct tcaagcagat ctccacaggc  1800
aagctggccg acttcctggc caaggacatc gtgctgtttc agcccagcgt gaacgatggc  1860
gagaacaaga tcaccggcct gaactaccgg atcatgcaga gcgccattgc cgtgtacgat  1920
agcggcgacg attacgaggc caagcagcag ttcaagctga tgttcgagaa ggcccggctg  1980
atcggcaagg gcacaacaga gcctcatcca tttctgtaca aggtgttcgc ccgcagcatc  2040
cccgccaatg ccgtcgagtt ctacgagcgc tacctgatcg agcggaagtt ctacctgacc  2100
ggcctgtcca acgagatcaa gaaaggcaac agagtggatg tgcccttcat ccggcgggac  2160
cagaacaagt ggaaa                                                    2175

SEQ ID NO: 35           moltype = DNA  length = 1227
FEATURE                 Location/Qualifiers
misc_feature            1..1227
                        note = C726 Fragment polynucleotide sequence
source                  1..1227
                        mol_type = other DNA
                        organism = synthetic construct
SEQUENCE: 35
acacccgcca tgaagaccct gggcagaatc tacagcgagg atctgcccgt ggaactgccc  60
agacagatgt tcgacaatga gatcaagtcc cacctgaagt ccctgccaca gatggaaggc  120
atcgacttca acaatgccaa cgtgacctat ctgatcgccg agtacatgaa gagagtgctg  180
gacgacgact tccagacctt ctaccagtgg aaccgcaact accggtacat ggacatgctt  240
aagggcgagt acgacagaaa gggctccctg cagcactgct tcaccagcgt ggaagagaga  300
gaaggcctct ggaaagagcg ggcctccaga acagagcggt acagaaagca ggccagcaac  360
aagatccgca gcaaccggca gatgagaaac gccagcagcg aagagatcga gacaatcctg  420
gataagcggc tgagcaacag ccggaacgag taccagaaaa gcgagaaagt gatccggcgc  480
tacagagtgc aggatgccct gctgtttctg ctggccaaaa agaccctgac cgaactggcc  540
gatttcgacg gcgagaggtt caaactgaaa gaaatcatgc ccgacgccga gaagggaatc  600
ctgagcgaga tcatgcccat gagcttcacc ttcgagaaag gcggcaagaa gtacaccatc  660
accagcgagg gcatgaagct gaagaactac ggcgacttct ttgtgctggc tagcgacaag  720
aggatcggca acctgctgga actcgtgggc agcgacatcg tgtccaaaga ggatatcatg  780
gaagagttca acaaatacga ccagtgcagg cccgagatca gctccatcgt gttcaacctg  840
gaaaagtggg ccttcgacac ataccccgag ctgtctgcca gagtggaccg ggaagagaag  900
gtggacttca agagcatcct gaaaatcctg ctgaacaaca agaacatcaa caaagagcag  960
agcgacatcc tgcggaagat ccggaacgcc ttcgatcaca acaattaccc cgacaaaggc  1020
gtggtggaaa tcaaggccct gcctgagatc gccatgagca tcaagaaggc ctttggggag  1080
tacgccatca tgaagggatc ccttcaactg cctccacttg aaagactgac actgggtagt  1140
tcctacccat acgatgttcc agattacgct tatccctacg acgtgcctga ttatgcatac  1200
ccatatgatg tccccgacta tgcctaa                                       1227

SEQ ID NO: 36           moltype = DNA  length = 2784
FEATURE                 Location/Qualifiers
misc_feature            1..2784
                        note = N928 Fragment polynucleotide sequence
source                  1..2784
                        mol_type = other DNA
                        organism = synthetic construct
SEQUENCE: 36
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
```

```
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccacatca ggttccacgt gaacatgggc  1080
aagctgagat acctgctgaa ggccgacaag acctgcatcg acggccagac cagagtcaga  1140
gtgatcgagc agcccctgaa cggcttcggc agactggaag aggccgagac aatgcggaag  1200
caagagaacg gcaccttcgg caacagcggc atccggatca gagacttcga gaacatgaag  1260
cgggacgacg ccaatcctgc caactatccc tacatcgtgg acacctacac acactacatc  1320
ctggaaaaca acaaggtcga gatgtttatc aacgacaaag aggacagcgc cccactgctg  1380
cccgtgatcg aggatgatag atacgtggtc aagacaatcc ccagctgccg gatgagcacc  1440
ctggaaattc cagccatggc cttccacatg tttctgttcg gcagcaagaa aaccgagaag  1500
ctgatcgtgg acgtgcacaa ccggtacaag agactgttcc aggccatgca gaaagaagaa  1560
gtgaccgccg agaatatcgc cagcttcgga atcgccgaga gcgacctgcc tcagaagatc  1620
ctggatctga tcagcggcaa tgcccacggc aaggatgtgg acgccttcat cagactgacc  1680
gtggacgaca tgctgaccga caccgagcgg agaatcaaga gattcaagga cgaccggaag  1740
tccattcgga gcgccgacaa caagatggga aagagaggct tcaagcagat ctccacaggc  1800
aagctggccg acttcctggc caaggacatc gtgctgtttc agcccagcgt gaacgatggc  1860
gagaacaaga tcaccggcct gaactaccgg atcatgcaga gcgccattgc cgtgtacgat  1920
agcggcgacg attacgaggc caagcagcag ttcaagctga tgttcgagaa ggcccggctg  1980
atcggcaagg gcacaacaga gcctcatcca tttctgtaca aggtgttcgc ccgcagcatc  2040
cccgccaatg ccgtcgagtt ctacgagcgc tacctgatcg agcggaagtt ctacctgacc  2100
ggcctgtcca acgagatcaa gaaaggcaac agagtggatg tgcccttcat ccggcgggac  2160
cagaacaagt ggaaaacacc cgccatgaag accctgggca gaatctacag cgaggatctg  2220
cccgtggaac tgcccagaca gatgttcgac aatgagatca agtcccacct gaagtccctg  2280
ccacagatgg aaggcatcga cttcaacaat gccaacgtga cctatctgat cgccgagtac  2340
atgaagagag tgctggacga cgacttccag accttctacc agtggaaccg caactaccgg  2400
tacatggaca tgcttaaggg cgagtacgac agaaagggct ccctgcagca ctgcttcacc  2460
agcgtggaag agagagaagg cctctggaaa gagcgggcct ccagaacaga gcggtacaga  2520
aagcaggcca gcaacaagat ccgcagcaac cggcagatga gaaacgccag cagcgaagag  2580
atcgagacaa tcctggataa gcggctgagc aacagccgga acgagtacca gaaaagcgag  2640
aaagtgatcc ggcgctacag agtgcaggat gccctgctgt ttctgctggc caaaaagacc  2700
ctgaccgaac tggccgattt cgacggcgag aggttcaaac tgaaagaaat catgcccgac  2760
gccgagaagg gaatcctgag cgag                                      2784
```

```
SEQ ID NO: 37          moltype = DNA  length = 618
FEATURE                Location/Qualifiers
misc_feature           1..618
                       note = C929 Fragment polynucleotide sequence
source                 1..618
                       mol_type = other DNA
                       organism = synthetic construct
SEQUENCE: 37
atcatgccca tgagcttcac cttcgagaaa ggcggcaaga agtacaccat caccagcgag  60
ggcatgaagc tgaagaacta cggcgacttc tttgtgctgg ctagcgacaa gaggatcggc  120
aacctgctgg aactcgtggg cagcgacatc gtgtccaaag aggatatcat ggaagagttc  180
aacaaatacg accagtgcag gcccgagatc agctccatcg tgttcaacct ggaaaagtgg  240
gccttcgaca catacccccga gctgtctgcc agagtggacc gggaagagaa ggtggacttc  300
aagagcatcc tgaaaatcct gctgaacaac aagaacatca acaaagagca gagcgacatc  360
ctgcggaaga tccggaacgc cttcgatcac aacaattacc ccgacaaagg cgtggtggaa  420
atcaaggccc tgcctgagat cgccatgagc atcaagaagg cctttgggga gtacgccatc  480
atgaagggat cccttcaact gcctccactt gaaagactga cactgggtag ttcctaccca  540
tacgatgttc cagattacgc ttatccctac gacgtgcctg attatgcata cccatatgat  600
gtccccgact atgcctaa                                              618
```

```
SEQ ID NO: 38          moltype = DNA  length = 279
FEATURE                Location/Qualifiers
misc_feature           1..279
                       note = FRB polynucleotide sequence
source                 1..279
                       mol_type = other DNA
                       organism = synthetic construct
SEQUENCE: 38
atcctctggc atgagatgtg gcatgaaggc ctggaagagg catctcgttt gtactttggg  60
gaaaggaacg tgaaaggcat gtttgaggtg ctggagccct tgcatgctat gatggaacgg  120
ggcccccaga ctctgaagga aacatccttt aatcaggcct atggtcgaga tttaatggag  180
gcccaagagt ggtgcaggaa gtacatgaaa tcagggaatg tcaaggacct cacccaagcc  240
tgggacctct attatcatgt gttccgacga atctcaaag                       279
```

```
SEQ ID NO: 39          moltype = DNA  length = 321
FEATURE                Location/Qualifiers
misc_feature           1..321
                       note = FKBP polynucleotide sequence
source                 1..321
                       mol_type = other DNA
                       organism = synthetic construct
SEQUENCE: 39
ggagtgcagg tggaaaccat ctccccagga gacgggcgca ccttccccaa gcgcggccag  60
acctgcgtgg tgcactacac cgggatgctt gaagatggaa agaaatttga ttcctcccgg  120
```

```
gacagaaaca agccctttaa gtttatgcta ggcaagcagg aggtgatccg aggctgggaa  180
gaaggggttg cccagatgag tgtgggtcag agagccaaac tgactatatc tccagattat  240
gcctatggtg ccactgggca cccaggcatc atcccaccac atgccactct cgtcttcgat  300
gtggagcttc taaaactgga a                                            321

SEQ ID NO: 40          moltype = DNA  length = 450
FEATURE                Location/Qualifiers
misc_feature           1..450
                       note = nMag polynucleotide sequence
source                 1..450
                       mol_type = other DNA
                       organism = synthetic construct
SEQUENCE: 40
cacaccctgt acgcccccgg cggctacgac atcatgggct acctggacca gatcggcaac  60
agacccaacc cccaggtgga gctgggcccc gtggacacca gctgcgccct gatcctgtgc  120
gacctgaagc agaaggacac ccccatcgtg tacgccagcg aggccttcct gtatatgacc  180
ggctacagca acgccgaggt gctgggcaga aactgcagat tcctgcagag ccccgacggc  240
atggtgaagc ccaagagcac cagaaagtac gtggacagca acaccatcaa caccatgaga  300
aaggccatcg acagaaacgc cgaggtgcag gtggaggtgg tgaacttcaa gaagaacggc  360
cagagattcg tgaacttcct gaccatgatc cccgtgagag acgagaccgg cgagtacaga  420
tacagcatgg gcttccagtg cgagaccgag                                   450

SEQ ID NO: 41          moltype = DNA  length = 450
FEATURE                Location/Qualifiers
misc_feature           1..450
                       note = pMag polynucleotide sequence
source                 1..450
                       mol_type = other DNA
                       organism = synthetic construct
SEQUENCE: 41
cacaccctgt acgcccccgg cggctacgac atcatgggct acctgagaca gatcagaaac  60
agacccaacc cccaggtgga gctgggcccc gtggacacca gctgcgccct gatcctgtgc  120
gacctgaagc agaaggacac ccccatcgtg tacgccagcg aggccttcct gtatatgacc  180
ggctacagca acgccgaggt gctgggcaga aactgcagat tcctgcagag ccccgacggc  240
atggtgaagc ccaagagcac cagaaagtac gtggacagca acaccatcaa caccatcaga  300
aaggccatcg acagaaacgc cgaggtgcag gtggaggtgg tgaacttcaa gaagaacggc  360
cagagattcg tgaacttcct gaccatcatc cccgtgagag acgagaccgg cgagtacaga  420
tacagcatgg gcttccagtg cgagaccgag                                   450

SEQ ID NO: 42          moltype = DNA  length = 1206
FEATURE                Location/Qualifiers
misc_feature           1..1206
                       note = N272-GS16-FRB-GS16 polynucleotide sequence
source                 1..1206
                       mol_type = other DNA
                       organism = synthetic construct
SEQUENCE: 42
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacaacc cgggatccgg aggaagtggc  840
agctctggcg gcagtggagg gtctggtggc agcggaatcc tctggcatga gatgtggcat  900
gaaggcctgg aagaggcatc tcgtttgtac tttggggaaa ggaacgtgaa aggcatgttt  960
gaggtgctgg agcccttgca tgctatgatg gaacggggcc cccagactct gaaggaaaca  1020
tcctttaatc aggcctatgg tcgagattta atggaggccc aagagtggtg caggaagtac  1080
atgaaatcag ggaatgtcaa ggacctcacc caagcctggg acctctatta tcatgtgttc  1140
cgacgaatct caaagggagg aagcggcggt tccggggggg gatccggaag tggttccggg  1200
gggtag                                                             1206

SEQ ID NO: 43          moltype = DNA  length = 3012
FEATURE                Location/Qualifiers
misc_feature           1..3012
                       note = GS16-FKBP-GS16-C273 polynucleotide sequence
source                 1..3012
                       mol_type = other DNA
                       organism = synthetic construct
SEQUENCE: 43
atgggaggaa gtggcagctc tggcggcagt ggagggtctg gtggcagcgg aggagtgcag  60
gtggaaacca tctccccagg agacgggcgc accttcccca agcgcggcca gacctgcgtg  120
```

```
gtgcactaca ccgggatgct tgaagatgga aagaaatttg attcctcccg ggacagaaac  180
aagcccttta agtttatgct aggcaagcag gaggtgatcc gaggctggga agaaggggtt  240
gcccagatga gtgtgggtca gagagccaaa ctgactatat ctccagatta tgcctatggt  300
gccactgggc acccaggcat catcccacca catgccactc tcgtcttcga tgtggagctt  360
ctaaaactgg aaggaggaag cggcggttcc gggggggat ccggaagtgg ttccgggggg  420
tgtacaagca tcaagctgcc caaggaccgg atccacagcg agaagtccaa caagagcgtg  480
gccatggata tgctcaacga agtgaagcgg tgccccgacg agctgttcac aacactgtct  540
gccgagaagc agtcccggtt cagaatcatc agcgacgacc acaatgaagt gctgatgaag  600
cggagcagcg acagattcgt gcctctgctg ctgcagtata tcgattacgg caagctgttc  660
gaccacatca ggttccacgt gaacatgggc aagctgagat acctgctgaa ggccgacaag  720
acctgcatcg acggccagac cagagtcaga gtgatcgagc agcccctgaa cggcttcggc  780
agactggaag aggccgagac aatgcggaag caagagaacg gcaccttcgg caacagcggc  840
atccggatca gagacttcga gaacatgaag cgggacgacg ccaatcctgc caactatccc  900
tacatcgtgg acacctacac acactacatc ctggaaaaca acaaggtcga gatgtttatc  960
aacgacaaag aggacagcgc cccactgctg cccgtgatcg aggatgatag atacgtggtc  1020
aagacaatcc ccagctgccg gatgagcacc ctggaaattc cagccatggc cttccacatg  1080
tttctgttcg gcagcaagaa aaccgagaag ctgatcgtgg acgtgcacaa ccggtacaag  1140
agactgttcc aggccatgca gaaagaagaa gtgaccgccg agaatatcgc cagcttcgga  1200
atcgccgaga gcgacctgcc tcagaagatc ctggatctga tcagcggcaa tgcccacggc  1260
aaggatgtgg acgccttcat cagactgacc gtggacgaca tgctgaccga caccgagcgg  1320
agaatcaaga gattcaagga cgaccggaag tccattcgga gcgccgacaa caagatggga  1380
aagagaggct tcaagcagat ctccacaggc aagctggccg acttcctggc caaggacatc  1440
gtgctgtttc agcccagcgt gaacgatggc gagaacaaga tcaccggcct gaactaccgg  1500
atcatgcaga gcgccattgc cgtgtacgat agcggcgacg attacgaggc caagcagcag  1560
ttcaagctga tgttcgagaa ggcccggctg atcggcaagg gcacaacaga gcctcatcca  1620
tttctgtaca aggtgttcgc ccgcagcatc cccgccaatg ccgtcgagtt ctacgagcgc  1680
tacctgatcg agcggaagtt ctacctgacc ggcctgtcca acgagatcaa gaaaggcaac  1740
agagtggatg tgcccttcat ccggcgggac cagaacaagt ggaaaacacc cgccatgaag  1800
accctgggca gaatctacag cgaggatctg cccgtggaac tgcccagaca gatgttcgac  1860
aatgagatca agtcccacct gaagtccctg ccacagatgg aaggcatcga cttcaacaat  1920
gccaacgtga cctatctgat cgccgagtac atgaagagag tgctggacga cgacttccag  1980
accttctacc agtggaaccg caactaccgg tacatggaca tgcttaaggg cgagtacgac  2040
agaaagggct ccctgcagca ctgcttcacc agcgtggaag agagagaagg cctctggaaa  2100
gagcgggcct ccagaacaga gcggtacaga aagcaggcca gcaacaagat ccgcagcaac  2160
cggcagatga gaaacgccag cagcgaagag atcgagacaa tcctggataa gcggctgagc  2220
aacagccgga acgagtacca gaaaagcgag aaagtgatcc ggcgctacag agtgcaggat  2280
gccctgctgt ttctgctggc caaaaagacc ctgaccgaac tggccgattt cgacggcgag  2340
aggttcaaac tgaaagaaat catgcccgac gccgagaagg gaatcctgag cgagatcatg  2400
cccatgagct tcaccttcga gaaaggcggc aagaagtaca ccatcaccag cgagggcatg  2460
aagctgaaga actacggcga cttctttgtg ctggctagcg acaagaggat cggcaacctg  2520
ctggaactcg tgggcagcga catcgtgtcc aaagaggata tcatggaaga gttcaacaaa  2580
tacgaccagt gcaggcccga gatcagctcc atcgtgttca acctggaaaa gtgggccttc  2640
gacacatacc ccgagctgtc tgccagagtg gaccgggaag agaaggtgga cttcaagagc  2700
atcctgaaaa tcctgctgaa caacaagaac atcaacaaag agcagagcga catcctgcgg  2760
aagatccgga acgccttcga tcacaacaat taccccgaca aaggcgtggt ggaaatcaag  2820
gccctgcctg agatcgccat gagcatcaag aaggcctttg gggagtacgc catcatgaag  2880
ggatcccttc aactgcctcc acttgaaaga ctgacactgg gtagttccta cccatacgat  2940
gttccagatt acgcttatcc ctacgacgtg cctgattatg catacccata tgatgtcccc  3000
gactatgcct aa                                                     3012
```

```
SEQ ID NO: 44          moltype = DNA  length = 1248
FEATURE                Location/Qualifiers
misc_feature           1..1248
                       note = N286-GS16-FRB-GS16 polynucleotide sequence
source                 1..1248
                       mol_type = other DNA
                       organism = synthetic construct
SEQUENCE: 44
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa cccgggatcc ggaggaagtg gcagctctgg cggcagtgga  900
gggtctggtg gcagcggaat cctctggcat gagatgtggc atgaaggcct ggaagaggca  960
tctcgtttgt actttgggga aaggaacgtg aaaggcatgt ttgaggtgct ggagcccttg  1020
catgctatga tggaacgggg cccccagact ctgaaggaaa catcctttaa tcaggcctat  1080
ggtcgagatt taatggaggc ccaagagtgg tgcaggaagt acatgaaatc agggaatgtc  1140
aaggacctca cccaagcctg ggacctctat tatcatgtgt tccgacgaat ctcaaaggga  1200
ggaagcggcg gttccggggg ggatccggaa agtggttccg gggggtag               1248
```

```
SEQ ID NO: 45          moltype = DNA  length = 2970
FEATURE                Location/Qualifiers
misc_feature           1..2970
                       note = GS16-FKBP-GS16-C287 polynucleotide sequence
source                 1..2970
                       mol_type = other DNA
                       organism = synthetic construct
SEQUENCE: 45
atgggaggaa gtggcagctc tggcggcagt ggagggtctg gtggcagcgg aggagtgcag  60
gtggaaacca tctccccagg agacgggcgc accttcccca agcgcggcca gacctgcgtg  120
gtgcactaca ccgggatgct tgaagatgga aagaaatttg attcctcccg ggacagaaac  180
aagcccttta agtttatgct aggcaagcag gaggtgatcc gaggctggga agaaggggtt  240
gcccagatga gtgtgggtca gagagccaaa ctgactatat ctccagatta tgcctatggt  300
gccactgggc acccaggcat catcccacca catgccactc tcgtcttcga tgtggagctt  360
ctaaaactgg aaggaggaag cggcggttcc gggggggggat ccggaagtgg ttccgggggg  420
tgtacaaaca agagcgtggc catggatatg ctcaacgaag tgaagcggtg ccccgacgag  480
ctgttcacaa cactgtctgc cgagaagcag tcccggttca gaatcatcag cgacgaccac  540
aatgaagtgc tgatgaagcg gagcagcgac agattcgtgc ctctgctgct gcagtatatc  600
gattacggca agctgttcga ccacatcagg ttccacgtga acatgggcaa gctgagatac  660
ctgctgaagg ccgacaagac ctgcatcgac ggccagacca gagtcagagt gatcgagcag  720
cccctgaacg gcttcggcag actggaagag gccgagacaa tgcggaagca agagaacggc  780
accttcggca acagcggcat ccggatcaga gacttcgaga acatgaagcg ggacgacgcc  840
aatcctgcca actatcccta catcgtggac acctacacac actacatcct ggaaaacaac  900
aaggtcgaga tgtttatcaa cgacaaagag gacagcgccc cactgctgcc cgtgatcgag  960
gatgatagat acgtggtcaa gacaatcccc agctgccgga tgagcaccct ggaaattcca  1020
gccatggcct tccacatgtt tctgttcggc agcaagaaaa ccgagaagct gatcgtggac  1080
gtgcacaacc ggtacaagag actgttccag gccatgcaga aagaagaagt gaccgccgag  1140
aatatcgcca gcttcggaat cgccgagagc gacctgcctc agaagatcct ggatctgatc  1200
agcggcaatg cccacggcaa ggatgtggac gccttcatca gactgaccgt ggacgacatg  1260
ctgaccgaca ccgagcggag aatcaagaga ttcaaggacg accggaagtc cattcggagc  1320
gccgacaaca agatgggaaa gagaggcttc aagcagatct ccacaggcaa gctggccgac  1380
ttcctggcca aggacatcgt gctgtttcag cccagcgtga acgatggcga gaacaagatc  1440
accggcctga actaccggat catgcagagc gccattgccg tgtacgatag cggcgacgat  1500
tacgaggcca agcagcagtt caagctgatg ttcgagaagg cccggctgat cggcaagggc  1560
acaacagagc ctcatccatt tctgtacaag gtgttcgccc gcagcatccc cgccaatgcc  1620
gtcgagttct acgagcgcta cctgatcgag cggaagttct acctgaccgg cctgtccaac  1680
gagatcaaga aggcaacag agtggatgtg cccttcatcc ggcgggacca gaacaagtgg  1740
aaaacacccg ccatgaagac cctgggcaga atctacagcg aggatctgcc cgtggaactg  1800
cccagacaga tgttcgacaa tgagatcaag tcccacctga agtccctgcc acagatggaa  1860
ggcatcgact tcaacaatgc caacgtgacc tatctgatcg ccgagtacat gaagagagtg  1920
ctggacgacg acttccagac cttctaccag tggaaccgca actaccggta catggacatg  1980
cttaagggcg agtacgacag aaagggctcc ctgcagcact gcttcaccag cgtggaagag  2040
agagaaggcc tctggaaaga gcgggcctcc agaacagagc ggtacagaaa gcaggccagc  2100
aacaagatcc gcagcaaccg gcagatgaga aacgccagca gcgaagagat cgagacaatc  2160
ctggataagc ggctgagcaa cagccggaac gagtaccaga aaagcgagaa agtgatccgg  2220
cgctacagag tgcaggatgc cctgctgttt ctgctggcca aaaagaccct gaccgaactg  2280
gccgatttcg acggcgagag gttcaaactg aaagaaatca tgcccgacgc cgagaaggga  2340
atcctgagcg agatcatgcc catgagcttc accttcgaga aaggcggcaa gaagtacacc  2400
atcaccagcg agggcatgaa gctgaagaac tacggcgact tctttgtgct ggctagcgac  2460
aagaggatcg gcaacctgct ggaactcgtg ggcagcgaca tcgtgtccaa agaggatatc  2520
atggaagagt tcaacaaata cgaccagtgc aggcccgaga tcagctccat cgtgttcaac  2580
ctggaaaagt gggccttcga cacatacccc gagctgtctg ccagagtgga ccgggaagag  2640
aaggtggact tcaagagcat cctgaaaatc ctgctgaaca acaagaacat caacaaagag  2700
cagagcgaca tcctgcggaa gatccggaac gccttcgatc acaacaatta ccccgacaaa  2760
ggcgtggtgg aaatcaaggc cctgcctgag atcgccatga gcatcaagaa ggcctttggg  2820
gagtacgcca tcatgaaggg atcccttcaa ctgcctccac ttgaaagact gacactgggt  2880
agttcctacc catacgatgt tccagattac gcttatccct acgacgtgcc tgattatgca  2940
tacccatatg atgtccccga ctatgcctaa                                  2970

SEQ ID NO: 46          moltype = DNA  length = 1443
FEATURE                Location/Qualifiers
misc_feature           1..1443
                       note = N351-GS16-FRB-GS16 polynucleotide sequence
source                 1..1443
                       mol_type = other DNA
                       organism = synthetic construct
SEQUENCE: 46
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
```

```
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccttccgg gatccggagg aagtggcagc  1080
tctggcggca gtggagggtc tggtggcagc ggaatcctct ggcatgagat gtggcatgaa  1140
ggcctggaag aggcatctcg tttgtacttt ggggaaagga acgtgaaagg catgtttgag  1200
gtgctggagc ccttgcatgc tatgatggaa cggggccccc agactctgaa ggaaacatcc  1260
tttaatcagg cctatggtcg agatttaatg gaggcccaag agtggtgcag gaagtacatg  1320
aaatcaggga atgtcaagga cctcacccaa gcctgggacc tctattatca tgtgttccga  1380
cgaatctcaa agggaggaag cggcggttcc ggggggggat ccggaagtgg ttccgggggg  1440
tag                                                                1443
```

```
SEQ ID NO: 47          moltype = DNA  length = 2775
FEATURE                Location/Qualifiers
misc_feature           1..2775
                       note = GS16-FKBP-GS16-C352 polynucleotide sequence
source                 1..2775
                       mol_type = other DNA
                       organism = synthetic construct
SEQUENCE: 47
atgggaggaa gtggcagctc tggcggcagt ggagggtctg gtggcagcgg aggagtgcag  60
gtggaaacca tctccccagg agacgggcgc accttcccca agcgcggcca gacctgcgtg  120
gtgcactaca ccgggatgct tgaagatgga aagaaatttg attcctcccg ggacagaaac  180
aagcccttta agtttatgct aggcaagcag gaggtgatcc gaggctggga agaaggggtt  240
gcccagatga gtgtgggtca gagagccaaa ctgactatat ctccagatta tgcctatggt  300
gccactgggc acccaggcat catcccacca catgccactc tcgtcttcga tgtggagctt  360
ctaaaactgg aaggaggaag cggcggttcc ggggggggat ccggaagtgg ttccgggggg  420
tgtacacaca tcaggttcca cgtgaacatg ggcaagctga gatacctgct gaaggccgac  480
aagacctgca tcgacggcca gaccagagtc agagtgatcg agcagcccct gaacggcttc  540
ggcagactgg aagaggccga gacaatgcgg aagcaagaga acggcacctt cggcaacagc  600
ggcatccgga tcagagactt cgagaacatg aagcgggacg acgccaatcc tgccaactat  660
ccctacatcg tggacaccta cacactactac atcctggaaa acaacaaggt cgagatgttt  720
atcaacgaca aagaggacag cgccccactg ctgcccgtga tcgaggatga tagatacgtg  780
gtcaagacaa tccccagctg ccggatgagc accctggaaa ttccagccat ggccttccac  840
atgtttctgt tcggcagcaa gaaaaccgag aagctgatcg tggacgtgca caaccggtac  900
aagagactgt tccaggccat gcagaaagaa gaagtgaccg ccgagaatat cgccagcttc  960
ggaatcgccg agagcgacct gcctcagaag atcctggatc tgatcagcgg caatgcccac  1020
ggcaaggatg tggacgcctt catcagactg accgtggacg acatgctgac cgacaccgag  1080
cggagaatca agagattcaa ggacgaccgg aagtccattc ggagcgccga caacaagatg  1140
ggaaagagag gcttcaagca gatctccaca ggcaagctgg ccgacttcct ggccaaggac  1200
atcgtgctgt ttcagcccag cgtgaacgat ggcgagaaca agatcaccgg cctgaactac  1260
cggatcatgc agagcgccat tgccgtgtac gatagcggcg acgattacga ggccaagcag  1320
cagttcaagc tgatgttcga gaaggcccgg ctgatcggca agggcacaac agagcctcat  1380
ccatttctgt acaaggtgtt cgcccgcagc atccccgcca atgccgtcga gttctacgag  1440
cgctacctga tcgagcggaa gttctacctg accggcctgt ccaacgagat caagaaaggc  1500
aacagagtgg atgtgccctt catccggcgg gaccagaaca agtggaaaac acccgccatg  1560
aagaccctgg gcagaatcta cagcgaggat ctgcccgtgg aactgcccag acagatgttc  1620
gacaatgaga tcaagtccca cctgaagtcc ctgccacaga tggaaggcat cgacttcaac  1680
aatgccaacg tgacctatct gatcgccgag tacatgaaga gagtgctgga cgacgacttc  1740
cagaccttct accagtggaa ccgcaactac cggtacatgg acatgcttaa gggcgagtac  1800
gacagaaagg gctccctgca gcactgcttc accagcgtgg aagagagaga aggcctctgg  1860
aaagagcggg cctccagaac agagcggtac agaaagcagg ccagcaacaa gatccgcagc  1920
aaccggcaga tgagaaacgc cagcagcgaa gagatcgaga caatcctgga taagcggctg  1980
agcaacagcc ggaacgagta ccagaaaagc gagaaagtga tccggcgcta cagagtgcag  2040
gatgccctgc tgtttctgct ggccaaaaag accctgaccg aactggccga tttcgacggc  2100
gagaggttca aactgaaaga aatcatgccc gacgccgaga agggaatcct gagcgagatc  2160
atgcccatga gcttcacctt cgagaaaggc ggcaagaagt acaccatcac cagcgagggc  2220
atgaagctga agaactacgg cgacttcttt gtgctggcta gcgacaagag gatcggcaac  2280
ctgctggaac tcgtgggcag cgacatcgtg tccaaagagg atatcatgga agagttcaac  2340
aaatacgacc agtgcaggcc cgagatcagc tccatcgtgt tcaacctgga aaagtgggcc  2400
ttcgacacat accccgagct gtctgccaga gtggaccggg aagagaaggt ggacttcaag  2460
agcatcctga aaatcctgct gaacaacaag aacatcaaca aagagcagag cgacatcctg  2520
cggaagatcc ggaacgcctt cgatcacaac aattaccccg acaaaggcgt ggtggaaatc  2580
aaggccctgc ctgagatcgc catgagcatc aagaaggcct ttggggagta cgccatcatg  2640
aagggatccc ttcaactgcc tccacttgaa agactgacac tgggtagttc ctacccatac  2700
gatgttccag attacgctta tccctacgac gtgcctgatt atgcataccc atatgatgtc  2760
cccgactatg cctaa                                                   2775
```

```
SEQ ID NO: 48          moltype = DNA  length = 1830
FEATURE                Location/Qualifiers
misc_feature           1..1830
                       note = N480-GS16-FRB-GS16 polynucleotide sequence
source                 1..1830
                       mol_type = other DNA
                       organism = synthetic construct
SEQUENCE: 48
```

```
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccacatca ggttccacgt gaacatgggc  1080
aagctgagat acctgctgaa ggccgacaag acctgcatcg acggccagac cagagtcaga  1140
gtgatcgagc agcccctgaa cggcttcggc agactggaag aggccgagac aatgcggaag  1200
caagagaacg gcaccttcgg caacagcggc atccggatca gagacttcga gaacatgaag  1260
cgggacgacg ccaatcctgc caactatccc tacatcgtgg acacctacac acactacatc  1320
ctggaaaaca acaaggtcga gatgtttatc aacgacaaag aggacagcgc cccactgctg  1380
cccgtgatcg aggatgatag atacgtggtc aagacaatcc ccagctgccg gatgagcacc  1440
cttccgggat ccggaggaag tggcagctct ggcggcagtg gagggtctgg tggcagcgga  1500
atcctctggc atgagatgtg gcatgaaggc ctggaagagg catctcgttt gtactttggg  1560
gaaaggaacg tgaaaggcat gtttgaggtg ctggagccct tgcatgctat gatggaacgg  1620
ggcccccaga ctctgaagga aacatccttt aatcaggcct atggtcgaga tttaatggag  1680
gcccaagagt ggtgcaggaa gtacatgaaa tcagggaatg tcaaggacct cacccaagcc  1740
tgggacctct attatcatgt gttccgacga atctcaaagg gaggaagcgg cggttccggg  1800
gggggatccg gaagtggttc cggggggtag                                  1830
```

```
SEQ ID NO: 49          moltype = DNA  length = 2388
FEATURE                Location/Qualifiers
misc_feature           1..2388
                       note = GS16-FKBP-GS16-C481 polynucleotide sequence
source                 1..2388
                       mol_type = other DNA
                       organism = synthetic construct
SEQUENCE: 49
atgggaggaa gtggcagctc tggcggcagt ggagggtctg gtggcagcgg aggagtgcag  60
gtggaaacca tctccccagg agacgggcgc accttcccca agcgcggcca gacctgcgtg  120
gtgcactaca ccgggatgct tgaagatgga aagaaatttg attcctcccg ggacagaaac  180
aagcccttta agtttatgct aggcaagcag gaggtgatcc gaggctggga agaaggggtt  240
gcccagatga gtgtgggtca gagagccaaa ctgactatat ctccagatta tgcctatggt  300
gccactgggc acccaggcat catcccacca catgccactc tcgtcttcga tgtggagctt  360
ctaaaactgg aaggaggaag cggcggttcc ggggggggat ccggaagtgg ttccgggggg  420
tgtacactgg aaattccagc catggccttc cacatgtttc tgttcggcag caagaaaacc  480
gagaagctga tcgtggacgt gcacaaccgg tacaagagac tgttccaggc catgcagaaa  540
gaagaagtga ccgccgagaa tatcgccagc ttcggaatcg ccgagagcga cctgcctcag  600
aagatcctgg atctgatcag cggcaatgcc cacggcaagg atgtggacgc cttcatcaga  660
ctgaccgtgg acgacatgct gaccgacacc gagcggagaa tcaagagatt caaggacgac  720
cggaagtcca ttcggagcgc cgacaacaag atgggaaaga gaggcttcaa gcagatctcc  780
acaggcaagc tggccgactt cctggccaag gacatcgtgc tgtttcagcc cagcgtgaac  840
gatggcgaga acaagatcac cggcctgaac taccggatca tgcagagcgc cattgccgtg  900
tacgatagcg gcgacgatta cgaggccaag cagcagttca agctgatgtt cgagaaggcc  960
cggctgatcg gcaagggcac aacagagcct catccatttc tgtacaaggt gttcgcccgc  1020
agcatccccg ccaatgccgt cgagttctac gagcgctacc tgatcgagcg gaagttctac  1080
ctgaccggcc tgtccaacga gatcaagaaa ggcaacagag tggatgtgcc cttcatccgg  1140
cgggaccaga acaagtggaa aacacccgcc atgaagaccc tgggcagaat ctacagcgag  1200
gatctgcccg tggaactgcc cagacagatg ttcgacaatg agatcaagtc ccacctgaag  1260
tccctgccac agatggaagg catcgacttc aacaatgcca acgtgaccta tctgatcgcc  1320
gagtacatga agagagtgct ggacgacgac ttccagacct tctaccagtg gaaccgcaac  1380
taccggtaca tggacatgct taagggcgag tacgacagaa agggctccct gcagcactgc  1440
ttcaccagcg tggaagagag agaaggcctc tggaaagagc gggcctccag aacagagcgg  1500
tacagaaagc aggccagcaa caagatccgc agcaaccggc agatgagaaa cgccagcagc  1560
gaagagatcg agacaatcct ggataagcgg ctgagcaaca gccggaacga gtaccagaaa  1620
agcgagaaag tgatccggcg ctacagagtg caggatgccc tgctgtttct gctggccaaa  1680
aagaccctga ccgaactggc cgatttcgac ggcgagaggt tcaaactgaa agaaatcatg  1740
cccgacgccg agaagggaat cctgagcgag atcatgccca tgagcttcac cttcgagaaa  1800
ggcggcaaga agtacaccat caccagcgag ggcatgaagc tgaagaacta cggcgacttc  1860
tttgtgctgg ctagcgacaa gaggatcggc aacctgctgg aactcgtggg cagcgacatc  1920
gtgtccaaag aggatatcat ggaagagttc aacaaatacg accagtgcag gcccgagatc  1980
agctccatcg tgttcaacct ggaaaagtgg gccttcgaca cataccccga gctgtctgcc  2040
agagtggacc gggaagagaa ggtggacttc aagagcatcc tgaaaatcct gctgaacaac  2100
aagaacatca acaaagagca gagcgacatc ctgcggaaga tccggaacgc cttcgatcac  2160
aacaattacc ccgacaaagg cgtggtggaa atcaaggccc tgcctgagat cgccatgagc  2220
atcaagaagg cctttgggga gtacgccatc atgaagggat cccttcaact gcctccactt  2280
gaaagactga cactgggtag ttcctaccca tacgatgttc cagattacgc ttatccctac  2340
```

```
gacgtgcctg attatgcata cccatatgat gtccccgact atgcctaa              2388

SEQ ID NO: 50          moltype = DNA  length = 2040
FEATURE                Location/Qualifiers
misc_feature           1..2040
                       note = N550-GS16-FRB-GS16 polynucleotide sequence
source                 1..2040
                       mol_type = other DNA
                       organism = synthetic construct
SEQUENCE: 50
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccacatca ggttccacgt gaacatgggc  1080
aagctgagat acctgctgaa ggccgacaag acctgcatcg acggccagac cagagtcaga  1140
gtgatcgagc agcccctgaa cggcttcggc agactggaag aggccgagac aatgcggaag  1200
caagagaacg gcaccttcgg caacagcggc atccggatca gagacttcga gaacatgaag  1260
cgggacgacg ccaatcctgc caactatccc tacatcgtgg acacctacac acactacatc  1320
ctggaaaaca acaaggtcga gatgtttatc aacgacaaag aggacagcgc cccactgctg  1380
cccgtgatcg aggatgatag atacgtggtc aagacaatcc ccagctgccg gatgagcacc  1440
ctggaaattc cagccatggc cttccacatg tttctgttcg gcagcaagaa aaccgagaag  1500
ctgatcgtgg acgtgcacaa ccggtacaag agactgttcc aggccatgca gaaagaagaa  1560
gtgaccgccg agaatatcgc cagcttcgga atcgccgaga gcgacctgcc tcagaagatc  1620
ctggatctga tcagcggcaa tgcccacggc ttcccgggat ccggaggaag tggcagctct  1680
ggcggcagtg gagggtctgg tggcagcgga atcctctggc atgagatgtg gcatgaaggc  1740
ctggaagagg catctcgttt gtactttggg gaaaggaacg tgaaaggcat gtttgaggtg  1800
ctggagccct tgcatgctat gatggaacgg ggcccccaga ctctgaagga aacatccttt  1860
aatcaggcct atggtcgaga tttaatggag gcccaagagt ggtgcaggaa gtacatgaaa  1920
tcagggaatg tcaaggacct cacccaagcc tgggacctct attatcatgt gttccgacga  1980
atctcaaagg gaggaagcgg cggttccggg gggggatccg gaagtggttc cggggggtag  2040

SEQ ID NO: 51          moltype = DNA  length = 2178
FEATURE                Location/Qualifiers
misc_feature           1..2178
                       note = GS16-FKBP-GS16-C551 polynucleotide sequence
source                 1..2178
                       mol_type = other DNA
                       organism = synthetic construct
SEQUENCE: 51
atgggaggaa gtggcagctc tggcggcagt ggagggtctg gtggcagcgg aggagtgcag  60
gtggaaacca tctccccagg agacgggcgc accttcccca agcgcggcca gacctgcgtg  120
gtgcactaca ccgggatgct tgaagatgga aagaaatttg attcctcccg ggacagaaac  180
aagcccttta agtttatgct aggcaagcag gaggtgatcc gaggctggga agaaggggtt  240
gcccagatga gtgtgggtca gagagccaaa ctgactatat ctccagatta tgcctatggt  300
gccactgggc acccaggcat catcccacca catgccactc tcgtcttcga tgtggagctt  360
ctaaaactgg aaggaggaag cggcggttcc ggggggggat ccggaagtgg ttccgggggg  420
tgtacaaagg atgtggacgc cttcatcaga ctgaccgtgg acgacatgct gaccgacacc  480
gagcggagaa tcaagagatt caaggacgac cggaagtcca ttcggagcgc cgacaacaag  540
atgggaaaga gaggcttcaa gcagatctcc acaggcaagc tggccgactt cctggccaag  600
gacatcgtgc tgtttcagcc cagcgtgaac gatggcgaga acaagatcac cggcctgaac  660
taccggatca tgcagagcgc cattgccgtg tacgatagcg gcgacgatta cgaggccaag  720
cagcagttca agctgatgtt cgagaaggcc cggctgatcg gcaagggcac aacagagcct  780
catccatttc tgtacaaggt gttcgcccgc agcatccccg ccaatgccgt cgagttctac  840
gagcgctacc tgatcgagcg gaagttctac ctgaccggcc tgtccaacga gatcaagaaa  900
ggcaacagag tggatgtgcc cttcatccgg cgggaccaga acaagtggaa aacacccgcc  960
atgaagaccc tgggcagaat ctacagcgag gatctgcccg tggaactgcc cagacagatg  1020
ttcgacaatg agatcaagtc ccacctgaag tccctgccac agatggaagg catcgacttc  1080
aacaatgcca acgtgaccta tctgatcgcc gagtacatga agagagtgct ggacgacgac  1140
ttccagacct tctaccagtg gaaccgcaac taccggtaca tggacatgct taagggcgag  1200
tacgacagaa agggctccct gcagcactgc ttcaccagcg tggaagagag agaaggcctc  1260
tggaaagagc gggcctccag aacagagcgg tacagaaagc aggccagcaa caagatccgc  1320
agcaaccggc agatgagaaa cgccagcagc gaagagatcg agacaatcct ggataagcgg  1380
ctgagcaaca gccggaacga gtaccagaaa agcgagaaag tgatccggcg ctacagagtg  1440
caggatgccc tgctgtttct gctggccaaa aagaccctga ccgaactggc cgatttcgac  1500
ggcgagaggt tcaaactgaa agaaatcatg cccgacgccg agaagggaat cctgagcgag  1560
```

```
atcatgccca tgagcttcac cttcgagaaa ggcggcaaga agtacaccat caccagcgag  1620
ggcatgaagc tgaagaacta cggcgacttc tttgtgctgg ctagcgacaa gaggatcggc  1680
aacctgctgg aactcgtggg cagcgacatc gtgtccaaag aggatatcat ggaagagttc  1740
aacaaatacg accagtgcag gcccgagatc agctccatcg tgttcaacct ggaaaagtgg  1800
gccttcgaca catacccga gctgtctgcc agagtggacc gggaagagaa ggtggacttc  1860
aagagcatcc tgaaaatcct gctgaacaac aagaacatca acaaagagca gagcgacatc  1920
ctgcggaaga tccggaacgc cttcgatcac aacaattacc ccgacaaagg cgtggtggaa  1980
atcaaggccc tgcctgagat cgccatgagc atcaagaagg cctttgggga gtacgccatc  2040
atgaagggat cccttcaact gcctccactt gaaagactga cactgggtag ttcctaccca  2100
tacgatgttc cagattacgc ttatccctac gacgtgcctg attatgcata cccatatgat  2160
gtccccgact atgcctaa                                                2178
```

SEQ ID NO: 52 moltype = DNA length = 2262
FEATURE Location/Qualifiers
misc_feature 1..2262
note = N624-GS16-FRB-GS16 polynucleotide sequence
source 1..2262
mol_type = other DNA
organism = synthetic construct
SEQUENCE: 52

```
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccacatca ggttccacgt gaacatgggc  1080
aagctgagat acctgctgaa ggccgacaag acctgcatcg acggccagac cagagtcaga  1140
gtgatcgagc agcccctgaa cggcttcggc agactggaag aggccgagac aatgcggaag  1200
caagagaacg gcaccttcgg caacagcggc atccggatca gagacttcga gaacatgaag  1260
cgggacgacg ccaatcctgc caactatccc tacatcgtgg acacctacac acactacatc  1320
ctggaaaaca acaaggtcga gatgtttatc aacgacaaag aggacagcgc cccactgctg  1380
cccgtgatcg aggatgatag atacgtggtc aagacaatcc ccagctgccg gatgagcacc  1440
ctggaaattc cagccatggc cttccacatg tttctgttcg gcagcaagaa aaccgagaag  1500
ctgatcgtgg acgtgcacaa ccggtacaag agactgttcc aggccatgca gaaagaagaa  1560
gtgaccgccg agaatatcgc cagcttcgga atcgccgaga gcgacctgcc tcagaagatc  1620
ctggatctga tcagcggcaa tgcccacggc aaggatgtgg acgccttcat cagactgacc  1680
gtggacgaca tgctgaccga caccgagcgg agaatcaaga gattcaagga cgaccggaag  1740
tccattcgga gcgccgacaa caagatggga aagagaggct tcaagcagat ctccacaggc  1800
aagctggccg acttcctggc caaggacatc gtgctgtttc agcccagcgt gaacgatggc  1860
gagaacaaga tcaacccggg atccggagga agtggcagct ctggcggcag tggagggtct  1920
ggtggcagcg gaatcctctg gcatgagatg tggcatgaag gcctggaaga ggcatctcgt  1980
ttgtactttg gggaaaggaa cgtgaaaggc atgtttgagg tgctggagcc cttgcatgct  2040
atgatggaac ggggccccca gactctgaag gaaacatcct ttaatcaggc ctatggtcga  2100
gatttaatgg aggcccaaga gtggtgcagg aagtacatga aatcagggaa tgtcaaggac  2160
ctcacccaag cctgggacct ctattatcat gtgttccgac gaatctcaaa gggaggaagc  2220
ggcggttccg gggggggatc cggaagtggt tccgggggt ag                      2262
```

SEQ ID NO: 53 moltype = DNA length = 1956
FEATURE Location/Qualifiers
misc_feature 1..1956
note = GS16-FKBP-GS16-C625 polynucleotide sequence
source 1..1956
mol_type = other DNA
organism = synthetic construct
SEQUENCE: 53

```
atgggaggaa gtggcagctc tggcggcagt ggagggtctg gtggcagcgg aggagtgcag  60
gtggaaacca tctccccagg agacgggcgc accttcccca agcgcggcca gacctgcgtg  120
gtgcactaca ccgggatgct tgaagatgga aagaaatttg attcctcccg ggacagaaac  180
aagcccttta agtttatgct aggcaagcag gaggtgatcc gaggctggga agaaggggtt  240
gcccagatga gtgtgggtca gagagccaaa ctgactatat ctccagatta tgcctatggt  300
gccactgggc acccaggcat catcccacca catgccactc tcgtcttcga tgtggagctt  360
ctaaaactgg aaggaggaag cggcggttcc ggggggggat ccggaagtgg ttccgggggg  420
tgtacaaccg gcctgaacta ccggatcatg cagagcgcca ttgccgtgta cgatagcggc  480
gacgattacg aggccaagca gcagttcaag ctgatgttcg agaaggcccg gctgatcggc  540
aagggcacaa cagagcctca tccatttctg tacaaggtgt tcgcccgcag catccccgcc  600
aatgccgtcg agttctacga gcgctacctg atcgagcgga agttctacct gaccggcctg  660
tccaacgaga tcaagaaagg caacagagtg gatgtgccct tcatccggcg ggaccagaac  720
```

```
aagtggaaaa cacccgccat gaagaccctg ggcagaatct acagcgagga tctgcccgtg  780
gaactgccca gacagatgtt cgacaatgag atcaagtccc acctgaagtc cctgccacag  840
atggaaggca tcgacttcaa caatgccaac gtgacctatc tgatcgccga gtacatgaag  900
agagtgctgg acgacgactt ccagaccttc taccagtgga accgcaacta ccggtacatg  960
gacatgctta agggcgagta cgacagaaag ggctccctgc agcactgctt caccagcgtg  1020
gaagagagag aaggcctctg gaaagagcgg gcctccagaa cagagcggta cagaaagcag  1080
gccagcaaca agatccgcag caaccggcag atgagaaacg ccagcagcga agagatcgag  1140
acaatcctgg ataagcggct gagcaacagc cggaacgagt accagaaaag cgagaaagtg  1200
atccggcgct acagagtgca ggatgccctg ctgtttctgc tggccaaaaa gaccctgacc  1260
gaactggccg atttcgacgg cgagaggttc aaactgaaag aaatcatgcc cgacgccgag  1320
aagggaatcc tgagcgagat catgcccatg agcttcacct tcgagaaagg cggcaagaag  1380
tacaccatca ccagcgaggg catgaagctg aagaactacg gcgacttctt tgtgctggct  1440
agcgacaaga ggatcggcaa cctgctggaa ctcgtgggca gcgacatcgt gtccaaagag  1500
gatatcatgg aagagttcaa caaatacgac cagtgcaggc ccgagatcag ctccatcgtg  1560
ttcaacctgg aaaagtgggc cttcgacaca taccccgagc tgtctgccag agtggaccgg  1620
gaagagaagg tggacttcaa gagcatcctg aaaatcctgc tgaacaacaa gaacatcaac  1680
aaagagcaga gcgacatcct gcggaagatc cggaacgcct tcgatcacaa caattacccc  1740
gacaaaggcg tggtggaaat caaggccctg cctgagatcg ccatgagcat caagaaggcc  1800
tttggggagt acgccatcat gaagggatcc cttcaactgc ctccacttga aagactgaca  1860
ctgggtagtt cctacccata cgatgttcca gattacgctt atccctacga cgtgcctgat  1920
tatgcatacc catatgatgt ccccgactat gcctaa                           1956

SEQ ID NO: 54          moltype = DNA  length = 2565
FEATURE                Location/Qualifiers
misc_feature           1..2565
                       note = N725-GS16-FRB-GS16 polynucleotide sequence
source                 1..2565
                       mol_type = other DNA
                       organism = synthetic construct
SEQUENCE: 54
atgaacatcc ccgctctggt ggaaaaccag aagaagtact tggcacccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccacatca ggttccacgt gaacatgggc  1080
aagctgagat acctgctgaa ggccgacaag acctgcatcg acggccagac cagagtcaga  1140
gtgatcgagc agcccctgaa cggcttcggc agactggaag aggccgagac aatgcggaag  1200
caagagaacg gcaccttcgg caacagcggc atccggatca gagacttcga gaacatgaag  1260
cgggacgacg ccaatcctgc caactatccc tacatcgtgg acacctacac acactacatc  1320
ctggaaaaca acaaggtcga gatgtttatc aacgacaaag aggacagcgc cccactgctg  1380
cccgtgatcg aggatgatag atacgtggtc aagacaatcc ccagctgccg gatgagcacc  1440
ctggaaattc cagccatggc cttccacatg tttctgttcg gcagcaagaa aaccgagaag  1500
ctgatcgtgg acgtgcacaa ccggtacaag agactgttcc aggccatgca gaaagaagaa  1560
gtgaccgccg agaatatcgc cagcttcgga atcgccgaga gcgacctgcc tcagaagatc  1620
ctggatctga tcagcggcaa tgcccacggc aaggatgtgg acgccttcat cagactgacc  1680
gtggacgaca tgctgaccga caccgagcgg agaatcaaga gattcaagga cgaccggaag  1740
tccattcgga gcgccgacaa caagatggga aagagaggct tcaagcagat ctccacaggc  1800
aagctggccg acttcctggc caaggacatc gtgctgtttc agcccagcgt gaacgatggc  1860
gagaacaaga tcaccggcct gaactaccgg atcatgcaga gcgccattgc cgtgtacgat  1920
agcggcgacg attacgaggc caagcagcag ttcaagctga tgttcgagaa ggcccggctg  1980
atcggcaagg gcacaacaga gcctcatcca tttctgtaca aggtgttcgc ccgcagcatc  2040
cccgccaatg ccgtcgagtt ctacgagcgc tacctgatcg agcggaagtt ctacctgacc  2100
ggcctgtcca acgagatcaa gaaaggcaac agagtggatg tgcccttcat ccggcgggac  2160
cagaacaagt ggaaaccccc gggatccgga ggaagtggca gctctggcgg cagtggaggg  2220
tctggtggca gcggaatcct ctggcatgag atgtggcatg aaggcctgga agaggcatct  2280
cgtttgtact tggggaaag gaacgtgaaa ggcatgtttg aggtgctgga gcccttgcat  2340
gctatgatgg aacggggccc ccagactctg aaggaaacat cctttaatca ggcctatggt  2400
cgagatttaa tggaggccca agagtggtgc aggaagtaca tgaaatcagg gaatgtcaag  2460
gacctcaccc aagcctggga cctctattat catgtgttcc gacgaatctc aaagggagga  2520
agcggcggtt ccgggggggg atccggaagt ggttccgggg ggtag                  2565

SEQ ID NO: 55          moltype = DNA  length = 1653
FEATURE                Location/Qualifiers
misc_feature           1..1653
                       note = GS16-FKBP-GS16-C726 polynucleotide sequence
source                 1..1653
```

```
                        mol_type = other DNA
                        organism = synthetic construct
SEQUENCE: 55
atgggaggaa gtggcagctc tggcggcagt ggagggtctg gtggcagcgg aggagtgcag  60
gtggaaacca tctccccagg agacgggcgc accttcccca agcgcggcca gacctgcgtg  120
gtgcactaca ccgggatgct tgaagatgga aagaaatttg attcctcccg ggacagaaac  180
aagcccttta agtttatgct aggcaagcag gaggtgatcc gaggctggga agaaggggtt  240
gcccagatga gtgtgggtca gagagccaaa ctgactatat ctccagatta tgcctatggt  300
gccactgggc acccaggcat catcccacca catgccactc tcgtcttcga tgtggagctt  360
ctaaaactgg aaggaggaag cggcggttcc ggggggggat ccggaagtgg ttccgggggg  420
tgtacaacac ccgccatgaa gaccctgggc agaatctaca gcgaggatct gcccgtggaa  480
ctgcccagac agatgttcga caatgagatc aagtcccacc tgaagtccct gccacagatg  540
gaaggcatcg acttcaacaa tgccaacgtg acctatctga tcgccgagta catgaagaga  600
gtgctggacg acgacttcca gaccttctac cagtggaacc gcaactaccg gtacatggac  660
atgcttaagg gcgagtacga cagaaagggc tccctgcagc actgcttcac cagcgtggaa  720
gagagagaag gcctctggaa agagcgggcc tccagaacag agcggtacag aaagcaggcc  780
agcaacaaga tccgcagcaa ccggcagatg agaaacgcca gcagcgaaga gatcgagaca  840
atcctggata agcggctgag caacagccgg aacgagtacc agaaaagcga gaaagtgatc  900
cggcgctaca gagtgcagga tgccctgctg tttctgctgg ccaaaaagac cctgaccgaa  960
ctggccgatt tcgacggcga gaggttcaaa ctgaaagaaa tcatgcccga cgccgagaag  1020
ggaatcctga gcgagatcat gcccatgagc ttcaccttcg agaaaggcgg caagaagtac  1080
accatcacca gcgagggcat gaagctgaag aactacggcg acttctttgt gctggctagc  1140
gacaagagga tcggcaacct gctggaactc gtgggcagcg acatcgtgtc caaagaggat  1200
atcatggaag agttcaacaa atacgaccag tgcaggcccg agatcagctc catcgtgttc  1260
aacctggaaa agtgggcctt cgacacatac cccgagctgt ctgccagagt ggaccgggaa  1320
gagaaggtgg acttcaagag catcctgctga acaacaagaa catcaacaaa  1380
gagcagagcg acatcctgcg gaagatccgg aacgccttcg atcacaacaa ttaccccgac  1440
aaaggcgtgg tggaaatcaa ggccctgcct gagatcgcca tgagcatcaa gaaggccttt  1500
ggggagtacg ccatcatgaa gggatccctt caactgcctc cacttgaaag actgacactg  1560
ggtagttcct acccatacga tgttccagat tacgcttatc cctacgacgt gcctgattat  1620
gcatacccat atgatgtccc cgactatgcc taa                                1653

SEQ ID NO: 56           moltype = DNA  length = 3174
FEATURE                 Location/Qualifiers
misc_feature            1..3174
                        note = N928-GS16-FRB-GS16 polynucleotide sequence
source                  1..3174
                        mol_type = other DNA
                        organism = synthetic construct
SEQUENCE: 56
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccacatca ggttccacgt gaacatgggc  1080
aagctgagat acctgctgaa ggccgacaag acctgcatcg acggccagac cagagtcaga  1140
gtgatcgagc agcccctgaa cggcttcggc agactggaag aggccgagac aatgcggaag  1200
caagagaacg gcaccttcgg caacagcggc atccggatca gagacttcga gaacatgaag  1260
cgggacgacg ccaatcctgc caactatccc tacatcgtgg acacctacac acactacatc  1320
ctggaaaaca acaaggtcga gatgtttatc aacgacaaag aggacagcgc ccccactgctg  1380
cccgtgatcg aggatgatag atacgtggtc aagacaatcc ccagctgccg gatgagcacc  1440
ctggaaattc cagccatggc cttccacatg tttctgttcg gcagcaagaa aaccgagaag  1500
ctgatcgtgg acgtgcacaa ccggtacaag agactgttcc aggccatgca gaaagaagaa  1560
gtgaccgccg agaatatcgc cagcttcgga atcgccgaga gcgacctgcc tcagaagatc  1620
ctggatctga tcagcggcaa tgcccacggc aaggatgtgg acgccttcat cagactgacc  1680
gtggacgaca tgctgaccga caccgagcgg agaatcaaga gattcaagga cgaccggaag  1740
tccattcgga gcgccgacaa caagatggga aagagaggct tcaagcagat ctccacaggc  1800
aagctggccg acttcctggc caaggacatc gtgctgtttc agcccagcgt gaacgatggc  1860
gagaacaaga tcaccggcct gaactaccgg atcatgcaga gcgccattgc cgtgtacgat  1920
agcggcgacg attacgaggc caagcagcag ttcaagctga tgttcgagaa ggcccggctg  1980
atcggcaagg gcacaacaga gcctcatcca tttctgtaca aggtgttcgc ccgcagcatc  2040
cccgccaatg ccgtcgagtt ctacgagcgc tacctgatcg agcggaagtt ctacctgacc  2100
ggcctgtcca acgagatcaa gaaaggcaac agagtggatg tgcccttcat ccggcgggac  2160
cagaacaagt ggaaaacacc cgccatgaag accctgggca gaatctacag cgaggatctg  2220
cccgtggaac tgcccagaca gatgttcgac aatgagatca agtcccacct gaagtccctg  2280
ccacagatgg aaggcatcga cttcaacaat gccaacgtga cctatctgat cgccgagtac  2340
```

```
atgaagagag tgctggacga cgacttccag accttctacc agtggaaccg caactaccgg  2400
tacatggaca tgcttaaggg cgagtacgac agaaagggct ccctgcagca ctgcttcacc  2460
agcgtggaag agagagaagg cctctggaaa gagcgggcct ccagaacaga gcggtacaga  2520
aagcaggcca gcaacaagat ccgcagcaac cggcagatga gaaacgccag cagcgaagag  2580
atcgagacaa tcctggataa gcggctgagc aacagccgga acgagtacca gaaaagcgag  2640
aaagtgatcc ggcgctacag agtgcaggat gccctgctgt ttctgctggc caaaaagacc  2700
ctgaccgaac tggccgattt cgacggcgag aggttcaaac tgaaagaaat catgcccgac  2760
gccgagaagg gaatcctgag cgagttcccg ggatccggag gaagtggcag ctctggcggc  2820
agtggagggt ctggtggcag cggaatcctc tggcatgaga tgtggcatga aggcctggaa  2880
gaggcatctc gtttgtactt tggggaaagg aacgtgaaag gcatgtttga ggtgctggag  2940
cccttgcatg ctatgatgga acggggcccc cagactctga aggaaacatc ctttaatcag  3000
gcctatggtc gagatttaat ggaggcccaa gagtggtgca ggaagtacat gaaatcaggg  3060
aatgtcaagg acctcaccca agcctgggac ctctattatc atgtgttccg acgaatctca  3120
aagggaggaa gcggcggttc cgggggggga tccggaagtg gttccggggg gtag        3174
```

```
SEQ ID NO: 57          moltype = DNA  length = 1044
FEATURE                Location/Qualifiers
misc_feature           1..1044
                       note = GS16-FKBP-GS16-C929 polynucleotide sequence
source                 1..1044
                       mol_type = other DNA
                       organism = synthetic construct
SEQUENCE: 57
atgggaggaa gtggcagctc tggcggcagt ggagggtctg gtggcagcgg aggagtgcag  60
gtggaaacca tctccccagg agacgggcgc accttcccca agcgcggcca gacctgcgtg  120
gtgcactaca ccgggatgct tgaagatgga aagaaatttg attcctcccg ggacagaaac  180
aagcccttta agtttatgct aggcaagcag gaggtgatcc gaggctggga agaaggggtt  240
gcccagatga gtgtgggtca gagagccaaa ctgactatat ctccagatta tgcctatggt  300
gccactgggc acccaggcat catcccacca catgccactc tcgtcttcga tgtggagctt  360
ctaaaactgg aaggaggaag cggcggttcc gggggggat ccggaagtgg ttccgggggg  420
tgtacaatca tgcccatgag cttcaccttc gagaaaggcg gcaagaagta caccatcacc  480
agcgagggca tgaagctgaa gaactacggc gacttctttg tgctggctag cgacaagagg  540
atcggcaacc tgctggaact cgtgggcagc gacatcgtgt ccaaagagga tatcatggaa  600
gagttcaaca aatacgacca gtgcaggccc gagatcagct ccatcgtgtt caacctggaa  660
aagtgggcct tcgacacata ccccgagctg tctgccagag tggaccggga agagaaggtg  720
gacttcaaga gcatcctgaa aatcctgctg aacaacaaga acatcaacaa agagcagagc  780
gacatcctgc ggaagatccg gaacgccttc gatcacaaca attaccccga caaaggcgtg  840
gtggaaatca aggccctgcc tgagatcgcc atgagcatca agaaggcctt tggggagtac  900
gccatcatga agggatccct tcaactgcct ccacttgaaa gactgacact gggtagttcc  960
tacccatacg atgttccaga ttacgcttat ccctacgacg tgcctgatta tgcataccca  1020
tatgatgtcc ccgactatgc ctaa                                         1044
```

```
SEQ ID NO: 58          moltype = DNA  length = 1377
FEATURE                Location/Qualifiers
misc_feature           1..1377
                       note = N272-GS16-pMag-GS16 polynucleotide sequence
source                 1..1377
                       mol_type = other DNA
                       organism = synthetic construct
SEQUENCE: 58
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacaacc cgggatccgg aggaagtggc  840
agctctggcg gcagtggagg gtctggtggc agcggacaca ccctgtacgc ccccggcggc  900
tacgacatca tgggctacct gagacagatc agaaacagac ccaaccccca ggtggagctg  960
ggccccgtgg acaccagctg cgccctgatc ctgtgcgacc tgaagcagaa ggacaccccc  1020
atcgtgtacg ccagcgaggc cttcctgtat atgaccggct acagcaacgc cgaggtgctg  1080
ggcagaaact gcagattcct gcagagcccc gacggcatgg tgaagcccaa gagcaccaga  1140
aagtacgtgg acagcaacac catcaacacc atcagaaagg ccatcgacag aaacgccgag  1200
gtgcaggtgg aggtggtgaa cttcaagaag aacggccaga gattcgtgaa cttcctgacc  1260
atcatccccg tgagagacga gaccggcgag tacagataca gcatgggctt ccagtgcgag  1320
accgagggag gaagcggcgg ttccgggggg ggatccggaa gtggttccgg ggggtag     1377
```

```
SEQ ID NO: 59          moltype = DNA  length = 3141
FEATURE                Location/Qualifiers
misc_feature           1..3141
                       note = GS16-nMag-GS16-C273 polynucleotide sequence
source                 1..3141
```

```
                        mol_type = other DNA
                        organism = synthetic construct
SEQUENCE: 59
atgggaggaa gtggcagctc tggcggcagt ggagggtctg gtggcagcgg acacaccctg  60
tacgcccccg gcggctacga catcatgggc tacctggacc agatcggcaa cagacccaac  120
ccccaggtgg agctgggccc cgtggacacc agctgcgccc tgatcctgtg cgacctgaag  180
cagaaggaca cccccatcgt gtacgccagc gaggccttcc tgtatatgac cggctacagc  240
aacgccgagg tgctgggcag aaactgcaga ttcctgcaga gccccgacgg catggtgaag  300
cccaagagca ccagaaagta cgtggacagc aacaccatca acaccatgag aaaggccatc  360
gacagaaacg ccgaggtgca ggtggaggtg gtgaacttca agaagaacgg ccagagattc  420
gtgaacttcc tgaccatgat ccccgtgaga gacgagaccg gcgagtacag atacagcatg  480
ggcttccagt gcgagaccga gggaggaagc ggcggttccg gggggggatc cggaagtggt  540
tccgggggt gtacaagcat caagctgccc aaggaccgga tccacagcga gaagtccaac  600
aagagcgtgg ccatggatat gctcaacgaa gtgaagcggt gccccgacga gctgttcaca  660
acactgtctg ccgagaagca gtcccggttc agaatcatca gcgacgacca caatgaagtg  720
ctgatgaagc ggagcagcga cagattcgtg cctctgctgc tgcagtatat cgattacggc  780
aagctgttcg accacatcag gttccacgtg aacatgggca agctgagata cctgctgaag  840
gccgacaaga cctgcatcga cggccagacc agagtcagag tgatcgagca gcccctgaac  900
ggcttcggca gactggaaga ggccgagaca atgcggaagc aagagaacgg caccttcggc  960
aacagcggca tccggatcag agacttcgag aacatgaagc gggacgacgc caatcctgcc  1020
aactatccct acatcgtgga cacctacaca cactacatcc tggaaaacaa caaggtcgag  1080
atgtttatca acgacaaaga ggacagcgcc ccactgctgc ccgtgatcga ggatgataga  1140
tacgtggtca agacaatccc cagctgccgg atgagcaccc tggaaattcc agccatggcc  1200
ttccacatgt ttctgttcgg cagcaagaaa accgagaagc tgatcgtgga cgtgcacaac  1260
cggtacaaga gactgttcca ggccatgcag aaagaagaag tgaccgccga gaatatcgcc  1320
agcttcggaa tcgccgagag cgacctgcct cagaagatcc tggatctgat cagcggcaat  1380
gcccacggca aggatgtgga cgccttcatc agactgaccg tggacgacat gctgaccgac  1440
accgagcgga gaatcaagag attcaaggac gaccggaagt ccattcggag cgccgacaac  1500
aagatgggaa agagaggctt caagcagatc tccacaggca agctggccga cttcctggcc  1560
aaggacatcg tgctgtttca gcccagcgtg aacgatggcg agaacaagat caccggcctg  1620
aactaccgga tcatgcagag cgccattgcc gtgtacgata gcggcgacga ttacgaggcc  1680
aagcagcagt tcaagctgat gttcgagaag gcccggctga tcggcaaggg cacaacagag  1740
cctcatccat ttctgtacaa ggtgttcgcc cgcagcatcc ccgccaatgc cgtcgagttc  1800
tacgagcgct acctgatcga gcggaagttc tacctgaccg gcctgtccaa cgagatcaag  1860
aaaggcaaca gagtggatgt gcccttcatc cggcgggacc agaacaagtg gaaaacaccc  1920
gccatgaaga ccctgggcag aatctacagc gaggatctgc ccgtggaact gcccagacag  1980
atgttcgaca atgagatcaa gtcccacctg aagtccctgc cacagatgga aggcatcgac  2040
ttcaacaatg ccaacgtgac ctatctgatc gccgagtaca tgaagagagt gctggacgac  2100
gacttccaga ccttctacca gtggaaccgc aactaccggt acatggacat gcttaagggc  2160
gagtacgaca gaaagggctc cctgcagcac tgcttcacca gcgtggaaga gagagaaggc  2220
ctctggaaag agcgggcctc cagaacagag cggtacagaa agcaggccag caacaagatc  2280
cgcagcaacc ggcagatgag aaacgccagc agcgaagaga tcgagacaat cctggataag  2340
cggctgagca acagccggaa cgagtaccag aaaagcgaga aagtgatccg gcgctacaga  2400
gtgcaggatg ccctgctgtt tctgctggcc aaaaagaccc tgaccgaact ggccgatttc  2460
gacggcgaga ggttcaaact gaaagaaatc atgcccgacg ccgagaaggg aatcctgagc  2520
gagatcatgc ccatgagctt caccttcgag aaaggcggca agaagtacac catcaccagc  2580
gagggcatga agctgaagaa ctacggcgac ttctttgtgc tggctagcga caagaggatc  2640
ggcaacctgc tggaactcgt gggcagcgac atcgtgtcca aagaggatat catggaagag  2700
ttcaacaaat acgaccagtg caggcccgag atcagctcca tcgtgttcaa cctggaaaag  2760
tgggccttcg acacataccc cgagctgtct gccagagtgg accgggaaga gaaggtggac  2820
ttcaagagca tcctgaaaat cctgctgaac aacaagaaca tcaacaaaga gcagagcgac  2880
atcctgcgga agatccggaa cgccttcgat cacaacaatt accccgacaa aggcgtggtg  2940
gaaatcaagg ccctgcctga gatcgccatg agcatcaaga aggcctttgg ggagtacgcc  3000
atcatgaagg gatcccttca actgcctcca cttgaaagac tgacactggg tagttcctac  3060
ccatacgatg ttccagatta cgcttatccc tacgacgtgc ctgattatgc atacccatat  3120
gatgtccccg actatgccta a                                           3141

SEQ ID NO: 60           moltype = DNA  length = 1419
FEATURE                 Location/Qualifiers
misc_feature            1..1419
                        note = N286-GS16- pMag -GS16 polynucleotide sequence
source                  1..1419
                        mol_type = other DNA
                        organism = synthetic construct
SEQUENCE: 60
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
```

-continued

```
atccacagcg agaagtccaa cccgggatcc ggaggaagtg gcagctctgg cggcagtgga  900
gggtctggtg gcagcggaca caccctgtac gccccggcg gctacgacat catgggctac  960
ctgagacaga tcagaaacag acccaacccc caggtggagc tgggccccgt ggacaccagc  1020
tgcgccctga tcctgtgcga cctgaagcag aaggacaccc ccatcgtgta cgccagcgag  1080
gccttcctgt atatgaccgg ctacagcaac gccgaggtgc tgggcagaaa ctgcagattc  1140
ctgcagagcc ccgacggcat ggtgaagccc aagagcacca gaaagtacgt ggacagcaac  1200
accatcaaca ccatcagaaa ggccatcgac agaaacgccg aggtgcaggt ggaggtggtg  1260
aacttcaaga agaacggcca gagattcgtg aacttcctga ccatcatccc cgtgagagac  1320
gagaccggcg agtacagata cagcatgggc ttccagtgcg agaccgaggg aggaagcggc  1380
ggttccgggg ggggatccgg aagtggttcc gggggtag                        1419
```

```
SEQ ID NO: 61           moltype = DNA  length = 3099
FEATURE                 Location/Qualifiers
misc_feature            1..3099
                        note = GS16- nMag -GS16-C287 polynucleotide sequence
source                  1..3099
                        mol_type = other DNA
                        organism = synthetic construct
SEQUENCE: 61
atgggaggaa gtggcagctc tggcggcagt ggagggtctg gtggcagcgg acacaccctg  60
tacgcccccg gcggctacga catcatgggc tacctggacc agatcggcaa cagacccaac  120
ccccaggtgg agctgggccc cgtggacacc agctgcgccc tgatcctgtg cgacctgaag  180
cagaaggaca cccccatcgt gtacgccagc gaggccttcc tgtatatgac cggctacagc  240
aacgccgagg tgctgggcag aaactgcaga ttcctgcaga gccccgacgg catggtgaag  300
cccaagagca ccagaaagta cgtggacagc aacaccatca acaccatgag aaaggccatc  360
gacagaaacg ccgaggtgca ggtggaggtg gtgaacttca agaagaacgg ccagagattc  420
gtgaacttcc tgaccatgat ccccgtgaga gacgagaccg gcgagtacag atacagcatg  480
ggcttccagt gcgagaccga gggaggaagc ggcggttccg gggggggatc cggaagtggt  540
tccgggggt gtacaaacaa gagcgtggcc atggatatgc tcaacgaagt gaagcggtgc  600
cccgacgagc tgttcacaac actgtctgcc gagaagcagt cccggttcag aatcatcagc  660
gacgaccaca atgaagtgct gatgaagcgg agcagcgaca gattcgtgcc tctgctgctg  720
cagtatatcg attacggcaa gctgttcgac cacatcaggt tccacgtgaa catgggcaag  780
ctgagatacc tgctgaaggc cgacaagacc tgcatcgacg gccagaccag agtcagagtg  840
atcgagcagc ccctgaacgg cttcggcaga ctggaagagg ccgagacaat gcggaagcaa  900
gagaacggca ccttcggcaa cagcggcatc cggatcagag acttcgagaa catgaagcgg  960
gacgacgcca atcctgccaa ctatccctac atcgtggaca cctacacaca ctacatcctg  1020
gaaaacaaca aggtcgagat gtttatcaac gacaaagagg acagcgcccc actgctgccc  1080
gtgatcgagg atgatagata cgtggtcaag acaatcccca gctgccggat gagcaccctg  1140
gaaattccag ccatggcctt ccacatgttt ctgttcggca gcaagaaaac cgagaagctg  1200
atcgtggacg tgcacaaccg gtacaagaga ctgttccagg ccatgcagaa agaagaagtg  1260
accgccgaga atatcgccag cttcggaatc gccgagagcg acctgcctca gaagatcctg  1320
gatctgatca gcggcaatgc ccacggcaag gatgtggacg ccttcatcag actgaccgtg  1380
gacgacatgc tgaccgacac cgagcggaga atcaagagat tcaaggacga ccggaagtcc  1440
attcggagcg ccgacaacaa gatgggaaag agaggcttca agcagatctc cacaggcaag  1500
ctggccgact tcctggccaa ggacatcgtg ctgtttcagc ccagcgtgaa cgatggcgag  1560
aacaagatca ccggcctgaa ctaccggatc atgcagagcg ccattgccgt gtacgatagc  1620
ggcgacgatt acgaggccaa gcagcagttc aagctgatgt tcgagaaggc ccggctgatc  1680
ggcaagggca caacagagcc tcatccattt ctgtacaagg tgttcgcccg cagcatcccc  1740
gccaatgccg tcgagttcta cgagcgctac ctgatcgagc ggaagttcta cctgaccggc  1800
ctgtccaacg agatcaagaa aggcaacaga gtggatgtgc ccttcatccg gcgggaccag  1860
aacaagtgga aaacacccgc catgaagacc ctgggcagaa tctacagcga ggatctgccc  1920
gtggaactgc ccagacagat gttcgacaat gagatcaagt cccacctgaa gtccctgcca  1980
cagatggaag gcatcgactt caacaatgcc aacgtgacct atctgatcgc cgagtacatg  2040
aagagagtgc tggacgacga cttccagacc ttctaccagt ggaaccgcaa ctaccggtac  2100
atggacatgc ttaagggcga gtacgacaga aagggctccc tgcagcactg cttcaccagc  2160
gtggaagaga gagaaggcct ctggaaagag cgggcctcca gaacagagcg gtacagaaag  2220
caggccagca acaagatccg cagcaaccgg cagatgagaa acgccagcag cgaagagatc  2280
gagacaatcc tggataagcg gctgagcaac agccggaacg agtaccagaa aagcgagaaa  2340
gtgatccggc gctacagagt gcaggatgcc ctgctgtttc tgctggccaa aaagaccctg  2400
accgaactgg ccgatttcga cggcgagagg ttcaaactga aagaaatcat gcccgacgcc  2460
gagaagggaa tcctgagcga gatcatgccc atgagcttca ccttcgagaa aggcggcaag  2520
aagtacacca tcaccagcga gggcatgaag ctgaagaact acggcgactt ctttgtgctg  2580
gctagcgaca agaggatcgg caacctgctg gaactcgtgg gcagcgacat cgtgtccaaa  2640
gaggatatca tggaagagtt caacaaatac gaccagtgca ggcccgagat cagctccatc  2700
gtgttcaacc tggaaaagtg ggccttcgac acataccccg agctgtctgc cagagtggac  2760
cgggaagaga aggtggactt caagagcatc ctgaaaatcc tgctgaacaa caagaacatc  2820
aacaaagagc agagcgacat cctgcggaag atccggaacg ccttcgatca caacaattac  2880
cccgacaaag gcgtggtgga aatcaaggcc ctgcctgaga tcgccatgag catcaagaag  2940
gcctttgggg agtacgccat catgaaggga tcccttcaac tgcctccact tgaaagactg  3000
acactgggta gttcctaccc atacgatgtt ccagattacg cttatcccta cgacgtgcct  3060
gattatgcat acccatatga tgtccccgac tatgcctaa                        3099
```

```
SEQ ID NO: 62           moltype = DNA  length = 1614
FEATURE                 Location/Qualifiers
misc_feature            1..1614
                        note = N351-GS16- pMag -GS16 polynucleotide sequence
source                  1..1614
                        mol_type = other DNA
                        organism = synthetic construct
```

```
SEQUENCE: 62
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccttccgg gatccggagg aagtggcagc  1080
tctggcggca gtggagggtc tggtggcagc ggacacaccc tgtacgcccc cggcggctac  1140
gacatcatgg gctacctgag acagatcaga aacagaccca acccccaggt ggagctgggc  1200
cccgtggaca ccagctgcgc cctgatcctg tgcgacctga agcagaagga cacccccatc  1260
gtgtacgcca gcgaggcctt cctgtatatg accggctaca gcaacgccga ggtgctgggc  1320
agaaactgca gattcctgca gagccccgac ggcatggtga agcccaagag caccagaaag  1380
tacgtggaca gcaacaccat caacaccatc agaaaggcca tcgacagaaa cgccgaggtg  1440
caggtggagg tggtgaactt caagaagaac ggccagagat tcgtgaactt cctgaccatc  1500
atccccgtga gagacgagac cggcgagtac agatacagca tgggcttcca gtgcgagacc  1560
gagggaggaa gcggcggttc cggggggga tccggaagtg gttccggggg gtag  1614
```

```
SEQ ID NO: 63           moltype = DNA  length = 2904
FEATURE                 Location/Qualifiers
misc_feature            1..2904
                        note = GS16- nMag -GS16-C352 polynucleotide sequence
source                  1..2904
                        mol_type = other DNA
                        organism = synthetic construct
SEQUENCE: 63
atgggaggaa gtggcagctc tggcggcagt ggagggtctg gtggcagcgg acacaccctg  60
tacgcccccg gcggctacga catcatgggc tacctggacc agatcggcaa cagacccaac  120
ccccaggtgg agctgggccc cgtggacacc agctgcgccc tgatcctgtg cgacctgaag  180
cagaaggaca cccccatcgt gtacgccagc gaggccttcc tgtatatgac cggctacagc  240
aacgccgagg tgctgggcag aaactgcaga ttcctgcaga gccccgacgg catggtgaag  300
cccaagagca ccagaaagta cgtggacagc aacaccatca acaccatgag aaaggccatc  360
gacagaaacg ccgaggtgca ggtggaggtg gtgaacttca agaagaacgg ccagagattc  420
gtgaacttcc tgaccatgat ccccgtgaga gacgagaccg gcgagtacag atacagcatg  480
ggcttccagt gcgagaccga gggaggaagc ggcggttccg gggggggatc cggaagtggt  540
tccgggggt gtacacacat caggttccac gtgaacatgg gcaagctgag atacctgctg  600
aaggccgaca agacctgcat cgacggccag accagagtca gagtgatcga gcagcccctg  660
aacggcttcg gcagactgga agaggccgag acaatgcgga agcaagagaa cggcaccttc  720
ggcaacagcg gcatccggat cagagacttc gagaacatga agcgggacga cgccaatcct  780
gccaactatc cctacatcgt ggacacctac acacactaca tcctggaaaa caacaaggtc  840
gagatgttta tcaacgacaa agaggacagc gccccactgc tgcccgtgat cgaggatgat  900
agatacgtgg tcaagacaat ccccagctgc cggatgagca ccctggaaat tccagccatg  960
gccttccaca tgtttctgtt cggcagcaag aaaaccgaga agctgatcgt ggacgtgcac  1020
aaccggtaca agagactgtt ccaggccatg cagaaagaag aagtgaccgc cgagaatatc  1080
gccagcttcg gaatcgccga gagcgacctg cctcagaaga tcctggatct gatcagcggc  1140
aatgcccacg gcaaggatgt ggacgccttc atcagactga ccgtggacga catgctgacc  1200
gacaccgagc ggagaatcaa gagattcaag gacgaccgga agtccattcg gagcgccgac  1260
aacaagatgg gaaagagagg cttcaagcag atctccacag gcaagctggc cgacttcctg  1320
gccaaggaca tcgtgctgtt tcagcccagc gtgaacgatg gcgagaacaa gatcaccggc  1380
ctgaactacc ggatcatgca gagcgccatt gccgtgtacg atagcggcga cgattacgag  1440
gccaagcagc agttcaagct gatgttcgag aaggcccggc tgatcggcaa gggcacaaca  1500
gagcctcatc catttctgta caaggtgttc gcccgcagca tccccgccaa tgccgtcgag  1560
ttctacgagc gctacctgat cgagcggaag ttctacctga ccggcctgtc caacgagatc  1620
aagaaaggca acagagtgga tgtgcccttc atccggcggg accagaacaa gtggaaaaca  1680
cccgccatga agaccctggg cagaatctac agcgaggatc tgcccgtgga actgcccaga  1740
cagatgttcg acaatgagat caagtcccac ctgaagtccc tgccacagat ggaaggcatc  1800
gacttcaaca atgccaacgt gacctatctg atcgccgagt acatgaagag agtgctggac  1860
gacgacttcc agaccttcta ccagtggaac cgcaactacc ggtacatgga catgcttaag  1920
ggcgagtacg acagaaaggg ctccctgcag cactgcttca ccagcgtgga agagagagaa  1980
ggcctctgga aagagcgggc ctccagaaca gagcggtaca gaaagcaggc cagcaacaag  2040
atccgcagca accggcagat gagaaacgcc agcagcgaag agatcgagac aatcctggat  2100
aagcggctga gcaacagccg gaacgagtac cagaaaagcg agaaagtgat ccggcgctac  2160
agagtgcagg atgccctgct gtttctgctg gccaaaaaga ccctgaccga actggccgat  2220
ttcgacggcg agaggttcaa actgaaagaa atcatgcccg acgccgagaa gggaatcctg  2280
agcgagatca tgcccatgag cttcaccttc gagaaaggcg gcaagaagta caccatcacc  2340
agcgagggca tgaagctgaa gaactacggc gacttctttg tgctggctag cgacaagagg  2400
atcggcaacc tgctggaact cgtgggcagc gacatcgtgt ccaaagagga tatcatggaa  2460
gagttcaaca aatacgacca gtgcaggccc gagatcagct ccatcgtgtt caacctggaa  2520
```

```
aagtgggcct tcgacacata ccccgagctg tctgccagag tggaccggga agagaaggtg  2580
gacttcaaga gcatcctgaa aatcctgctg aacaacaaga acatcaacaa agagcagagc  2640
gacatcctgc ggaagatccg gaacgccttc gatcacaaca attaccccga caaaggcgtg  2700
gtggaaatca aggccctgcc tgagatcgcc atgagcatca agaaggcctt tggggagtac  2760
gccatcatga agggatccct tcaactgcct ccacttgaaa gactgacact gggtagttcc  2820
tacccatacg atgttccaga ttacgcttat ccctacgacg tgcctgatta tgcataccca  2880
tatgatgtcc ccgactatgc ctaa                                           2904

SEQ ID NO: 64            moltype = DNA  length = 2001
FEATURE                  Location/Qualifiers
misc_feature             1..2001
                         note = N480-GS16- pMag -GS16 polynucleotide sequence
source                   1..2001
                         mol_type = other DNA
                         organism = synthetic construct
SEQUENCE: 64
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccacatca ggttccacgt gaacatgggc  1080
aagctgagat acctgctgaa ggccgacaag acctgcatcg acggccagac cagagtcaga  1140
gtgatcgagc agcccctgaa cggcttcggc agactggaag aggccgagac aatgcggaag  1200
caagagaacg gcaccttcgg caacagcggc atccggatca gagacttcga gaacatgaag  1260
cgggacgacg ccaatcctgc caactatccc tacatcgtgg acacctacac acactacatc  1320
ctggaaaaca acaaggtcga gatgtttatc aacgacaaag aggacagcgc cccactgctg  1380
cccgtgatcg aggatgatag atacgtggtc aagacaatcc ccagctgccg gatgagcacc  1440
cttccgggat ccggaggaag tggcagctct ggcggcagtg gagggtctgg tggcagcgga  1500
cacaccctgt acgcccccgg cggctacgac atcatgggct acctgagaca gatcagaaac  1560
agacccaacc cccaggtgga gctgggcccc gtggacacca gctgcgccct gatcctgtgc  1620
gacctgaagc agaaggacac ccccatcgtg tacgccagcg aggccttcct gtatatgacc  1680
ggctacagca acgccgaggt gctgggcaga aactgcagat tcctgcagag ccccgacggc  1740
atggtgaagc ccaagagcac cagaaagtac gtggacagca acaccatcaa caccatcaga  1800
aaggccatcg acagaaacgc cgaggtgcag gtggaggtgg tgaacttcaa gaagaacggc  1860
cagagattcg tgaacttcct gaccatcatc cccgtgagag acgagaccgg cgagtacaga  1920
tacagcatgg gcttccagtg cgagaccgag ggaggaagcg gcggttccgg ggggggatcc  1980
ggaagtggtt ccggggggta g                                              2001

SEQ ID NO: 65            moltype = DNA  length = 2517
FEATURE                  Location/Qualifiers
misc_feature             1..2517
                         note = GS16- nMag -GS16-C481 polynucleotide sequence
source                   1..2517
                         mol_type = other DNA
                         organism = synthetic construct
SEQUENCE: 65
atgggaggaa gtggcagctc tggcggcagt ggagggtctg gtggcagcgg acacaccctg  60
tacgcccccg gcggctacga catcatgggc tacctggacc agatcggcaa cagacccaac  120
ccccaggtgg agctgggccc cgtggacacc agctgcgccc tgatcctgtg cgacctgaag  180
cagaaggaca cccccatcgt gtacgccagc gaggccttcc tgtatatgac cggctacagc  240
aacgccgagg tgctgggcag aaactgcaga ttcctgcaga gccccgacgg catggtgaag  300
cccaagagca ccagaaagta cgtggacagc aacaccatca acaccatgag aaaggccatc  360
gacagaaacg ccgaggtgca ggtggaggtg gtgaacttca agaagaacgg ccagagattc  420
gtgaacttcc tgaccatgat ccccgtgaga gacgagaccg gcgagtacag atacagcatg  480
ggcttccagt gcgagaccga gggaggaagc ggcggttccg gggggggatc cggaagtggt  540
tccggggggt gtacactgga aattccagcc atggccttcc acatgtttct gttcggcagc  600
aagaaaaccg agaagctgat cgtggacgtg cacaaccggt acaagagact gttccaggcc  660
atgcagaaag aagaagtgac cgccgagaat atcgccagct tcggaatcgc cgagagcgac  720
ctgcctcaga agatcctgga tctgatcagc ggcaatgccc acggcaagga tgtggacgcc  780
ttcatcagac tgaccgtgga cgacatgctg accgacaccg agcggagaat caagagattc  840
aaggacgacc ggaagtccat tcggagcgcc gacaacaaga tgggaaagag aggcttcaag  900
cagatctcca caggcaagct ggccgacttc ctggccaagg acatcgtgct gtttcagccc  960
agcgtgaacg atggcgagaa caagatcacc ggcctgaact accggatcat gcagagcgcc  1020
attgccgtgt acgatagcgg cgacgattac gaggccaagc agcagttcaa gctgatgttc  1080
gagaaggccc ggctgatcgg caagggcaca acagagcctc atccatttct gtacaaggtg  1140
ttcgcccgca gcatccccgc caatgccgtc gagttctacg agcgctacct gatcgagcgg  1200
```

```
aagttctacc tgaccggcct gtccaacgag atcaagaaag gcaacagagt ggatgtgccc  1260
ttcatccggc gggaccagaa caagtggaaa acacccgcca tgaagaccct gggcagaatc  1320
tacagcgagg atctgcccgt ggaactgccc agacagatgt tcgacaatga gatcaagtcc  1380
cacctgaagt ccctgccaca gatggaaggc atcgacttca acaatgccaa cgtgacctat  1440
ctgatcgccg agtacatgaa gagagtgctg gacgacgact tccagacctt ctaccagtgg  1500
aaccgcaact accggtacat ggacatgctt aagggcgagt acgacagaaa gggctccctg  1560
cagcactgct tcaccagcgt ggaagagaga gaaggcctct ggaaagagcg ggcctccaga  1620
acagagcggt acagaaagca ggccagcaac aagatccgca gcaaccggca gatgagaaac  1680
gccagcagcg aagagatcga gacaatcctg gataagcggc tgagcaacag ccggaacgag  1740
taccagaaaa gcgagaaagt gatccggcgc tacagagtgc aggatgccct gctgtttctg  1800
ctggccaaaa agaccctgac cgaactggcc gatttcgacg gcgagaggtt caaactgaaa  1860
gaaatcatgc ccgacgccga gaagggaatc ctgagcgaga tcatgcccat gagcttcacc  1920
ttcgagaaag gcggcaagaa gtacaccatc accagcgagg gcatgaagct gaagaactac  1980
ggcgacttct ttgtgctggc tagcgacaag aggatcggca acctgctgga actcgtgggc  2040
agcgacatcg tgtccaaaga ggatatcatg gaagagttca acaaatacga ccagtgcagg  2100
cccgagatca gctccatcgt gttcaacctg gaaaagtggg ccttcgacac ataccccgag  2160
ctgtctgcca gagtggaccg ggaagagaag gtggacttca agagcatcct gaaaatcctg  2220
ctgaacaaca agaacatcaa caaagagcag agcgacatcc tgcggaagat ccggaacgcc  2280
ttcgatcaca acaattaccc cgacaaaggc gtggtggaaa tcaaggccct gcctgagatc  2340
gccatgagca tcaagaaggc ctttggggag tacgccatca tgaagggatc ccttcaactg  2400
cctccacttg aaagactgac actgggtagt tcctacccat acgatgttcc agattacgct  2460
tatccctacg acgtgcctga ttatgcatac ccatatgatg tccccgacta tgcctaa     2517
```

```
SEQ ID NO: 66          moltype = DNA  length = 2211
FEATURE                Location/Qualifiers
misc_feature           1..2211
                       note = N550-GS16- pMag -GS16 polynucleotide sequence
source                 1..2211
                       mol_type = other DNA
                       organism = synthetic construct
SEQUENCE: 66
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccacatca ggttccacgt gaacatgggc  1080
aagctgagat acctgctgaa ggccgacaag acctgcatcg acggccagac cagagtcaga  1140
gtgatcgagc agcccctgaa cggcttcggc agactggaag aggccgagac aatgcggaag  1200
caagagaacg gcaccttcgg caacagcggc atccggatca gagacttcga gaacatgaag  1260
cgggacgacg ccaatcctgc caactatccc tacatcgtgg acacctacac acactacatc  1320
ctggaaaaca acaaggtcga gatgtttatc aacgacaaag aggacagcgc ccccactgctg  1380
cccgtgatcg aggatgatag atacgtggtc aagacaatcc ccagctgccg gatgagcacc  1440
ctggaaattc cagccatggc cttccacatg tttctgttcg gcagcaagaa aaccgagaag  1500
ctgatcgtgg acgtgcacaa ccggtacaag agactgttcc aggccatgca gaaagaagaa  1560
gtgaccgccg agaatatcgc cagcttcgga atcgccgaga gcgacctgcc tcagaagatc  1620
ctggatctga tcagcggcaa tgcccacggc ttcccgggat ccggaggaag tggcagctct  1680
ggcggcagtg gagggtctgg tggcagcgga cacaccctgt acgcccccgg cggctacgac  1740
atcatgggct acctgagaca gatcagaaac agacccaacc cccaggtgga gctgggcccc  1800
gtggacacca gctgcgccct gatcctgtgc gacctgaagc agaaggacac ccccatcgtg  1860
tacgccagcg aggccttcct gtatatgacc ggctacagca acgccgaggt gctgggcaga  1920
aactgcagat tcctgcagag ccccgacggc atggtgaagc ccaagagcac cagaaagtac  1980
gtggacagca acaccatcaa caccatcaga aaggccatcg acagaaacgc cgaggtgcag  2040
gtggaggtgg tgaacttcaa gaagaacggc cagagattcg tgaacttcct gaccatcatc  2100
cccgtgagag acgagaccgg cgagtacaga tacagcatgg gcttccagtg cgagaccgag  2160
ggaggaagcg gcggttccgg ggggggatcc ggaagtggtt ccggggggta g             2211
```

```
SEQ ID NO: 67          moltype = DNA  length = 2307
FEATURE                Location/Qualifiers
misc_feature           1..2307
                       note = GS16- nMag -GS16-C551 polynucleotide sequence
source                 1..2307
                       mol_type = other DNA
                       organism = synthetic construct
SEQUENCE: 67
atgggaggaa gtggcagctc tggcggcagt ggagggtctg gtggcagcgg acacaccctg  60
tacgcccccg gcggctacga catcatgggc tacctggacc agatcggcaa cagacccaac  120
```

```
ccccaggtgg agctgggccc cgtggacacc agctgcgccc tgatcctgtg cgacctgaag  180
cagaaggaca cccccatcgt gtacgccagc gaggccttcc tgtatatgac cggctacagc  240
aacgccgagg tgctgggcag aaactgcaga ttcctgcaga gccccgacgg catggtgaag  300
cccaagagca ccagaaagta cgtggacagc aacaccatca acaccatgag aaaggccatc  360
gacagaaacg ccgaggtgca ggtggaggtg gtgaacttca agaagaacgg ccagagattc  420
gtgaacttcc tgaccatgat ccccgtgaga gacgagaccg gcgagtacag atacagcatg  480
ggcttccagt gcgagaccga gggaggaagc ggcggttccg ggggggggatc cggaagtggt  540
tccggggggt gtacaaagga tgtggacgcc ttcatcagac tgaccgtgga cgacatgctg  600
accgacaccg agcggagaat caagagattc aaggacgacc ggaagtccat tcggagcgcc  660
gacaacaaga tgggaaagag aggcttcaag cagatctcca caggcaagct ggccgacttc  720
ctggccaagg acatcgtgct gtttcagccc agcgtgaacg atggcgagaa caagatcacc  780
ggcctgaact accggatcat gcagagcgcc attgccgtgt acgatagcgg cgacgattac  840
gaggccaagc agcagttcaa gctgatgttc gagaaggccc ggctgatcgg caagggcaca  900
acagagcctc atccatttct gtacaaggtg ttcgcccgca gcatccccgc caatgccgtc  960
gagttctacg agcgctacct gatcgagcgg aagttctacc tgaccggcct gtccaacgag  1020
atcaagaaag gcaacagagt ggatgtgccc ttcatccggc gggaccagaa caagtggaaa  1080
acacccgcca tgaagaccct gggcagaatc tacagcgagg atctgcccgt ggaactgccc  1140
agacagatgt tcgacaatga gatcaagtcc cacctgaagt ccctgccaca gatggaaggc  1200
atcgacttca acaatgccaa cgtgacctat ctgatcgccg agtacatgaa gagagtgctg  1260
gacgacgact tccagacctt ctaccagtgg aaccgcaact accggtacat ggacatgctt  1320
aagggcgagt acgacagaaa gggctccctg cagcactgct tcaccagcgt ggaagagaga  1380
gaaggcctct ggaaagagcg ggcctccaga acagagcggt acagaaagca ggccagcaac  1440
aagatccgca gcaaccggca gatgagaaac gccagcagcg aagagatcga gacaatcctg  1500
gataagcggc tgagcaacag ccggaacgag taccagaaaa gcgagaaagt gatccggcgc  1560
tacagagtgc aggatgccct gctgtttctg ctggccaaaa agaccctgac cgaactggcc  1620
gatttcgacg gcgagaggtt caaactgaaa gaaatcatgc ccgacgccga gaagggaatc  1680
ctgagcgaga tcatgcccat gagcttcacc ttcgagaaag gcggcaagaa gtacaccatc  1740
accagcgagg gcatgaagct gaagaactac ggcgacttct ttgtgctggc tagcgacaag  1800
aggatcggca acctgctgga actcgtgggc agcgacatcg tgtccaaaga ggatatcatg  1860
gaagagttca acaaatacga ccagtgcagg cccgagatca gctccatcgt gttcaacctg  1920
gaaaagtggg ccttcgacac ataccccgag ctgtctgcca gagtggaccg ggaagagaag  1980
gtggacttca agagcatcct gaaaatcctg ctgaacaaca agaacatcaa caaagagcag  2040
agcgacatcc tgcggaagat ccggaacgcc ttcgatcaca acaattaccc cgacaaaggc  2100
gtggtggaaa tcaaggccct gcctgagatc gccatgagca tcaagaaggc ctttggggag  2160
tacgccatca tgaagggatc ccttcaactg cctccacttg aaagactgac actgggtagt  2220
tcctacccat acgatgttcc agattacgct tatccctacg acgtgcctga ttatgcatac  2280
ccatatgatg tccccgacta tgcctaa                                    2307
```

```
SEQ ID NO: 68           moltype = DNA  length = 2433
FEATURE                 Location/Qualifiers
misc_feature            1..2433
                        note = N624-GS16- pMag -GS16 polynucleotide sequence
source                  1..2433
                        mol_type = other DNA
                        organism = synthetic construct
SEQUENCE: 68
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccacatca ggttccacgt gaacatgggc  1080
aagctgagat acctgctgaa ggccgacaag acctgcatcg acggccagac cagagtcaga  1140
gtgatcgagc agcccctgaa cggcttcggc agactggaag aggccgagac aatgcggaag  1200
caagagaacg gcaccttcgg caacagcggc atccggatca gagacttcga gaacatgaag  1260
cgggacgacg ccaatcctgc caactatccc tacatcgtgg acacctacac acactacatc  1320
ctggaaaaca acaaggtcga gatgtttatc aacgacaaag aggacagcgc cccactgctg  1380
cccgtgatcg aggatgatag atacgtggtc aagacaatcc ccagctgccg gatgagcacc  1440
ctggaaattc cagccatggc cttccacatg tttctgttcg gcagcaagaa aaccgagaag  1500
ctgatcgtgg acgtgcacaa ccggtacaag agactgttcc aggccatgca gaaagaagaa  1560
gtgaccgccg agaatatcgc cagcttcgga atcgccgaga gcgacctgcc tcagaagatc  1620
ctggatctga tcagcggcaa tgcccacggc aaggatgtgg acgccttcat cagactgacc  1680
gtggacgaca tgctgaccga caccgagcgg agaatcaaga gattcaagga cgaccggaag  1740
tccattcgga gcgccgacaa caagatggga aagagaggct tcaagcagat ctccacaggc  1800
aagctggccg acttcctggc caaggacatc gtgctgtttc agcccagcgt gaacgatggc  1860
gagaacaaga tcaacccggg atccggagga agtggcagct ctggcggcag tggagggtct  1920
ggtggcagcg gacacaccct gtacgccccc ggcggctacg acatcatggg ctacctgaga  1980
```

```
cagatcagaa acagacccaa cccccaggtg gagctgggcc ccgtggacac cagctgcgcc  2040
ctgatcctgt gcgacctgaa gcagaaggac acccccatcg tgtacgccag cgaggccttc  2100
ctgtatatga ccggctacag caacgccgag gtgctgggca gaaactgcag attcctgcag  2160
agccccgacg gcatggtgaa gcccaagagc accagaaagt acgtggacag caacaccatc  2220
aacaccatca gaaaggccat cgacagaaac gccgaggtgc aggtggaggt ggtgaacttc  2280
aagaagaacg gccagagatt cgtgaacttc ctgaccatca tccccgtgag agacgagacc  2340
ggcgagtaca gatacagcat gggcttccag tgcgagaccg agggaggaag cggcggttcc  2400
gggggggat ccggaagtgg ttccgggggg tag                               2433

SEQ ID NO: 69          moltype = DNA  length = 2085
FEATURE                Location/Qualifiers
misc_feature           1..2085
                       note = GS16- nMag -GS16-C625 polynucleotide sequence
source                 1..2085
                       mol_type = other DNA
                       organism = synthetic construct
SEQUENCE: 69
atgggaggaa gtggcagctc tggcggcagt ggagggtctg gtggcagcgg acacaccctg  60
tacgcccccg gcggctacga catcatgggc tacctggacc agatcggcaa cagacccaac  120
ccccaggtgg agctgggccc cgtggacacc agctgcgccc tgatcctgtg cgacctgaag  180
cagaaggaca cccccatcgt gtacgccagc gaggccttcc tgtatatgac cggctacagc  240
aacgccgagg tgctgggcag aaactgcaga ttcctgcaga gccccgacgg catggtgaag  300
cccaagagca ccagaaagta cgtggacagc aacaccatca acaccatgag aaaggccatc  360
gacagaaacg ccgaggtgca ggtggaggtg gtgaacttca agaagaacgg ccagagattc  420
gtgaacttcc tgaccatgat ccccgtgaga gacgagaccg gcgagtacag atacagcatg  480
ggcttccagt gcgagaccga gggaggaagc ggcggttccg gggggggatc cggaagtggt  540
tccggggggt gtacaaccgg cctgaactac cggatcatgc agagcgccat tgccgtgtac  600
gatagcggcg acgattacga ggccaagcag cagttcaagc tgatgttcga gaaggcccgg  660
ctgatcggca agggcacaac agagcctcat ccatttctgt acaaggtgtt cgcccgcagc  720
atccccgcca atgccgtcga gttctacgag cgctacctga tcgagcggaa gttctacctg  780
accggcctgt ccaacgagat caagaaaggc aacagagtgg atgtgccctt catccggcgg  840
gaccagaaca agtggaaaac acccgccatg aagaccctgg gcagaatcta cagcgaggat  900
ctgcccgtgg aactgcccag acagatgttc gacaatgaga tcaagtccca cctgaagtcc  960
ctgccacaga tggaaggcat cgacttcaac aatgccaacg tgacctatct gatcgccgag  1020
tacatgaaga gagtgctgga cgacgacttc cagaccttct accagtggaa ccgcaactac  1080
cggtacatgg acatgcttaa gggcgagtac gacagaaagg gctccctgca gcactgcttc  1140
accagcgtgg aagagagaga aggcctctgg aaagagcggg cctccagaac agagcggtac  1200
agaaagcagg ccagcaacaa gatccgcagc aaccggcaga tgagaaacgc cagcagcgaa  1260
gagatcgaga caatcctgga taagcggctg agcaacagcc ggaacgagta ccagaaaagc  1320
gagaaagtga tccggcgcta cagagtgcag gatgccctgc tgtttctgct ggccaaaaag  1380
accctgaccg aactggccga tttcgacggc gagaggttca aactgaaaga aatcatgccc  1440
gacgccgaga agggaatcct gagcgagatc atgcccatga gcttcacctt cgagaaaggc  1500
ggcaagaagt acaccatcac cagcgagggc atgaagctga agaactacgg cgacttcttt  1560
gtgctggcta gcgacaagag gatcggcaac ctgctggaac tcgtgggcag cgacatcgtg  1620
tccaaagagg atatcatgga agagttcaac aaatacgacc agtgcaggcc cgagatcagc  1680
tccatcgtgt tcaacctgga aaagtgggcc ttcgacacat accccgagct gtctgccaga  1740
gtggaccggg aagagaaggt ggacttcaag agcatcctga aatcctgct gaacaacaag  1800
aacatcaaca aagagcagag cgacatcctg cggaagatcc ggaacgcctt cgatcacaac  1860
aattaccccg acaaaggcgt ggtggaaatc aaggccctgc ctgagatcgc catgagcatc  1920
aagaaggcct ttggggagta cgccatcatg aagggatccc ttcaactgcc tccacttgaa  1980
agactgacac tgggtagttc ctacccatac gatgttccag attacgctta tccctacgac  2040
gtgcctgatt atgcataccc atatgatgtc cccgactatg cctaa                2085

SEQ ID NO: 70          moltype = DNA  length = 2736
FEATURE                Location/Qualifiers
misc_feature           1..2736
                       note = N725-GS16- pMag -GS16 polynucleotide sequence
source                 1..2736
                       mol_type = other DNA
                       organism = synthetic construct
SEQUENCE: 70
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccacatca ggttccacgt gaacatgggc  1080
```

```
aagctgagat acctgctgaa ggccgacaag acctgcatcg acggccagac cagagtcaga  1140
gtgatcgagc agcccctgaa cggcttcggc agactggaag aggccgagac aatgcggaag  1200
caagagaacg gcaccttcgg caacagcggc atccggatca gagacttcga gaacatgaag  1260
cgggacgacg ccaatcctgc caactatccc tacatcgtgg acacctacac acactacatc  1320
ctggaaaaca acaaggtcga gatgtttatc aacgacaaag aggacagcgc cccactgctg  1380
cccgtgatcg aggatgatag atacgtggtc aagacaatcc ccagctgccg gatgagcacc  1440
ctggaaattc cagccatggc cttccacatg tttctgttcg gcagcaagaa aaccgagaag  1500
ctgatcgtgg acgtgcacaa ccggtacaag agactgttcc aggccatgca gaaagaagaa  1560
gtgaccgccg agaatatcgc cagcttcgga atcgccgaga gcgacctgcc tcagaagatc  1620
ctggatctga tcagcggcaa tgcccacggc aaggatgtgg acgccttcat cagactgacc  1680
gtggacgaca tgctgaccga caccgagcgg agaatcaaga gattcaagga cgaccggaag  1740
tccattcgga gcgccgacaa caagatggga aagagaggct tcaagcagat ctccacaggc  1800
aagctggccg acttcctggc caaggacatc gtgctgtttc agcccagcgt gaacgatggc  1860
gagaacaaga tcaccggcct gaactaccgg atcatgcaga gcgccattgc cgtgtacgat  1920
agcggcgacg attacgaggc caagcagcag ttcaagctga tgttcgagaa ggcccggctg  1980
atcggcaagg gcacaacaga gcctcatcca tttctgtaca aggtgttcgc ccgcagcatc  2040
cccgccaatg ccgtcgagtt ctacgagcgc tacctgatcg agcggaagtt ctacctgacc  2100
ggcctgtcca acgagatcaa gaaaggcaac agagtggatg tgcccttcat ccggcgggac  2160
cagaacaagt ggaaaccccc gggatccgga ggaagtggca gctctggcgg cagtggaggg  2220
tctggtggca gcggacacac cctgtacgcc cccggcggct acgacatcat gggctacctg  2280
agacagatca gaaacagacc caacccccag gtggagctgg gccccgtgga caccagctgc  2340
gccctgatcc tgtgcgacct gaagcagaag gacaccccca tcgtgtacgc cagcgaggcc  2400
ttcctgtata tgaccggcta cagcaacgcc gaggtgctgg gcagaaactg cagattcctg  2460
cagagccccg acggcatggt gaagcccaag agcaccagaa agtacgtgga cagcaacacc  2520
atcaacacca tcagaaaggc catcgacaga aacgccgagg tgcaggtgga ggtggtgaac  2580
ttcaagaaga acggccagag attcgtgaac ttcctgacca tcatccccgt gagagacgag  2640
accggcgagt acagatacag catgggcttc cagtgcgaga ccgagggagg aagcggcggt  2700
tccggggggg gatccggaag tggttccggg gggtag                            2736
```

```
SEQ ID NO: 71           moltype = DNA  length = 1782
FEATURE                 Location/Qualifiers
misc_feature            1..1782
                        note = GS16- nMag -GS16-C726 polynucleotide sequence
source                  1..1782
                        mol_type = other DNA
                        organism = synthetic construct
SEQUENCE: 71
atgggaggaa gtggcagctc tggcggcagt ggagggtctg gtggcagcgg acacaccctg  60
tacgcccccg gcggctacga catcatgggc tacctggacc agatcggcaa cagacccaac  120
ccccaggtgg agctgggccc cgtggacacc agctgcgccc tgatcctgtg cgacctgaag  180
cagaaggaca cccccatcgt gtacgccagc gaggccttcc tgtatatgac cggctacagc  240
aacgccgagg tgctgggcag aaactgcaga ttcctgcaga gccccgacgg catggtgaag  300
cccaagagca ccagaaagta cgtggacagc aacaccatca acaccatgag aaaggccatc  360
gacagaaacg ccgaggtgca ggtggaggtg gtgaacttca agaagaacgg ccagagattc  420
gtgaacttcc tgaccatgat ccccgtgaga gacgagaccg gcgagtacag atacagcatg  480
ggcttccagt gcgagaccga gggaggaagc ggcggttccg gggggggatc cggaagtggt  540
tccgggggggt gtacaacacc cgccatgaag accctgggca gaatctacag cgaggatctg  600
cccgtggaac tgcccagaca gatgttcgac aatgagatca agtcccacct gaagtccctg  660
ccacagatgg aaggcatcga cttcaacaat gccaacgtga cctatctgat cgccgagtac  720
atgaagagag tgctggacga cgacttccag accttctacc agtggaaccg caactaccgg  780
tacatggaca tgcttaaggg cgagtacgac agaaagggct ccctgcagca ctgcttcacc  840
agcgtggaag agagagaagg cctctggaaa gagcgggcct ccagaacaga gcggtacaga  900
aagcaggcca gcaacaagat ccgcagcaac cggcagatga gaaacgccag cagcgaagag  960
atcgagacaa tcctggataa gcggctgagc aacagccgga acgagtacca gaaaagcgag  1020
aaagtgatcc ggcgctacag agtgcaggat gccctgctgt ttctgctggc caaaaagacc  1080
ctgaccgaac tggccgattt cgacggcgag aggttcaaac tgaaagaaat catgcccgac  1140
gccgagaagg gaatcctgag cgagatcatg cccatgagct tcaccttcga gaaaggcggc  1200
aagaagtaca ccatcaccag cgagggcatg aagctgaaga actacggcga cttctttgtg  1260
ctggctagcg acaaggaggat cggcaacctg ctggaactcg tgggcagcga catcgtgtcc  1320
aaagaggata tcatggaaga gttcaacaaa tacgaccagt gcaggcccga gatcagctcc  1380
atcgtgttca acctggaaaa gtgggccttc gacacatacc ccgagctgtc tgccagagtg  1440
gaccgggaag agaaggtgga cttcaagagc atcctgaaaa tcctgctgaa caacaagaac  1500
atcaacaaag agcagagcga catcctgcgg aagatccgga acgccttcga tcacaacaat  1560
taccccgaca aaggcgtggt ggaaatcaag gccctgcctg agatcgccat gagcatcaag  1620
aaggcctttg ggagtacgc catcatgaag ggatcccttc aactgcctcc acttgaaaga  1680
ctgacactgg gtagttccta cccatacgat gttccagatt acgcttatcc ctacgacgtg  1740
cctgattatg catacccata tgatgtcccc gactatgcct aa                    1782
```

```
SEQ ID NO: 72           moltype = DNA  length = 3345
FEATURE                 Location/Qualifiers
misc_feature            1..3345
                        note = N928-GS16- pMag -GS16 polynucleotide sequence
source                  1..3345
                        mol_type = other DNA
                        organism = synthetic construct
SEQUENCE: 72
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
```

```
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaaccact acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccacatca ggttccacgt gaacatgggc  1080
aagctgagat acctgctgaa ggccgacaag acctgcatcg acggccagac cagagtcaga  1140
gtgatcgagc agcccctgaa cggcttcggc agactggaag aggccgagac aatgcggaag  1200
caagagaacg gcaccttcgg caacagcggc atccggatca gagacttcga gaacatgaag  1260
cgggacgacg ccaatcctgc caactatccc tacatcgtgg acacctacac acactacatc  1320
ctggaaaaca acaaggtcga gatgtttatc aacgacaaag aggacagcgc cccactgctg  1380
cccgtgatcg aggatgatag atacgtggtc aagacaatcc ccagctgccg gatgagcacc  1440
ctggaaattc cagccatggc cttccacatg tttctgttcg gcagcaagaa aaccgagaag  1500
ctgatcgtgg acgtgcacaa ccggtacaag agactgttcc aggccatgca gaaagaagaa  1560
gtgaccgccg agaatatcgc cagcttcgga atcgccgaga gcgacctgcc tcagaagatc  1620
ctggatctga tcagcggcaa tgcccacggc aaggatgtgg acgccttcat cagactgacc  1680
gtggacgaca tgctgaccga caccgagcgg agaatcaaga gattcaagga cgaccggaag  1740
tccattcgga gcgccgacaa caagatggga aagagaggct tcaagcagat ctccacaggc  1800
aagctggccg acttcctggc caaggacatc gtgctgtttc agcccagcgt gaacgatggc  1860
gagaacaaga tcaccggcct gaactaccgg atcatgcaga gcgccattgc cgtgtacgat  1920
agcggcgacg attacgaggc caagcagcag ttcaagctga tgttcgagaa ggcccggctg  1980
atcggcaagg gcacaacaga gcctcatcca tttctgtaca aggtgttcgc ccgcagcatc  2040
cccgccaatg ccgtcgagtt ctacgagcgc tacctgatcg agcggaagtt ctacctgacc  2100
ggcctgtcca acgagatcaa gaaaggcaac agagtggatg tgcccttcat ccggcgggac  2160
cagaacaagt ggaaaacacc cgccatgaag accctgggca gaatctacag cgaggatctg  2220
cccgtggaac tgcccagaca gatgttcgac aatgagatca agtcccacct gaagtccctg  2280
ccacagatgg aaggcatcga cttcaacaat gccaacgtga cctatctgat cgccgagtac  2340
atgaagagag tgctggacga cgacttccag accttctacc agtggaaccg caactaccgg  2400
tacatggaca tgcttaaggg cgagtacgac agaaagggct ccctgcagca ctgcttcacc  2460
agcgtggaag agagagaagg cctctggaaa gagcgggcct ccagaacaga gcggtacaga  2520
aagcaggcca gcaacaagat ccgcagcaac cggcagatga gaaacgccag cagcgaagag  2580
atcgagacaa tcctggataa gcggctgagc aacagccgga acgagtacca gaaaagcgag  2640
aaagtgatcc ggcgctacag agtgcaggat gccctgctgt ttctgctggc caaaaagacc  2700
ctgaccgaac tggccgattt cgacggcgag aggttcaaac tgaaagaaat catgcccgac  2760
gccgagaagg gaatcctgag cgagttcccg ggatccggag gaagtggcag ctctggcggc  2820
agtggagggt ctggtggcag cggacacacc ctgtacgccc ccggcggcta cgacatcatg  2880
ggctacctga gacagatcag aaacagaccc aacccccagg tggagctggg ccccgtggac  2940
accagctgcg ccctgatcct gtgcgacctg aagcagaagg acaccccccat cgtgtacgcc  3000
agcgaggcct tcctgtatat gaccggctac agcaacgccg aggtgctggg cagaaactgc  3060
agattcctgc agagccccga cggcatggtg aagcccaaga gcaccagaaa gtacgtggac  3120
agcaacacca tcaacaccat cagaaaggcc atcgacagaa acgccgaggt gcaggtggag  3180
gtggtgaact tcaagaagaa cggccagaga ttcgtgaact tcctgaccat catccccgtg  3240
agagacgaga ccggcgagta cagatacagc atgggcttcc agtgcgagac cgagggagga  3300
agcggcggtt ccggggggggg atccggaagt ggttccgggg ggtag  3345
```

```
SEQ ID NO: 73           moltype = DNA  length = 1173
FEATURE                 Location/Qualifiers
misc_feature            1..1173
                        note = GS16- nMag -GS16-C929 polynucleotide sequence
source                  1..1173
                        mol_type = other DNA
                        organism = synthetic construct
SEQUENCE: 73
atgggaggaa gtggcagctc tggcggcagt ggagggtctg gtggcagcgg acacaccctg  60
tacgcccccg gcggctacga catcatgggc tacctggacc agatcggcaa cagacccaac  120
ccccaggtgg agctgggccc cgtggacacc agctgcgccc tgatcctgtg cgacctgaag  180
cagaaggaca cccccatcgt gtacgccagc gaggccttcc tgtatatgac cggctacagc  240
aacgccgagg tgctgggcag aaactgcaga ttcctgcaga gccccgacgg catggtgaag  300
cccaagagca ccagaaagta cgtggacagc aacaccatca acaccatgag aaaggccatc  360
gacagaaacg ccgaggtgca ggtggaggtg gtgaacttca agaagaacgg ccagagattc  420
gtgaacttcc tgaccatgat ccccgtgaga gacgagaccg gcgagtacag atacagcatg  480
ggcttccagt gcgagaccga gggaggaagc ggcggttccg gggggggatc cggaagtggt  540
tccggggggt gtacaatcat gcccatgagc ttcaccttcg agaaaggcgg caagaagtac  600
accatcacca gcgagggcat gaagctgaag aactacggcg acttctttgt gctggctagc  660
gacaagagga tcggcaacct gctggaactc gtgggcagcg acatcgtgtc caaagaggat  720
atcatggaag agttcaacaa atacgaccag tgcaggcccg agatcagctc catcgtgttc  780
aacctggaaa agtgggcctt cgacacatac cccgagctgt ctgccagagt ggaccgggaa  840
gagaaggtgg acttcaagag catcctgaaa atcctgctga acaacaagaa catcaacaaa  900
gagcagagcg acatcctgcg gaagatccgg aacgccttcg atcacaacaa ttaccccgac  960
aaaggcgtgg tggaaatcaa ggccctgcct gagatcgcca tgagcatcaa gaaggccttt  1020
```

```
ggggagtacg ccatcatgaa gggatccctt caactgcctc cacttgaaag actgacactg  1080
ggtagttcct acccatacga tgttccagat tacgcttatc cctacgacgt gcctgattat  1140
gcatacccat atgatgtccc cgactatgcc taa                               1173

SEQ ID NO: 74          moltype = AA  length = 150
FEATURE                Location/Qualifiers
REGION                 1..150
                       note = nMagHigh1 amino acid sequence
source                 1..150
                       mol_type = protein
                       organism = synthetic construct
SEQUENCE: 74
HTLYAPGGYD IMGYLDQIGN RPNPQVELGP VDTSCALILC DLKQKDTPIV YASEAFLYMT  60
GYSNAEVLGR NCRFLQSPDG MVKPKSTRKY VDSNTINTIR KAIDRNAEVQ VEVVNFKKNG  120
QRFVNFLTII PVRDETGEYR YSMGFQCETE                                   150

SEQ ID NO: 75          moltype = DNA  length = 450
FEATURE                Location/Qualifiers
misc_feature           1..450
                       note = nMagHigh1 polynucleotide sequence
source                 1..450
                       mol_type = other DNA
                       organism = synthetic construct
SEQUENCE: 75
cacaccctgt acgcccccgg cggctacgac atcatgggct acctggacca gatcggcaac  60
agacccaacc cccaggtgga gctgggcccc gtggacacca gctgcgccct gatcctgtgc  120
gacctgaagc agaaggacac ccccatcgtg tacgccagcg aggccttcct gtatatgacc  180
ggctacagca acgccgaggt gctgggcaga aactgcagat tcctgcagag ccccgacggc  240
atggtgaagc ccaagagcac cagaaagtac gtggacagca acaccatcaa caccatcaga  300
aaggccatcg acagaaacgc cgaggtgcag gtggaggtgg tgaacttcaa gaagaacggc  360
cagagattcg tgaacttcct gaccatcatc cccgtgagag acgagaccgg cgagtacaga  420
tacagcatgg gcttccagtg cgagaccgag                                   450
```

|---|---|---|---|

RNA EXPRESSION MODULATING OR EDITING METHOD VIA REGULATION OF CAS13 PROTEIN

RELATED APPLICATIONS

This application is a 35 U.S.C. 371 national stage filing from International Application No. PCT/KR2022/009993, filed Jul. 8, 2022, which claims priority to Korean Application No. 10-2022-0048556, filed Apr. 20, 2022, and Korean Application No. 10-2021-0089435, filed Jul. 8, 2021, the teachings of which are incorporated herein by reference.

BACKGROUND OF THE INVENTION

1. Field of the Invention

The present invention relates to a RNA expression modulating or editing method through chemical or optogenetic regulation of Cas13 protein activity.

2. Description of the Related Art

Clustered Regularly Interspaced Short Palindromic Repeats (CRISPR), in combination with associated sequences (cas), constitute CRISPR-Cas system, which confers adaptive immunity in many bacteria. The CRISPR-Cas system consists of short DNA repeats interposed by hypervariable sequences that provide adaptive immunity against invasive genetic elements such as phages and plasmids through sequence-specific targeting and interference. Typically, an invasive DNA sequence is acquired as a new "spacer", each paired with a CRISPR repeat and inserted as a new repeat-spacer unit at the CRISPR gene locus. The repeat-spacer array is then transcribed into long pre-CRISPR RNA (pre-crRNA), which is processed into small interfering CRISPR RNAs (crRNA) that induce sequence-specific recognition. In particular, crRNA induces nucleases for sequence-specific nucleic acid cleavage mediated by Cas endonucleases to complementary targets. The CRISPR-Cas system is identified in half of bacteria (~46%) and the majority of archaea (~90%).

The Cas system is currently being applied to many therapeutic fields by editing DNA sequence by substituting an appropriate guide molecule by targeting cellular DNA. In addition to Cas9 system capable of targeting DNA, several Cas proteins have been discovered, among which Cas13 protein targets single strand RNA.

The CRISPR-Cas13 system was discovered as a system that targets RNA differently from Cas9, and was first reported as C2c2 in 2016. The existing CRISPR-Cas13 system is mainly composed of four subtypes, which are characterized by having two HEPN domains (higher eukaryotes and prokaryotes nucleotide-binding domains) with RNase activity. Cas13, similar to Cas9, forms a complex with crRNA to cleave the target ssRNA, rendering the foreign gene inoperable.

The CRISPR-Cas13 system has been applied to various fields so far. There are literatures disclosing that Cas13a expression can be induced by inserting a promoter capable of binding to NF-κB, which is overexpressed in cancer (Molecular Therapy: Oncolytics Vol. 19 Dec. 2020), disclosing that the cleavage efficiency is different for each spacer of crRNA in glioma cells (Adv. Sci. 2019, 6, 1901299), applying the CRISPR-Cas13 system as a RNA virus therapeutic agent (Molecular Therapy: Nucleic Acids Vol. 19 Mar. 2020), and disclosing the K-RAS gene-specific spacer-specific cleavage of only the mutant K-Ras of cancer cells (Cancer Letters, Volume 431, 1 Sep. 2018, Pages 171-181). In the case of neurodegenerative diseases such as Parkinson's disease, the number of neurons is reduced. There have been reports in the literatures disclosing the possibility of treating neurological diseases with a glia-to-neuron transformation system through Cas13d transmission (Cell, Volume 181, Issue 3, 30 Apr. 2020, Pages 590-603.), and disclosing that the CRISPR-Cas system is effectively applied in zebrafish (Developmental Cell, Volume 54, Issue 6, 28 Sep. 2020, Pages 805-817.). However, in the case of the Cas13 system, there is a limitation in that expression cannot be controlled.

Optogenetics is a biological technology that can control cells in living tissues with light, and a typical example is the expression of ion channels that respond to light by genetically manipulating nerve cells. Optogenetics is a technology that combines optics and genetics, and by using it, it is possible to control and observe the activity of individual nerve cells in living tissues, even in freely moving animals, and to check in real time what effect the regulation of nerve activity causes. The main material required for optogenetics is a protein that responds to light. In order to control neural activity, optogenetic effectors such as channelrhodopsin, halorhodopsin and archaerhodopsin are used. To record neural activity optically, optogenetic sensors such as GCaMP detecting changes in calcium concentration, synaptopHluorin detecting secretion of neural endoplasmic reticulum, GluSnFRs detecting neurotransmitters, and Arclightning (ASAP1) detecting cell membrane potential are used. By using optogenetics, the neural activity of genetically classified specific neurons can be selectively controlled or recorded, and the target location and time can precisely controlled by using light. Therefore, the use of optogenetics has the potential to well regulate the CRISPR-Cas13 system in cells through intensity, temporal, and spatial control.

In addition, chemical genetics is a powerful method that uses small molecule regulators to inform the molecular basis of various biological processes, and refers to the control of proteins by perturbing cellular or physiological functions using low molecular weight compounds. As an example of regulating the function of a protein with a low molecular compound by chemical genetics, it is disclosed that a fusion protein comprising the heterodimer-forming proteins FRB and FKBP can form various oligomers according to addition of rapamycin (J BiosciBioeng. 2016 July; 122 (1): 40-6.).

Accordingly, the present inventors generated a fragment of Cas13 protein to enable recombination in order to regulate the activity of Cas13 in the CRISPR-Cas13 system, linked a chemogenetically or optogenetically bindable protein to each fragment, and the present inventors completed the present invention by confirming that the Cas13 protein could be activated by treatment of a low molecular weight compound or irradiation of light.

SUMMARY OF THE INVENTION

It is an object of the present invention to provide a RNA expression modulating or editing method through chemical or optogenetic regulation of Cas13 protein activity.

To achieve the above object, the present invention provides a method for regulating the activity of Cas13 protein, comprising a step of treating a first fragment containing the N-terminal segment of Cas13 protein and a first regulatory protein; and a second fragment containing a second regulatory protein and the C-terminal segment of Cas13 protein with a compound or light irradiation.

The present invention also provides a method for modulating the expression of a target RNA comprising the following steps:

1) preparing a vector comprising a construct containing a sequence encoding the N-terminal segment of Cas13 protein and a sequence encoding a first regulatory protein; and a vector comprising a construct containing a second fragment comprising a sequence encoding a second regulatory protein and a sequence encoding the C-terminal segment of Cas13 protein;
2) injecting the vector above and crRNA (CRISPR RNA) capable of hybridizing to the target RNA sequence into mammalian cells; and
3) treating with a compound or irradiating with light.

The present invention also provides a method for editing the target RNA sequence comprising the following steps:

1) preparing a vector comprising a construct containing a sequence encoding the N-terminal segment of Cas13 protein and a sequence encoding a first regulatory protein; and a vector comprising a construct containing a second fragment comprising a sequence encoding a second regulatory protein, a sequence encoding the C-terminal segment of Cas13 protein and a sequence encoding a RNA editing protein;
2) injecting the vector above and crRNA (CRISPR RNA) capable of hybridizing to the target RNA sequence into mammalian cells; and
3) treating with a compound or irradiating with light.

ADVANTAGEOUS EFFECT

The present invention relates to a RNA expression modulating or editing method through chemical or optogenetic regulation of Cas13 protein activity. Specifically, in order to regulate the activity of Cas13 in the CRISPR-Cas13 system, a fragment of the Cas13 protein was generated to enable recombination, and a chemogenetically or optogenetically bindable protein was linked to each fragment. And, it was confirmed that the Cas13 protein can be activated by treatment of a low molecular weight compound or irradiation of light. Accordingly, the method of the present invention can be effectively used for disease treatment by regulating RNA expression or editing RNA mutations related to disease.

BRIEF DESCRIPTION OF THE DRAWINGS

FIG. 3 is a schematic diagram showing the construct in which each regulatory protein is connected with a linker (GS16) so as not to affect Cas13b protein function using the FKBP (FK506-binding protein)-FRB (FKBP-rapamycin-binding) system, which is known to be dimerized by rapamycin.

DESCRIPTION OF THE PREFERRED EMBODIMENTS

Figure 1:
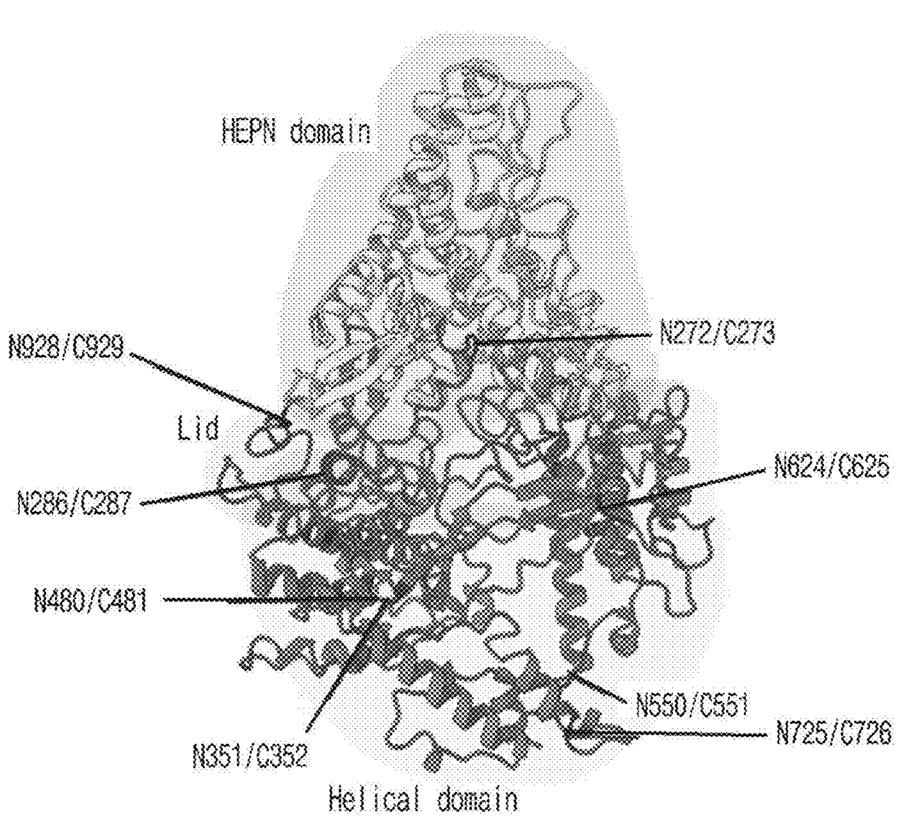
FIG. 1 is a schematic diagram showing the structure of the predicted PspCas13b protein, in which eight Cas13b fragment candidates are indicated.

Hereinafter, the present invention is described in detail.

The present invention provides a method for regulating the activity of Cas13 protein, comprising a step of treating a first fragment containing the N-terminal segment of Cas13 protein and a first regulatory protein; and a second fragment containing a second regulatory protein and the C-terminal segment of Cas13 protein with a compound or light irradiation.

The Cas13 protein is a kind of Cas protein. Cas protein is CRISPR-related protein, and is an enzyme that can recognize and cut nucleic acids such as DNA or RNA when they are double-stranded or single-stranded (dsDNA/RNA and ssDNA/RNA). Specifically, Cas protein can recognize and cut a double strand or single strand nucleic acid bound to crRNA or guide RNA. That is, the endonuclease function of Cas protein is activated by recognizing that crRNA is bound to the target site. In addition, Cas protein may have exonuclease activity capable of non-specific cleaving of double strand and/or single strand DNA and/or RNA as its endonuclease function is activated.

The Cas13 protein can be any one protein selected from the group consisting of Cas13a, Cas13b, Cas13c and Cas13d, and can naturally recognize and cut 'RNA', and is known as "C2c2" in bacteria. Cas13 is a class 2, type VI CRISPR protein, and is activated by recognizing an ssRNA target. Cas13a found in *Leptotrichiawadei* and Cas13b found in *Prevotella* sp. P5-125 are representative, both of which do not require a specific motif such as PAM.

The Cas13b protein is associated with one or more functional domains, and the effector protein contains one or more mutations in the HEPN domain so that the complex can transmit epigenetic modifiers or transcriptional or translational activation or repression signals. The complex can be formed in vitro or ex vivo, introduced into cells or contacted with RNA; or formed in vivo.

The Cas13b protein is not particularly limited, but in a specific embodiment of the present invention, the Cas13b protein is PspCas13b.

The PspCas13b protein is the most expressed in animal cells and has been proven to have an effective KD effect. The structure of the PspCas13b protein consists of two HEPN domains having RNase activity, crRNA and a domain that interacts with the target RNA.

A linker can be inserted between the N-terminal segment of Cas13 protein and the first regulatory protein, and between the second regulatory protein and the C-terminal segment of Cas13 protein.

The linker includes glycine (G) and serine (S), and can have an amino acid sequence in which glycine and serine are repeated 16 times (GSGSGSGSGSGSGSGSGSGSGSGSGSGSGSGS, SEQ. ID. NO: 21).

The N-terminal segment of Cas13 protein can be a segment from the N-terminus of Cas13 protein to the $272^{th}$ (SEQ. ID. NO: 1), $286^{th}$ (SEQ. ID. NO: 3), $351^{st}$ (SEQ. ID. NO: 5), $480^{th}$ (SEQ. ID. NO: 7), $550^{th}$ (SEQ. ID. NO: 9), $624^{th}$ (SEQ. ID. NO: 11), $725^{th}$ (SEQ. ID. NO: 13) or $928^{th}$ (SEQ. ID. NO: 15) amino acid, and the segment includes one HEPN domain having RNase activity.

The C-terminal segment of Cas13 protein can be a segment from the C-terminus of Cas13 protein to the $861^{th}$ (SEQ. ID. NO: 2), $847^{th}$ (SEQ. ID. NO: 4), $782^{th}$ (SEQ. ID. NO: 6), $653^{th}$ (SEQ. ID. NO: 8), $583^{th}$ (SEQ. ID. NO: 10), $509^{th}$ (SEQ. ID. NO: 12), $408^{th}$ (SEQ. ID. NO: 14) or $205^{th}$ (SEQ. ID. NO: 16) amino acid, and the segment includes one HEPN domain having RNase activity.

The compound treatment or light irradiation induces dimerization of the first regulatory protein and the second regulatory protein.

The compound treatment refers to chemogenetically control by disturbing the cellular or physiological function of a protein using a low molecular weight compound.

The compound is not particularly limited, but in a specific embodiment of the present invention, the compound is rapamycin.

The light irradiation refers to a biological technology capable of controlling cells of a living tissue with light.

The light is not particularly limited, but in a specific embodiment of the present invention, the light is blue light.

The combination of the first regulatory protein and the second regulatory protein is not particularly limited, but in a specific embodiment of the present invention, the combination of the first regulatory protein and the second regulatory protein is FKBP (SEQ. ID. NO: 18)—FRB (SEQ. ID. NO: 17), nMag (SEQ. ID. NO: 19)—pMag (SEQ. ID. NO: 20) or nMagH (SEQ. ID. NO: 74)—pMag (SEQ. ID. NO: 20).

Rapamycin, an antifungal antibiotic, mediates the tight heterodimer formation by simultaneously binding to the 12-kDa FK506 binding protein (FKBP) and FKBP rapamycin binding (FRB) domains ($K_d$=2.5 nM). Various cellular functions such as gene expression and protein translocation can be artificially controlled by conditional dimerization of a protein of interest fused to FKBP or FRB by adding rapamycin.

The said nMag-pMag was designed to recognize each other based on electrostatic interaction, preventing homodimerization and causing heterodimerization induced by light irradiation. The nMag-pMag system has the advantage that it has a small size similar to that of FKBP-FRB and can control the dissociation reaction rate. In nMagH (nMagHigh1), the $135^{th}$ methionine (M) and the $165^{th}$ methionine of nMag are mutated to isoleucine (I).

The present invention also provides a method for modulating the expression of a target RNA comprising the following steps:

1) preparing a vector comprising a construct containing a sequence encoding the N-terminal segment of Cas13 protein and a sequence encoding a first regulatory protein; and a vector comprising a construct containing a second fragment comprising a sequence encoding a second regulatory protein and a sequence encoding the C-terminal segment of Cas13 protein;
2) injecting the vector above and crRNA (CRISPR RNA) capable of hybridizing to the target RNA sequence into mammalian cells; and
3) treating with a compound or irradiating with light.

The mammalian cells can be isolated human cells or non-human mammalian cells.

The crRNA includes a guide sequence capable of hybridizing to the target RNA sequence and a direct repeat sequence.

The crRNA is CRISPR RNA, and can be single strand RNA. In addition, the crRNA can bind to tracrRNA to actuate CRISPR-associated protein, and the crRNA can be used in combination with tracrRNA. At this time, the CRNA can have a sequence complementary to a gene sequence specifically present in the target.

The crRNA can be RNA composed of 15 to 40 nucleic acids. At this time, the polynucleotide can be composed of 18 to 30 or 20 to 25 nucleic acids. In one embodiment, the crRNA may consist of 20 nucleic acids. In addition, the crRNA can include an additional sequence at 3' to make the CRISPR-associated protein active.

The crRNA comprises a spacer sequence and a direct repeat (DR) sequence or a derivative thereof. In a preferred embodiment of the present invention, the spacer sequence or a derivative thereof comprises a seed sequence, and the seed sequence is important for recognition and/or hybridization to a sequence at the target locus. In a preferred embodiment of the present invention, the crRNA is a short crRNA capable of being associated with a short DR sequence.

The crRNA comprises a bulge, hairpin or stem loop structure. The loop is preferably GAAA, but is not limited to this sequence, and in fact is not limited to only 4 bp in length. Indeed, the preferred loop-forming sequence used in the hairpin structure is 4 nucleotides in length and most preferably has the sequence of GAAA. However, longer or shorter loop sequences can be used, and surrogate sequences can also be used. The sequence preferably comprises a nucleotide triple (for example, AAA), and an additional nucleotide (for example, C or G). Examples of loop forming sequences include CAAA and AAAG.

The crRNA may be chemically modified. Examples of chemical modifications include the inclusion of 2'-O-methyl (M), 2'-O-methyl 3'-phosphorothioate (MS) or 2'-O-methyl 3'-thio PACE (MSP) at one or more terminal nucleotides, but not always limited thereto. Such chemically modified crRNA may have increased stability and increased activity compared to unmodified crRNA, although the on-target versus off-target specificity is not predictable.

The chemically modified crRNA includes, without limitation, RNA having locked nucleic acid (LNA) nucleotides comprising a phosphorothioate linkage and a methylene bridge between the 2' and 4' carbons of a ribose ring.

A vector can be used for synthesizing a polynucleotide encoding Cas13b protein and crRNA used in the method of the present invention, or for modulating the expression of a target RNA or editing the target RNA. As used herein, a "vector" is a tool that allows or facilitates the transfer of an entity from one environment to another environment. A replicon such as plasmid, phage or cosmid, or another DNA segment can be inserted into the vector, causing replication of the inserted segment. In general, a vector is capable of replication when associated with appropriate control element.

In general, the term "vector" refers to a nucleic acid molecule capable of delivering another nucleic acid to which it has been linked. A vectors includes, without limitation, nucleic acid molecules that are single-stranded, double-stranded or partially double-stranded; nucleic acid molecules containing one or more free ends, or not containing free ends (for example: circular); nucleic acid molecules containing DNA, RNA or both; and other types of polynucleotides known in the art. One type of vector is a "plasmid", which refers to a circular double-stranded DNA loop into which additional DNA fragments can be inserted, for example, by standard molecular cloning techniques. Another type of vector is a viral vector, in which a virus-derived DNA or RNA sequence is present in a vector that is encapsulated in a virus (for example, retrovirus, replication deficient retrovirus, adenovirus, replication deficient adenovirus and adeno-associated virus (AAV)). A viral vector also includes a polynucleotide carried by a virus for transfection into host cells. Certain vectors (for example, bacterial vectors and episomal mammalian vectors having a bacterial origin of replication) are capable of autonomous replication in the host cell into which they are introduced. Other vectors (for example, non-episomal mammalian vectors) integrate into the genome of the host cell upon introduction into the host cell, thereby being replicated along with the host genome. Moreover, certain vectors are capable of directing the expression of genes to which they are operably linked. Such vectors are referred to herein as "expression vectors". Conventional expression vectors useful in recombinant DNA technology often exist in the form of plasmids. A recombinant expression vector can contain the nucleic acid of the present invention in a form suitable for expression of the nucleic acid in a host cell, which means that the recombinant expression vector contains one or more regulatory elements. The one or more regulatory elements can be selected based on the host cell to be used for the expression and is operably linked to the nucleic acid sequence to be expressed. In the recombinant expression vector, "operably linked" means that the target nucleotide sequence (for example, in an in vitro transcription/translation system, or in a host cell if the vector is introduced into the host cell) is linked to the regulatory elements in a manner that enables expression of the nucleotide sequence.

The vector can be any one selected from the group consisting of plasmids and viruses.

Specific examples of the plasmid DNA include commercial plasmids such as pCMV3, pET28a, pUC57 and pET. Other examples of the plasmid that can be used in the present invention include *E. coli*-derived plasmids (pUC57, pCMV3, pET28a, pET, pGEX, pQE, pDEST and pCOLD), *Bacillus subtilis*-derived plasmids (pUB110 and pTP5) and yeast-derived plasmids (YEp13, YEp24 and YCp50). Since these plasmids show different protein expression levels and modifications depending on the host cell, a host cell most suitable for the purpose can be selected and used.

Specific examples of the virus include adeno-associated virus (AAV), adenovirus, retrovirus, lentivirus, modified vaccinia virus ankara (MVA), herpes simplex virus or baculovirus.

In conducting any of the methods disclosed herein, a suitable vector can be introduced into a cell or embryo via one or more methods known in the art, including microinjection, electroporation, sonoporation, biolistics, calcium phosphate-mediated transfection, cation transfection, liposome transfection, dendrimer transfection, heat shock transfection, nucleofection transfection Induction, magnetofection, lipofection, imperfection, optical transfection, dedicated agent-enhanced uptake of nucleic acids, and delivery via liposomes, immunoliposomes, virosomes or artificial virions.

In some methods, a vector is introduced into a cell by microinjection. A vector or vectors can be microinjected into the nucleus or cytoplasm. In some methods, a vector or vectors can be introduced into a cell by nucleofection.

A vector can be designed for expression of CRISPR transcript (for example, nucleic acid transcript, protein or enzyme) in prokaryotic or eukaryotic cells. For example, the CRISPR transcript can be expressed in bacterial cells such as Escherichia coli, insect cells (using a baculovirus expression vector), yeast cells, or mammalian cells.

A recombinant expression vector can be transcribed and translated in vitro using, for example, a T7 promoter regulatory sequence and T7 polymerase.

The Cas13 protein forms a complex with the crRNA. The complex can be in the form of a ribonucleoprotein (RNP), and can be passed through a cell membrane in the form of RNP and delivered into a cell or a living body. In addition, the complex can be delivered into a cell or a living body by being included in a conventional RNA carrier.

The present invention also provides a method for editing the target RNA sequence comprising the following steps:

1) preparing a vector comprising a construct containing a sequence encoding the N-terminal segment of Cas13 protein and a sequence encoding a first regulatory protein; and a vector comprising a construct containing a second fragment comprising a sequence encoding a second regulatory protein, a sequence encoding the C-terminal segment of Cas13 protein and a sequence encoding a RNA editing protein;
2) injecting the vector above and crRNA (CRISPR RNA) capable of hybridizing to the target RNA sequence into mammalian cells; and
3) treating with a compound or irradiating with light.

The Cas13 protein can be deadCas13 protein from which RNase activity is removed.

The deadCas13 protein is inactivated by mutating two histidines of HEPN to alanines to prevent the HEPN domain having RNase activity from functioning.

The RNA editing protein can be ADAR1 (Adenosine deaminase Acting on RNA) or ADAR2 (Adenosine deaminase Acting on RNA), but not always limited thereto. In a specific embodiment of the present invention, the ADAR protein is ADAR2, and the deaminase domain (ADAR2 276-702) involved in A-to-I RNA editing and the deaminase domain of ADAR2 mutated to enable C-to-U RNA editing (V16S/E488Q/V351G/S486A/T375A/S370C/P462A/N597I/L332I/I398V/K350I/M383L/D619G/S582T/V440I/S495N/K418E/S661T) were used.

Figure 2:
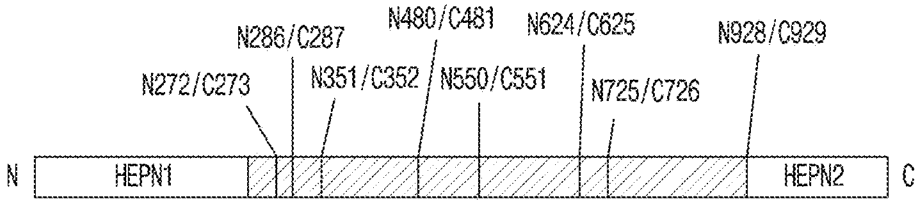
FIG. 2 is a schematic diagram showing the cleavage sites of a Cas13b fragment candidate that is expected to exhibit Cas13b activity by conserving two HEPN domains having RNase activity.

In a specific embodiment of the present invention, a fragment of Cas13b was designed, which is expected to exhibit Cas13b activity because two HEPN domains with RNase activity can be conserved and recombined (FIGS. 1 and 2). A flexible controllable construct was designed by connecting each regulatory protein with a linker (GS16) not to affect Cas13b protein function using the FKBP (FK506-binding protein)-FRB (FKBP-rapamycin-binding) system known to be dimerized by rapamycin (see FIG. 3). The other flexible controllable construct was designed by connecting each regulatory protein with a linker (GS16) not to affect Cas13b protein function using the nMag-pMag system known to be dimerized by blue light (see FIG. 4). By confirming that the luciferase activity was decreased by rapamycin treatment, it was confirmed that the activity of Cas13b protein can be regulated by rapamycin (see FIG. 5), and a chemo-inducible RNA regulation module was developed using this (see FIG. 6). In addition, it was that confirmed Cas13b can be activated by irradiating blue light and that the expression of the target RNA can be reduced by the crRNA that can be hybridized with the Cas13b activated by blue light and the target RNA (FIGS. 8 to 11). As a result of removing the RNase activity and linking ADAR2, an RNA editing regulatory protein, to the C-terminus of Cas13b, it was confirmed that the A-to-I RNA mutation can be edited by blue light in the Firefly reporter, which does not produce a normal protein by the mutation (FIGS. 12 to 20). By designing a fluorescent protein-based indicator, it was also confirmed that C-to-U base editing was possible by blue light (FIGS. 21 to 24). 또한, In addition, it was confirmed that the light-induced padCas13 editor can edit endogenous transcripts (FIGS. 25 and 26).

Therefore, the method of the present invention can be effectively used in the treatment of a disease by modulating RNA expression or editing RNA mutation associated with the disease.

Hereinafter, the present invention will be described in detail by the following examples and experimental examples.

However, the following examples and experimental examples are only for illustrating the present invention, and the contents of the present invention are not limited thereto.

Example 1: Prediction of Cas13b Protein Fragment Candidate Capable of Rebinding Through Reconstruction of PspCas13b Protein In order to control the activity of Cas13b while targeting the endogenous RNA of animal cells, the PspCas13b (*Prevotella* sp. P5-125 Cas13b) system known to be strongly expressed in animal cells was used. However, since the structure of PspCas13b was not identified, the structure of PspCas13b was reconstructed by UCSF Chimera tool using the structure of PbuCas13b, which has already been identified (see FIG. 1). By conserving and recombination of two HEPN domains having RNase activity, a fragment of Cas13b expected to exhibit Cas13b activity was designed.

Figure 8:
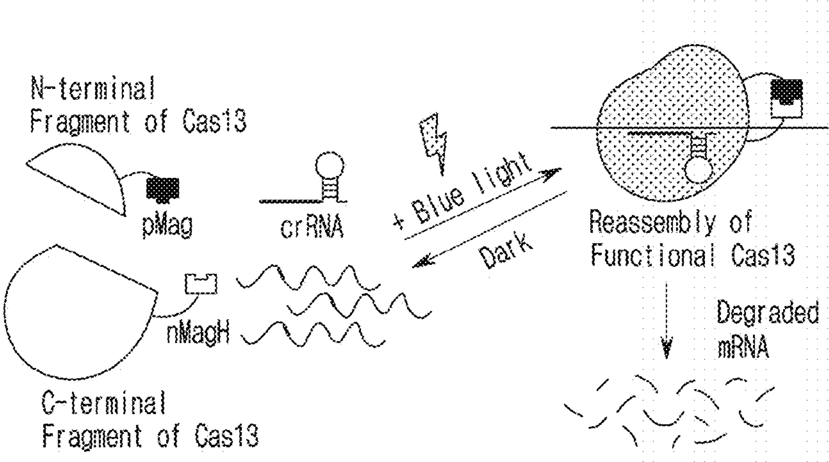
FIG. 8 is a schematic diagram showing the crRNA-mediated RNA degradation activity of Cas13 (paCas13) to allow the Cas13 fragment cleaved by blue light treatment inducing heterodimerization between pMag and nMag to recombine.

As a result, as shown in FIGS. 1 and 2, 8 fragment candidates of PspCas13b protein were predicted.

Example 2: Construct Design that can Chemically Modulate PspCas13b Protein Activity A construct was designed to chemically control the activity of PspCas13b protein based on the recombination-capable fragment of Cas13b protein predicted in Example 1 above.

Figure 3:
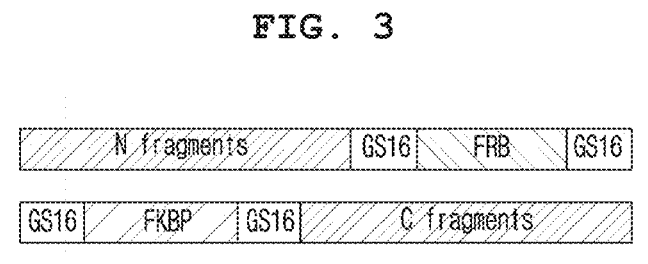

Specifically, as shown in FIG. 3, a construct was designed using the FKBP (FK506-binding protein)-FRB FRB (FKBP-rapamycin-binding) system known to be dimerized by rapamycin. The cDNA encoding the Cas13b fragment of Example 1 fused with the nuclear export signal of HIV was amplified in pC0046-EF1a-PspCas13b-NES-HIV (Addgene plasmid 103862). Each regulatory protein was connected with a linker (GS16) so as not to affect the Cas13b protein function to enable flexible modulation. The DNA sequence encoding the FKBP-FRB domain was synthesized by Twist Bioscience. All Cas13 fragments were synthesized using Gibson assembly. PCR fragments for Gibson Assembly were amplified using Phusion Hot-Start II DNA Polymerase (Thermofisher). A chemoinducible Cas13 construct based on the GFKBP-FRB domain and the Cas13 fragment (N-terminus and C-terminus) was cloned into the XhoI/XmaI and BsrGI/NotI sites of the EGFP-N1 plasmid (Clonetech), respectively.

Example 3: Construct Design That can Optogenetically Modulate PspCas13b Protein Activity A construct was designed to optogenetically control the activity of PspCas13b protein based on the recombination-capable fragment of Cas13b protein predicted in Example 1 above.

Figure 4:
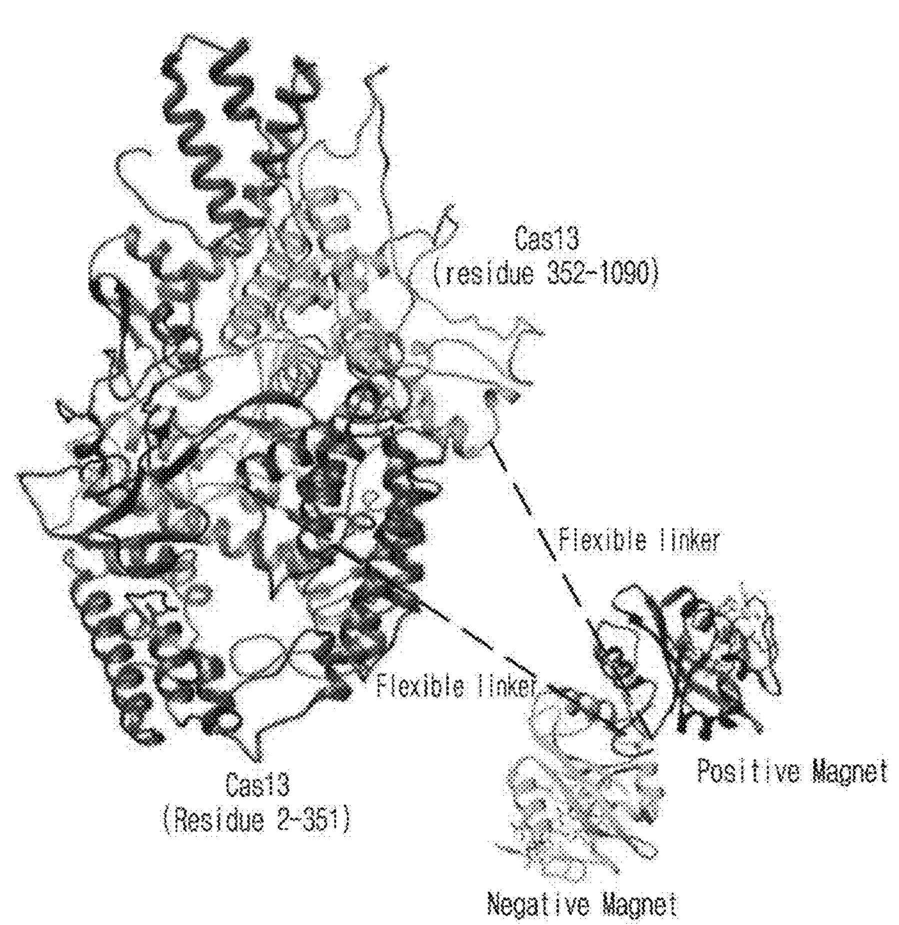
FIG. 4 is a schematic diagram showing the construct in which each regulatory protein is connected with a linker (GS16) using the nMag (negative Mag)-pMag (positive Mag) system, which is known to be dimerized by blue light.

Specifically, as shown in FIG. 4, a construct was designed using the nMag-pMag system known to be dimerized by blue light. Since FKBP and FRB are 107 amino acids and 93 amino acids in length, a magnet system (150 amino acids) of similar size was used to avoid steric hindrance. Two combinations of pMag: nMag and pMag:nMagH (nMag with M135I and M165I mutations) were used. To construct padCas13, the inactivated HEPN RNase domain (including H133A and H1058A mutations) was amplified in pC0049-EF1a-dPspCas13b-NES-HIV (Addgene 103865). Each regulatory protein was connected with a linker (GS16) so as not to affect the Cas13b protein function to enable flexible modulation. The DNA sequences encoding the pMag:nMag and pMag:nMagH domains were synthesized by Twist Bioscience. All Cas13 fragments were synthesized using Gibson assembly. PCR fragments for Gibson Assembly were amplified using Phusion Hot-Start II DNA Polymerase (Thermofisher). A photoinducible Cas13 construct based on the pMag:nMag or pMag:nMagH domain and the Cas13 fragment (N-terminus and C-terminus) was cloned into the XhoI/XmaI and BsrGI/NotI sites of the EGFP-N1 plasmid (Clonetech), respectively.

Example 4: Construction of crRNA

CrRNAs targeting the Fluc reporter, GFP indicator, KRAS, PPIB, STAT3 and A-to-I or C-to-U RNA editing site were generated by annealed oligo cloning using the pC0043-PspCas13b crRNA backbone (Bbsl region of Addgene plasmid 103854). All crRNA plasmids were cloned using T4 DNA ligase (Elpis Biotech). A multiplexed crRNA was constructed using Gibson assembly of three fragment ligation.

Experimental Example 1: Confirming Whether Cas13b Protein is Activated by Rapamycin Luciferase reporter assay was performed to confirm whether the Cas13b protein was activated by rapamycin when the construct designed in Example 2 was used.

Specifically, to evaluate the changes in protein levels, HEK293T cells (ATCC) were co-transfected with 10 ng of a double luciferase reporter plasmid (Promega), 75 ng of each inducible Cas13 fragment expressing the plasmid, and 100 ng of a crRNA expression plasmid. 16 hours prior to transfection, the cells were placed in a 96-well plate (Corning) and allowed to grow until reaching 80% confluency. On the next day, 10 μL of Opti-MEM and 10 μL of Opti-MEM containing 0.6 μL of lipofectamine LTX and 0.26 μL of PLUS reagent and all transfected DNA plasmids were mixed, and a total of 20 μL of Opti-MEM I reducing serum medium (ThermoFisher) was added to each well. All solutions were incubated for 5 minutes before slowly added to the cells. For 24 hours prior to analysis, 500 nM of rapamycin was treated and 48 hours later, luciferase readouts of Firefly luciferase (experimental group) and Renilla luciferase (control group) were sequentially measured with a Tecan plate reader using the Dual-Glo Luciferase Assay System (Promega) according to the manufacturer's instructions. The experiment was performed in triplicate. The decrease in the target RNA, the Firefly transcript, was confirmed by comparing the expression value at the protein level of the control group Renilla.

Figure 5:
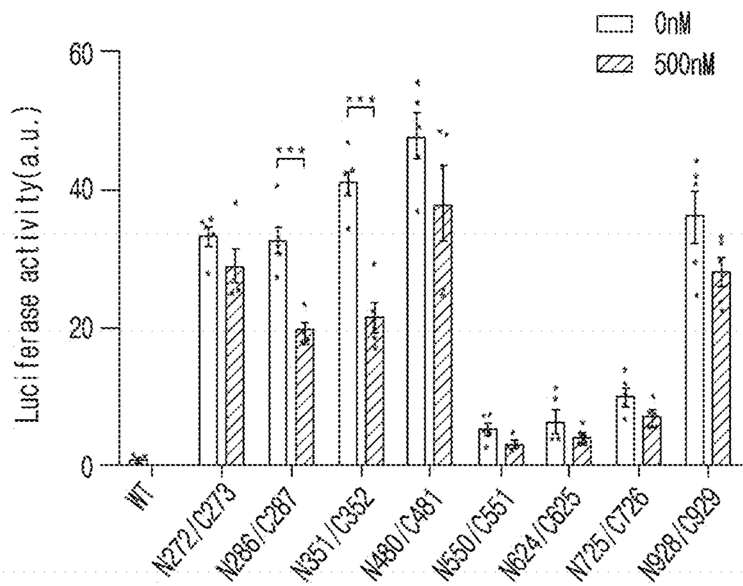
FIG. 5 is a graph showing the Cas13 activity measured by double luciferase analysis after treatment with 500 nM rapamycin (error bar, mean±sem, n=5, student's two-tailed t-test).
Figure 6:
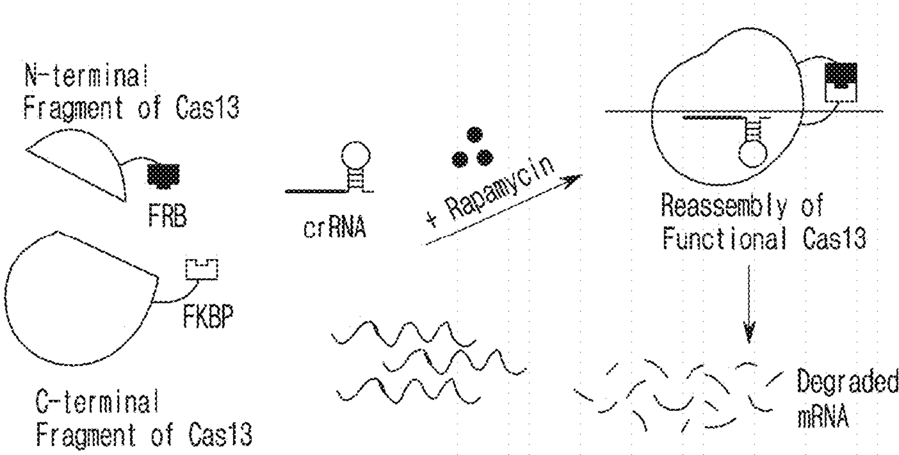
FIG. 6 is a schematic diagram showing the crRNA-mediated RNA degradation activity of Cas13 to allow the Cas13 fragment cleaved by rapamycin treatment inducing heterodimerization between FRB and FKBP to recombine.

As a result, as shown in FIG. 5, it was confirmed that N550/C551, N624/C625 and N725/C726 among the fragments of Cas13b protein could be reunited in cells without rapamycin stimulation. In addition, it was confirmed that the luciferase expression was moderately reduced in the absence of rapamycin, and the background activity was not due to the residual nuclease activity of the individually cleaved Cas13 fragment. Based on these results, a chemo-inducible RNA regulation module capable of recombination of Cas13 fragments by rapamycin treatment was developed (FIG. 6). In subsequent experiments, in particular, N351/C352 fragments, which were significantly different before and after induction with rapamycin, were used.

Figure 7:
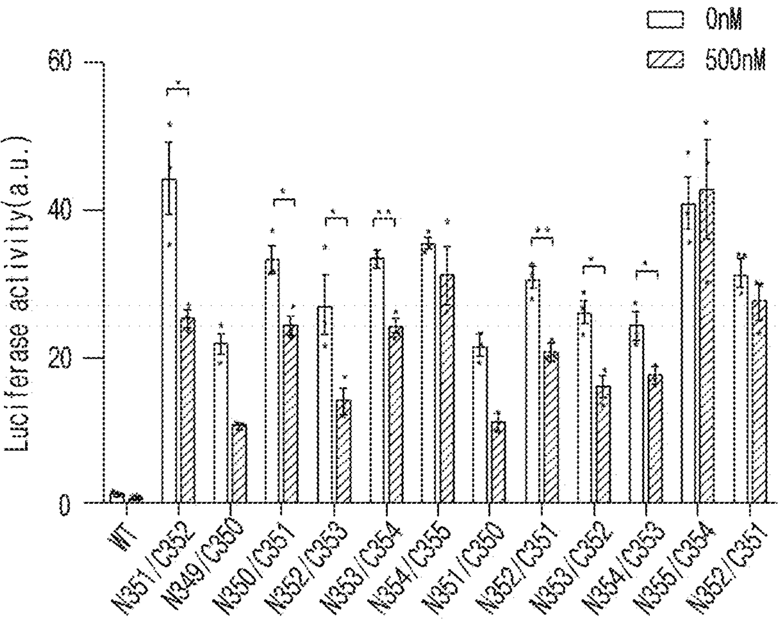
FIG. 7 is a graph showing the results of the second screening of the Cas13 cleavage site near the residues 351 and 352 (error bar, mean±sem, n=3, student's two-tailed t-test).

A second screening of Cas13 fragment sites was performed near the residues 351 and 352 to select more efficient fragments, and N351/C352, N351/C350 and N353/C352 of paCas13 were named paCas13-1, paCas13-2 and paCas13-, respectively (FIG. 7).

Experimental Example 2: Confirming Whether Cas13b Protein is Activated by Blue Light <2-1> Characterization of Photoactivatable Cas13 (paCas 13)

Luciferase reporter assay was performed to confirm whether the Cas13b protein was activated by light stimulation when the construct designed in Example 3 was used.

To test the light-inducible RNA targeting of paCas13, the target RNA knockdown activity of paCas13 fragments was evaluated using a dual luciferase system under the blue light stimulation for 24 hours with an LED plate emitting 488 nm of blue light (FIG. 8). The luciferase reporter assay was performed as described in Example 4.

Figure 9A:
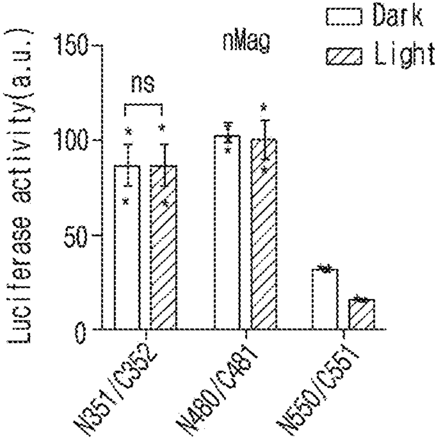
FIG. 9 is a set of graphs showing the decrease in luciferase activity upon light stimulation using the paCas13 fragment fused with photoinducible dimerization domains (pMag: nMag and pMag:nMagHigh1).
Figure 9B:
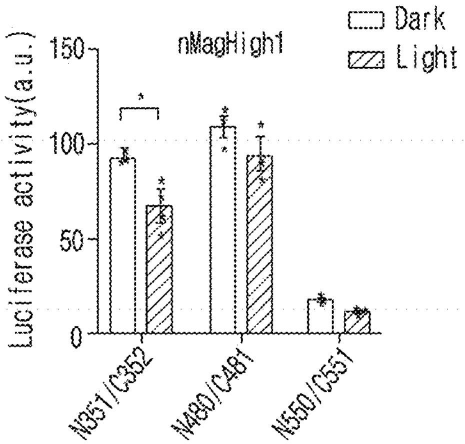
Figure 10:
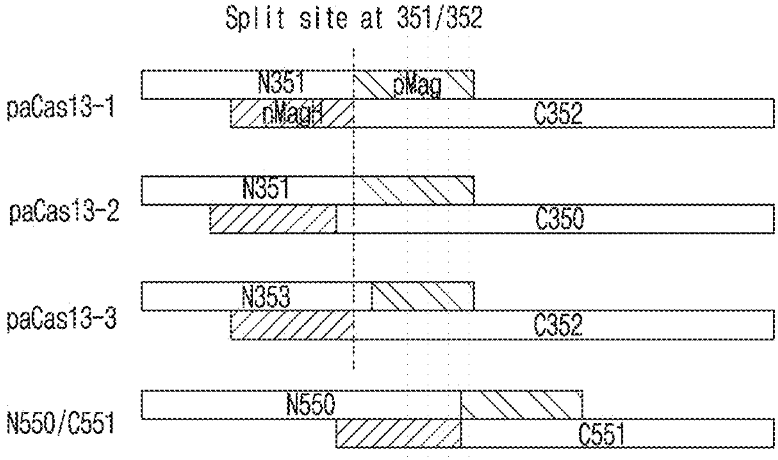
FIG. 10 is a schematic diagram showing the paCas13 candidates based on Cas13 cleavage sites near the residues 351 and 352.
Figure 11A:
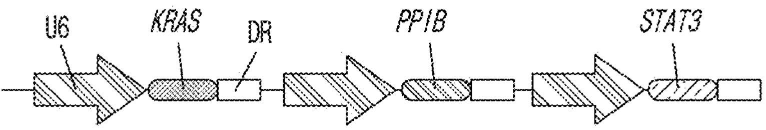
FIG. 11 is a set of graphs showing the light-induced RNA knockdown of endogenous KRAS, PPIB and STAT3 in HEK293T cells transfected with paCas13-1, paCas13-2 or paCas13-3 and multiple crRNAs (error bar, mean±sem, n=3).
Figure 11B:
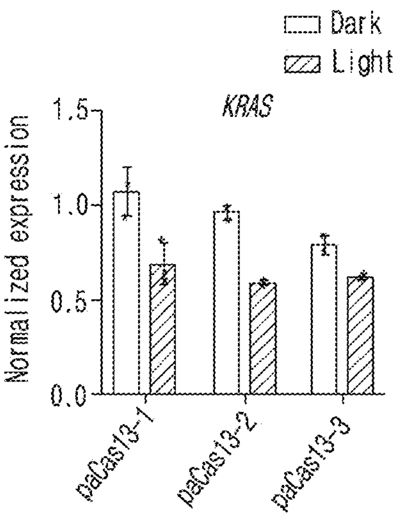
Figure 11C:
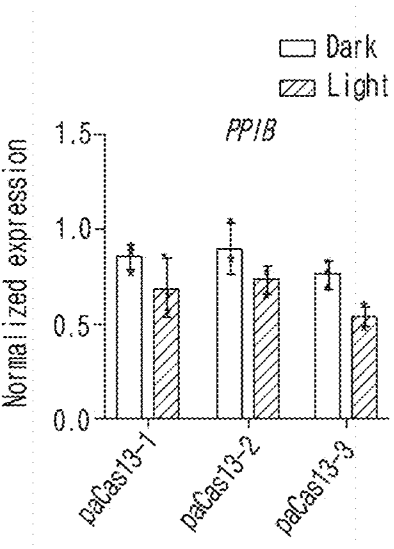
Figure 11D:
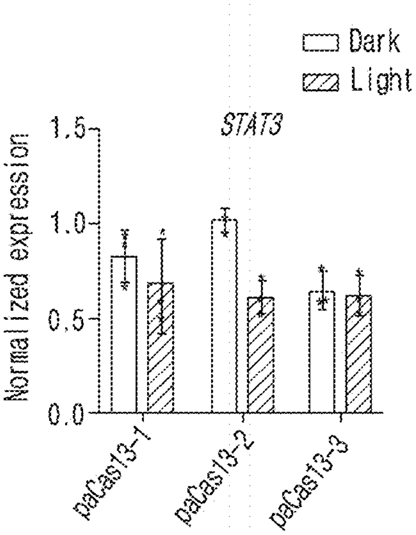

As a result, as shown in FIG. 9, each paCas13 construct showed significant luciferase knockdown upon blue light induction, identical to the rapamycin-inducible construct. Efficient target mRNA cleavage was seen in pMag in combination with nMagH (nMagHigh1) but not nMag. Therefore, in all the subsequent experiments, a system using pMag:nMagH was used.

In addition, a light-inducible candidate was selected based on the screening results of Example 4 (FIG. 10), and the experiments to confirm the function of paCas13 on RNA interference by targeting endogenous transcripts, KRAS, PPIB and STAT3 previously targeted by the Cas13 system were performed.

Particularly, to create a system that can achieve efficient and easy multiplex RNA modulation, a single crRNA expression vector with multiple crRNAs was used.

As a result, as shown in FIG. 11, significant knockdown of the target transcript by paCas13 under the light stimulation was observed.

These results indicate that the paCas13 system can perturb endogenous transcripts through light stimulation.

<2-2> Optogenetic RNA Regulation by paCas13

Figure 12:
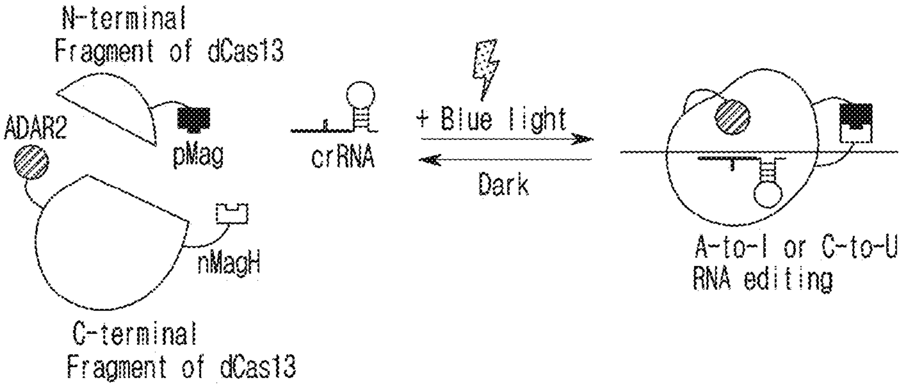
FIG. 12 is a schematic diagram showing the modulated RNA regulation by coupling padCas13 (including H133A and H1058A mutations that inactivate the HEPN RNase domain of Cas13b) with ADAR2DD.

To further demonstrate the utility of paCas13, a regulatory domain was fused to the padCas13 fragment to construct a photoactivation and reversible RNA editing system (hereinafter referred to as padCas13) (FIG. 12).

Programmable RNA editing systems using catalytically inactive Cas13 (dCas13) to deliver the catalytic domain of ADAR2 (adenosine deaminase acting on RNA type2) to specific transcripts of mammalian cells are known from many studies. ADAR2 hydrolytically deaminates adenosine in double strand RNA to make inosine, and inosine pairs with cytosine and exhibits similar properties to guanosine. In the present invention, the padCas13 system was constructed using the ADAR2 system.

<2-2-1> Light-Inducible A-to-I RNA Editing by paCas13

To confirm the light-inducible RNA editing of the present invention, A-to-I (adenine to inosine) editing was performed, and then luciferase reporter assay was performed.

Figure 13:
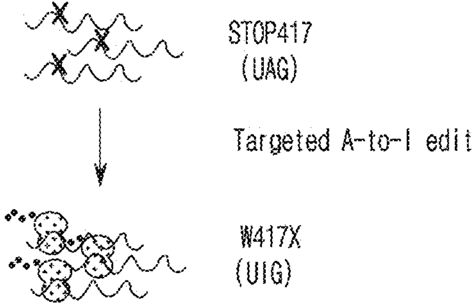
FIG. 13 is a schematic diagram showing the A-to-I RNA editing reporter assay, in which a single G-to-A mutation is introduced into the firefly luciferase coding sequence, resulting in W417X (X=STOP) codon switch, a measurable firefly luciferase signal is lost.

Specifically, the catalytic deaminase domain of ADAR2 for A-to-I editing (ADAR2DD) was amplified in pC0050-CMV-dPspCas13b-longlinker-ADAR2DD (wt) (Addgene plasmid 103866). A padCas13 editor was designed by fusing ADAR2DD to the C terminus of the Cas13 fragment. To verify the activity of the padCas13 editor, an RNA editing reporter for Fluc gene was designed by introducing a nonsense mutation [W417X (UGG→UAG)]. This mutation can be modified to a wild-type codon via A-to-I editing, which can be detected by restoration of the firefly luciferase signal (FIG. 13). The luciferase reporter assay was performed as described in Example 4.

Figure 14A:
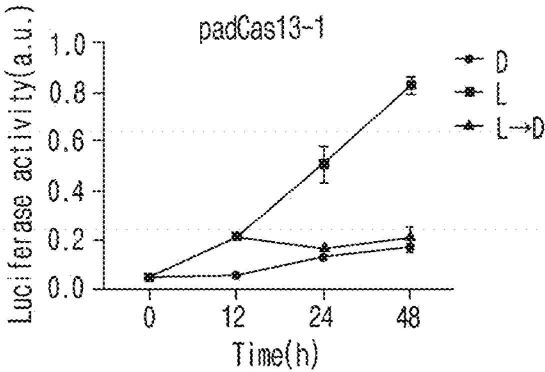
FIG. 14 is a set of graphs showing the analysis results over time of the padCas13 editor under the light conditions quantified by the restoration of the firefly luciferase signal (D: dark, L: light).
Figure 14B:
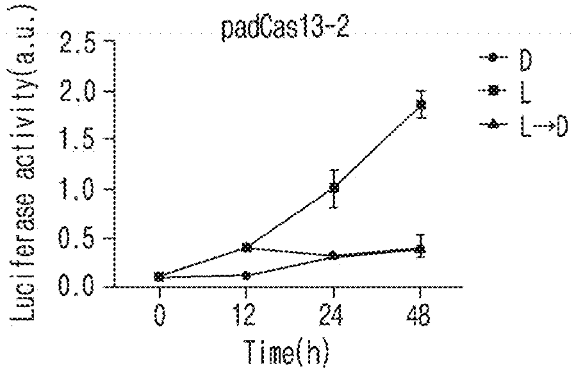

The efficiency of A-to-I editing by light stimulation over time was observed. As a result, as shown in FIG. 14, when blue light was turned on, as the duration of light stimulation was increased, the luciferase activity by restoration was increased. When the light was turned off after stimulation for 6 hours, it was confirmed that the increased luciferase activity by restoration returned to the baseline within 24 hours.

To further verify the restoration of the luciferase activity, reverse transcription (RT)-polymerase chain reaction (PCR) was performed, followed by Sanger sequencing.

Specifically, to evaluate the changes in RNA levels after transfection of the paCas13 system, total RNA was isolated from HEK293T cells and RT-qPCR was used to quantify the changes in RNA levels. Total RNA isolation was performed using PureLink RNA mini kit (Invitrogen). After the RNA isolation, RNA was reverse transcribed into cDNA using gDNA eraser (Takara) and PrimeScript RT Reagent Kit. All qPCR reactions were performed in a volume of 20 μL using SYBR green master mix (Toyobo) and amplified in CFX-maestro 96 (Bio-rad). A qPCR primer was designed to span the crRNA target site. The expression levels were calculated using the cycle threshold (Ct) values of GAPDH and the Ct values of the gene of interest. The relative expression level of one gene was determined as $2^{\Delta Ct}$ (ΔCt=Ct (gene of interest)−Ct (GAPDH)). The relative expression level of the target gene was obtained by normalizing the expression level of the target gene in cells treated with on-target crRNA to the expression level of the target gene in cells treated with non-targeting (NT) crRNA.

Sanger sequencing was performed by PCR amplification of the cDNA product with Phusion DNA polymerase (Thermofisher) using target-specific primers, and then by Cosmogintech. Editing efficiency was calculated by analyzing the height of each Sanger peak at the target site using Indigo software (https://www.gear-genomics.com/indigo/). The Sanger sequencing standard curve was generated from the sequencing results of several DNA samples deliberately mixed. A standard curve was used to correct for editing efficiencies that could be altered by PCR bias and sequencing bias.

Figure 15:
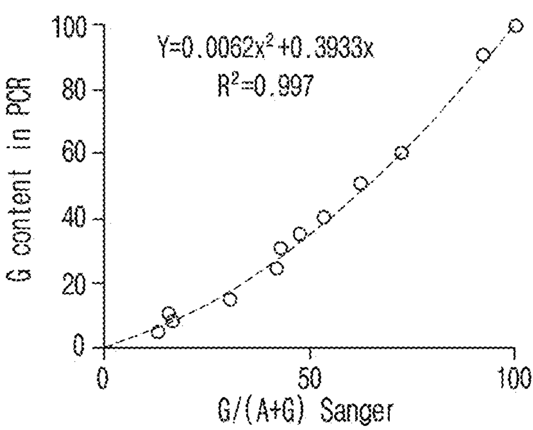
FIG. 15 is a graph showing the standard curve for correcting Sanger sequencing chromatogram with fluorophore and PCR bias.
Figure 16:
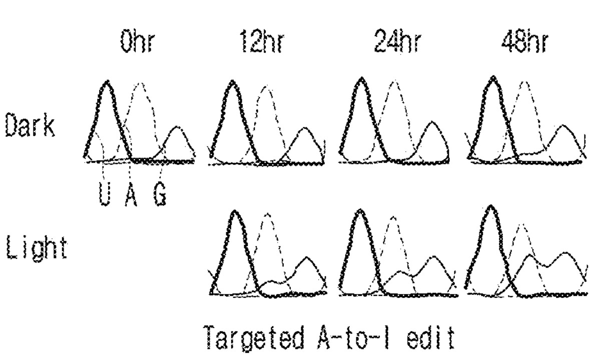
FIG. 16 is a diagram showing the sequencing chromatogram under the dark (top) or light (bottom) condition.
Figure 17A:
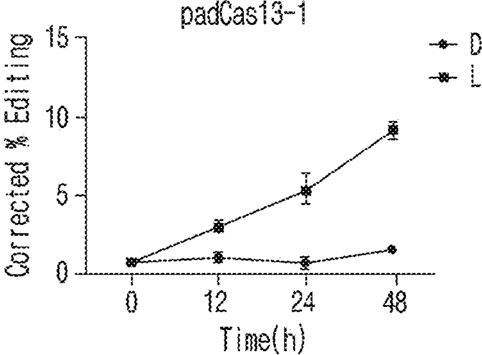
FIG. 17 is a set of graphs showing the RNA editing percentage quantified and normalized by RT-PCR-Sanger sequencing (D: dark, L: light).
Figure 17B:
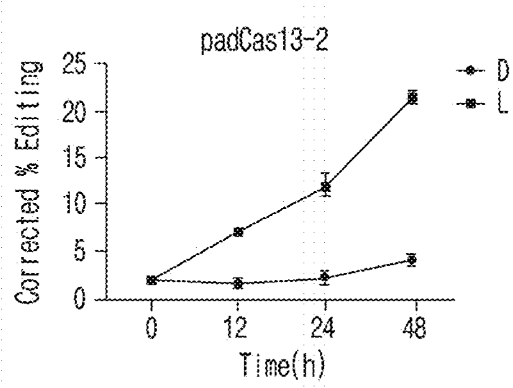
Figure 18:
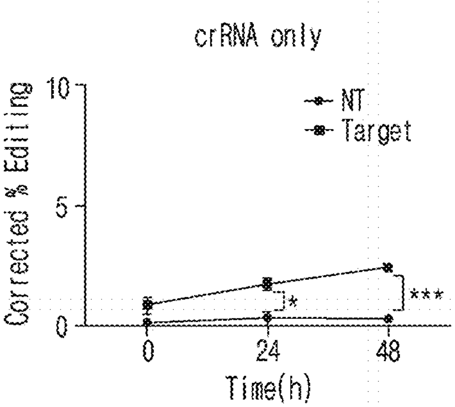
FIG. 18 is a graph showing the RNA editing percentage of transfected cells having only crRNA by RT-PCR-Sanger sequencing.

The levels of RNA editing with or without light stimulation and over time were measured for up to 48 hours. As a result, as shown in FIG. 15, it was confirmed that A-to-I RNA editing was performed over time in the presence of light stimulation. In addition, it was confirmed that the RNA editing level of the target site by the padCas13 editor was steadily increased over time (FIGS. 16 and 17). Since the cells transfected with only crRNA also exhibited a moderate A-to-I editing rate, the background activity observed in the dark state was regarded as the RNA editing background unrelated to padCas13 (FIG. 18).

The above results suggest that the padCas13 editor of the present invention is capable of reversible RNA editing in a light-dependent manner.

To evaluate the efficiency and specificity of the padCas13 system of the present invention, transcriptome-wide RNA-sequencing (RNA-seq) was performed on the cells transfected with the padCas13 editor targeting Fluc W417X mutation.

Figure 19:
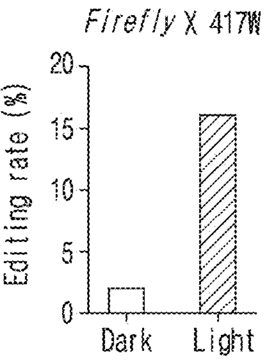
FIG. 19 is a graph showing the deep-sequencing quantification (n=1) of A-to-I RNA editing by the padCas13 editor under the light stimulation for 24 hours.
Figure 20:
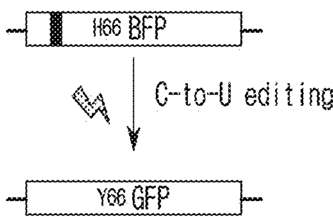
FIG. 20 is a schematic diagram showing the EGFP indicator for the light-induced C-to-U RNA editing activity.

As a result, as shown in FIG. 19, it was confirmed that the target editing rate was 16% under the light stimulation for 24 hours.

The padCas13 editor was able to induce the target A-to-I editing, but many "A" sites around the target site were accessible via the fused ADAR2 of the padCas13 editor. These sites also bound crRNA to form a RNA duplex structure, the natural editing target structure of the endogenous ADAR2 enzyme. Therefore, RNA sequencing was performed to also analyze adenosines surrounding the target mutation site (Fluc W417X).

Specifically, HEK293T cells were plated in 24-well plates (SPL) and co-transfected with 250 ng of each paCas13 fragment expressing the plasmid and 300 ng of crRNA. After the light stimulation, total RNA was extracted using a PureLink RNA mini kit (Invitrogen), and DNase (Invitrogen) treatment was performed in the column for 15 minutes. A strand mRNA library was prepared using a TruSeq stranded mRNA library kit (Illumina) and sequenced at Illumina NextSeq550 with 76 nt paired-end reading. About 130 million total reads per condition were demultiplexed. Sequencing raw data were processed using PIGx RNA-seq (https://github.com/BIMSBbioinfo/pigx rnaseq).

As a result, no additional A-to-I editing was observed at adenosine sites other than the target.

These results indicate that the padCas13 editor is capable of light-inducible and highly specific A-to-I RNA editing.

<2-2-2> Light-Inducible C-to-U RNA Editing by paCas13

A light-inducible C-to-U RNA editing system was constructed by fusion of the padCas13 fragment to ADAR2DD capable of cytidine deamination. To verify the activity of the padCas13 editor for C-to-U nucleotide editing, a fluorescent protein-based indicator was designed (FIG. 20), and fluorescence imaging and flow cytometry were performed.

Particularly, for C-to-U RNA editing, evolved ADAR2 DD mutations (including E488Q/V351G/S486A/T375A/S370C/P462A/N597I/L332I/I398V/K350I/M383L/D619G/S452T/S48) were amplified in pc0079 RESCUE-S (Addgene plasmid 130662). To develop this system, a mutation (Y66H green to blue: Y66H (UAC→CAC)) was introduced into GFP of the EGFP-N1 plasmid by Gibson Assembly. In addition, a crRNA targeting the target CAC codon causing C-to-U conversion was designed. Under the light stimulation, the padCas13 editor can perform C-to-U conversion of Y66H mutation and restore GFP fluorescence. To enhance the effect of C-to-U RNA editing, two vectors were cloned by Gibson assembly following expansion PCR cloning. The first vector expresses the N-terminus of crRNA and the pMag-conjugated dCas13 fragment linked to a GFP indicator via a T2A self-cleaving peptide. Each sequence is controlled by hU6 promoter and EFS (EF1a short) promoter, respectively. The second vector expresses the C terminus of the dCas13 fragment fused with nMagH and ADAR2DD under the control of the EFS promoter.

Live-cell imaging was performed with a Nikon A1R confocal microscope mounted on a Nikon Eclipse Ti body equipped with a Nikon CFI PlanApochromat VC 60X/1.4 numerical aperture (NA) and a digital-zooming Nikon imaging software (NIS-elements AR 64-bit version 3.21). A Chamlide TC system placed on a microscope stage was used to maintain environmental conditions of 37° C. and 10% $CO_2$ (Live Cell Instruments). A custom 96-well 488 nm LED array (Live Cell Instruments) was used to irradiate uniform blue light in all wells.

To perform flow cytometry, HEK293T cells were seeded in a 6-well plate (SPL) at the density of $3\times10^5$ cells/well using a GFP indicator. After 24 hours, the GFP indicator and padCas13 editor plasmids were co-transfected using Lipofectamine LTX (Invitrogen) according to the manufacturer's manual. The percentage of GFP+ in cells indicates editing efficiency. The transfected cells were analyzed by BD FACSLSRFortessa 24 hours after the light stimulation. Only live single cells were used for fluorescence analysis. The results of flow cytometry were analyzed with FlowJo X (v. 10.0.7).

Figure 21:
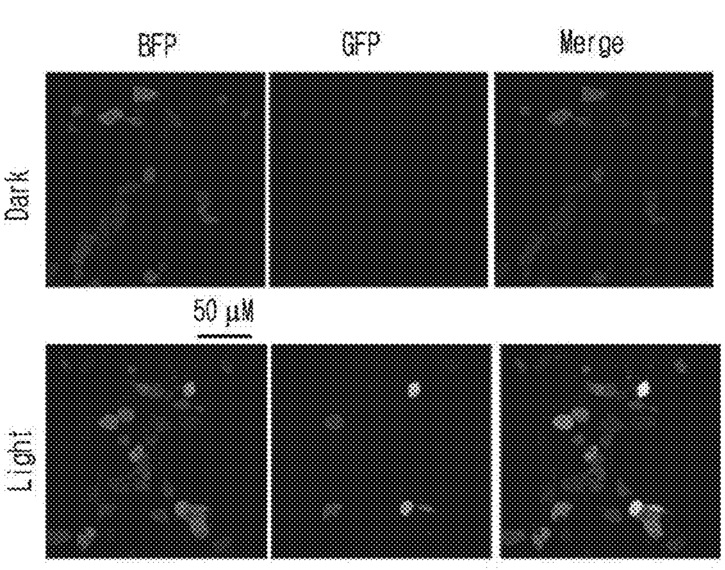
FIG. 21 is a diagram showing the representative fluorescence microscopy images of HEK293T cells co-transfected with the padCas13-2 editor, EGFP indicator and target crRNA.
Figure 22:
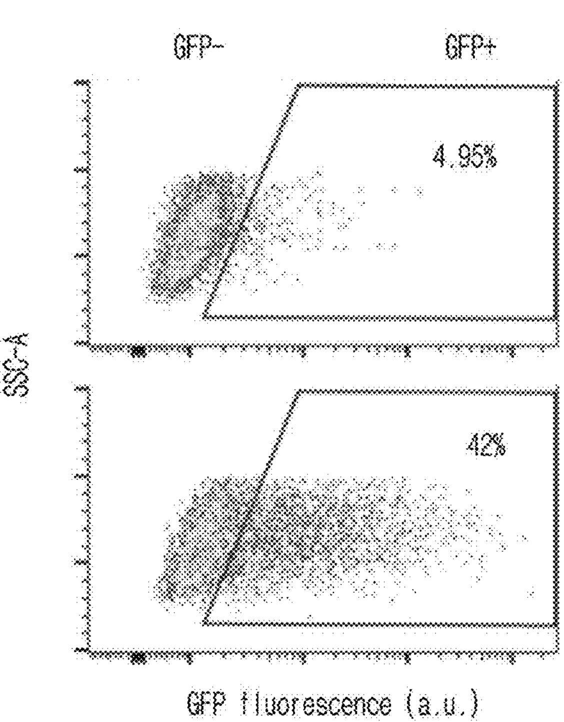
FIG. 22 is a set of graphs showing the representative flow cytometry plots transfected with the padCas13-2 editor [X-axis: FITC-A (log scale), Y-axis: SSC-A (linear scale)].
Figure 23:
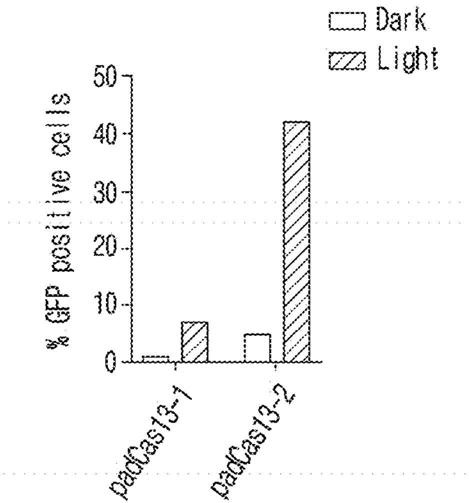
FIG. 23 is a graph showing the quantification of EGFP H66Y restored by the padCas13 editor.

The padCas13 editor and the target crRNA or non-target crRNA (NT, negative control) were transfected with the GFP indicator and the light inducibility upon blue light stimulation was tested for 24 hours. As a result, as shown in FIG. 21, it was confirmed that the padCas13 editor induced C-to-U RNA editing to generate BFP/GFP double positive cells under the light stimulation. It was also confirmed that the GFP restoration caused by C-to-U editing was increased from 4.95% to 42% by blue light illumination compared to the dark condition (FIGS. 22 and 23).

Through the above results, it was confirmed that the padCas13 system of the present invention has a light-dependent RNA editing activity suitable for both A-to-I and C-to-U nucleotide editing.

<2-2-3> Light-Inducible Endogenous Transcript Editing by padCas13

Whether the light-inducible padCas13 editor of the present invention can be applied to edit endogenous transcripts was evaluated.

Figure 24:
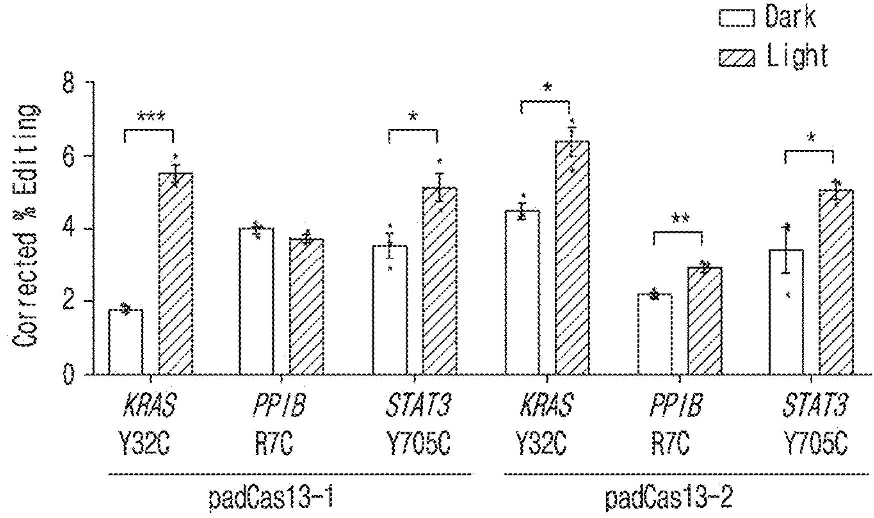
FIG. 24 is a graph showing the A-to-I RNA editing percentage by the padCas13-1 or padCas13-2 editor under the light stimulation for 24 hours (error bar, mean±sem, n=3).
Figure 25:
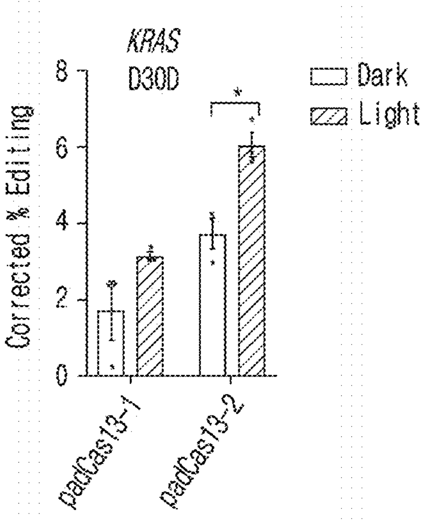
FIG. 25 is a graph showing the C-to-U RNA editing percentage by the padCas13-1 or padCas13-2 editor under the light stimulation for 24 hours (error bar, mean±sem, n=3).

As a result, as shown in FIGS. 24 and 25, it was confirmed that the padCas13 editor of the present invention can mediate A-to-I and C-U editing of all the subjects tested in a light-induced manner.

These results indicate a high possibility of using padCas13 to ameliorate a disease. In particular, the use of padCas13 has a h high potential to improve the disease state that requires temporal regulation of disease-related RNA molecules.

What is claimed is:

1. A method for regulating the activity of Cas13 protein, comprising a step of treating a first fragment containing the N-terminal segment of Cas13 protein and a first regulatory protein; and a second fragment containing a second regulatory protein and the C-terminal segment of Cas 13 protein with a compound;

wherein the N-terminal segment of the Cas13 protein is a segment from the N-terminus of the Cas 13 protein to the 272nd, 286th, 351st, 480th or 928th amino acid of the Cas13 protein, and wherein the C-terminal segment of the Cas13 protein is a segment from the 273rd, 287th, 352nd, 481st or 929th amino acid of the Cas13 protein to the C-terminus of the Cas13 protein.

2. The method for regulating the activity of Cas13 protein according to claim 1, wherein the compound treatment induces dimerization of the first regulatory protein and the second regulatory protein.

3. The method for regulating the activity of Cas13 protein according to claim 1, wherein a linker is inserted between the N-terminal segment of Cas13 protein and the first regulatory protein, and between the second regulatory protein and the C-terminal segment of Cas13 protein.

4. The method for regulating the activity of Cas13 protein according to claim 3, wherein the linker includes glycine (G) and serine(S).

5. The method for regulating the activity of Cas13 protein according to claim 1, wherein the Cas13 protein is at least one selected from the group consisting of Cas13a, Cas13b, Cas13c and Cas13d.

6. The method for regulating the activity of Cas13 protein according to claim 5, wherein the Cas13 protein is PspCas13b protein.

7. The method for regulating the activity of Cas13 protein according to claim 1, wherein the compound is rapamycin.

8. The method for regulating the activity of Cas13 protein according to claim 1, wherein the combination of the first regulatory protein and the second regulatory protein is FKBP-FRB.

9. A method for modulating the expression of a target RNA comprising the following steps:

1) preparing a vector comprising a construct containing a sequence encoding the N-terminal segment of Cas13 protein and a sequence encoding a first regulatory protein; and a vector comprising a construct containing a second fragment comprising a sequence encoding a second regulatory protein and a sequence encoding the C-terminal segment of Cas13 protein;
2) injecting the vector above and crRNA (CRISPR RNA) capable of hybridizing to the target RNA sequence into mammalian cells; and
3) treating the cells with a compound;

wherein the N-terminal segment of the Cas13 protein is a segment from the N-terminus of the Cas13 protein to the 272nd, 286th, 351st, 480th or 928th amino acid of the Cas13 protein, and wherein the C-terminal segment of the Cas13 protein is a segment from the 273rd, 287th, 352nd, 481st or 929th amino acid of the Cas13 protein to the C-terminus of the Cas13 protein.

10. The method for modulating the expression of a target RNA according to claim 9, wherein the crRNA includes a guide sequence and a direct repeat sequence capable of hybridizing to the target RNA sequence.

11. The method for modulating the expression of a target RNA according to claim 9, wherein the vector is a virus or a plasmid.

12. The method for modulating the expression of a target RNA according to claim 11, wherein the virus is adeno-associated virus (AAV), adenovirus, retrovirus, lentivirus, modified vaccinia virus ankara (MVA), herpes simplex virus or baculovirus.

* * * * *